US007153652B2

(12) United States Patent
Cox et al.

(10) Patent No.: US 7,153,652 B2
(45) Date of Patent: Dec. 26, 2006

(54) MISMATCH REPAIR DETECTION

(75) Inventors: David R. Cox, Belmont, CA (US); Malek Faham, Daly City, CA (US); Siamak Baharloo, San Francisco, CA (US)

(73) Assignees: The Board of Trustees of the Leland Stanford Junior University, Palo Alto, CA (US); The Regents of the University of California, San Francisco, CA (US)

( * ) Notice: Subject to any disclaimer, the term of this patent is extended or adjusted under 35 U.S.C. 154(b) by 277 days.

(21) Appl. No.: 10/081,771

(22) Filed: Feb. 20, 2002

(65) Prior Publication Data

US 2003/0003472 A1    Jan. 2, 2003

Related U.S. Application Data

(63) Continuation-in-part of application No. 10/072,047, filed on Feb. 8, 2002, now Pat. No. 6,709,827, and a continuation-in-part of application No. 09/271,055, filed on Mar. 17, 1999, now Pat. No. 6,406,847, which is a continuation-in-part of application No. 08/713,751, filed on Sep. 13, 1996, now abandoned.

(60) Provisional application No. 60/004,664, filed on Oct. 2, 1995.

(51) Int. Cl.
*C12Q 1/68* (2006.01)
*C12P 19/34* (2006.01)
*C07H 21/02* (2006.01)

(52) U.S. Cl. .......................... 435/6; 435/91.2; 536/23.1
(58) Field of Classification Search ...................... None
See application file for complete search history.

(56) References Cited

U.S. PATENT DOCUMENTS

| 4,959,317 A | 9/1990 | Sauer |
| 5,376,526 A | 12/1994 | Brown et al. |
| 5,654,182 A | 8/1997 | Wahl et al. |
| 5,679,522 A | 10/1997 | Modrich et al. |

FOREIGN PATENT DOCUMENTS

| WO | WO 97/12993 | 4/1997 |
| WO | WO 00/55368 | 9/2000 |

OTHER PUBLICATIONS

Fang et al. Methyl-directed repair of mismatched small heterologous sequences in cell extracts from *Escherichia coli*. 1997. Journal of Biological Chemistry vol. 272:22714-22720.*
Faham et al., "High Throughput Scanning for Variations by Mismatch Repair Detection (MRD)", American Journal of Genetics, 1999, 65(4): A99.
Faham et al., "Mismatch Repair Detection (MRD): High-Throughput Scanning for DNA variations", Human Molecular Genetics, 2001, 10(16): 1657-1664.
Bishop, et al. "The power of identity-by-state methods for linkage analysis", *Am. J. Hum. Genet.*, (1990) vol. 46: 254-265.
Brookes, et al. "Cloning the shared components of complex DNA resources", *Human Molecular Genetics*, (1994) vol. 3: 2011-2017.
Camerini-Otero, (1991), *Nature Genetics*, 5:11.
Carraway, et al. "Repair of heteroduplex DNA molecules with multibase loops in *Escherichia coli*", *J. Bacteriology*, (1993) vol. 175:3972-3980.
Casna, et al. "Genomic analysis II: Isolation of high molecular weight heteroduplex DNA following differential methylase protection and formamide-PERT hybridization", *Nucleic Acids Res.*, (1986) vol. 14(18):7285-7303.
Cotton, et al. "Reactivity of cytosine and thymine in single-base-pair mismatches with hydroxylamine and osmium tetroxide and its application to the study of mutations", *Proc. Natl. Acad. Sci. USA*, (1988) vol. 85:4397-4401.
Dias, et al. "Genetic recombination as a reporter for screening steroid receptor agonists and antagonists", *Anal. Biochem.*, (1998) vol. 258:96-102.
Ferrin, et al. "Selective cleavage of human DNA: RecA-assisted restriction endonuclease (RARE) cleavage", *Science* (1991) vol. 254: 1494-1497.
Grompe. "The rapid detection of unknown mutations in nucleic acids", *Nature Genetics*, (1993) vol. 5: 111-117.
Lander, et al. "Homozygosity mapping: A way to map human recessive traits with the DNA of inbred children", *Science*, (1987) vol. 236: 1567-1570.
Mashal, et al. "Detection of mutations by cleavage DNA heteroduplexes with bacteriophage resolvases", *Nature Genetics*, (1995) vol. 9: 177-183.
Mills, et al., "Electrophoretic Evidence That Single Stranded Regions of One or More Nucleotides Dramatically Increase the Flexibility of DNA," *Biochemistry* (1994), vol. 33: 1797-1803.

(Continued)

*Primary Examiner*—Gary Benzion
*Assistant Examiner*—Heather G. Calamita
(74) *Attorney, Agent, or Firm*—Pamela J. Sherwood; Bozicevic, Field & Francis LLP

(57) ABSTRACT

Mismatch Repair Detection (MRD), a novel method for DNA-variation detection, utilizes bacteria to detect mismatches by a change in expression of a marker gene. DNA fragments to be screened for variation are cloned into two MRD plasmids, and bacteria are transformed with heteroduplexes of these constructs. Resulting colonies express the marker gene in the absence of a mismatch, and-lack expression in the presence of a mismatch. MRD is capable of detecting a single mismatch within 10 kb of DNA. In addition, MRD can analyze many fragments simultaneously, offering a powerful method for high-throughput genotyping and mutation detection.

21 Claims, 16 Drawing Sheets

OTHER PUBLICATIONS

Modrich. "Mechanisms and biological effects of mismatch repair", *Annu. Rev. Genet.*, (1991) vol. 25: 229-253.

Myers, et al. "Nearly all single base substitutions in DNA fragments joined to a GC-clamp can be detected by denaturing gradient gel electrophoresis", *N.A.R.*, (1985) vol. 13:3131-3145.

Myers, et al. "Detection of sinlge base substitutions by ribonuclease cleavage at mismatches in RNA: DNA duplexes", *Science*, (1985) vol. 230: 1242-1246.

Myers, et al. "Detection and localization of single base changes by denaturing gradient gel electrophoresis", *Meth. Enzym.*, (1987) vol. 155: 501-527.

Orita, et al. "Rapid and sensitive detection of point mutations and DNA polymorphisms using the polymerase chain reaction", *Genomics*, (1989). vol. 5: 874-879.

Orita, et al. "Detection of polymorphisms of human DNA by gel electrophoresis as single-strand conformation polymorphisms", *P.N.A.S.*, (1989) vol. 86: 2766-2770.

Parker, et al. "Repair of DNA heteroduplexes containing small heterologous sequences in *Escherichia coli*", *P.N.A.S.*, (1992) vol. 89:1730-1734.

Perry, et al. "Hydrolink gels: A rapid and simple approach to the detection of DNA mutations in thromboembolic disease", *Clin Pathol.*, (1992) vol. 45: 158-160.

Raposa, et al., "Some Features of Base Repair Mismatch and Heterology Repair in *Escherichia coli*," *Genetics* (1987), vol. 117: 381-390.

Risch. "Linkage strategies for genetically complex traits: The power of affected relative pairs", *Am. J. Hum. Genet.*, (1990) vol. 46: 229-241.

Sanda, et al. "Genomic analysis I: Inheritance units and genetic selection in the rapid discovery of locus linked DNA markers", *Nucleic Acids Res.*, (1986) vol. 14: 7265-7282.

Sheffield, et al. "Attachment of a 40-base-pair G+C-rich sequence (GC-clamp) to genomic DNA fragments by the polymerase chain reaction results in improved detection of single-base changes", *P.N.A.S.* (1989), vol. 86: 231-236.

Wagner, et al. "Repair tracts in mismatched DNA heteroduplexes", *P.N.A.S.*, (1976) vol. 73: 4135-4139.

Wang, et al. "Large-scale identification, mapping, and genotyping of single-nucleotide polymorphisms in the human genome", *Science*, (1998), vol. 280: 1077-1082.

White, et al. "Detecting single base substitutions as heteroduplex polymorphisms", *Genomics*, (1992). vol. 12: 301-306.

Youil, et al. "Screening for mutations by enzyme mismatch cleavage with T4 endonuclease VII", *P.N.A.S.*, (1995) vol. 92: 87-91.

* cited by examiner

Genomic copy Y sequence

PCR amplification

Denature

Hybridize vectors and Y strand. Ligate.

Cells are grown in two tubes supplemented either with

Tetracycline      or      Streptomycin

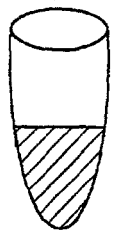    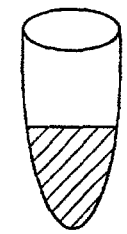

Next day DNA is preped from the pool of the cells grown in each tube

DNA from the Tet pool is labeled with green fluorescence

DNA from the Strep pool is labeled with red fluorescence

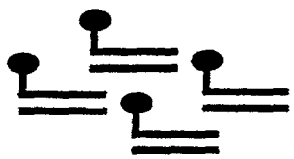    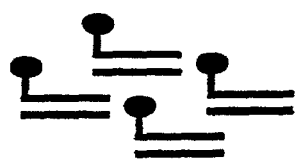

DNA from both pools are mixed and hybridized to a DNA microarray.
Each spot corresponds to a different gene fragment that is being tested

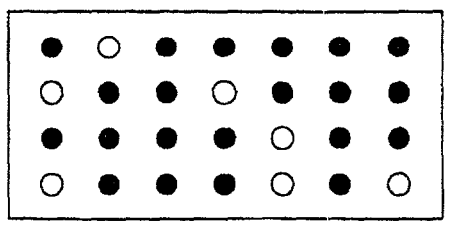

*FIG. 6C* elimination of wholly or partially single stranded species ligation of compatible ends

MISMATCH REPAIR DETECTION

CROSS-REFERENCE TO RELATED APPLICATIONS

This application is a continuation-in-part of U.S. patent application Ser. No. 09/271,055, filed Mar. 17, 1999, now U.S. Pat. No. 6,406,847, which is a continuation-in-part of U.S. patent application Ser. No. 08/713,751, filed Sep. 13, 1996 now abandoned, which claims priority to U.S. Provisional Patent Application No. 60/004,664, filed Oct. 2, 1995, the disclosures of which are incorporated herein by reference in their entireties.

STATEMENT REGARDING FEDERALLY SPONSORED RESEARCH

This invention was made with government support under Contract Nos. HD 24610 07-10 and 5T32GM07618 awarded by the National Institutes of Health. The Government has certain rights in this invention.

BACKGROUND OF THE INVENTION

The detection of mutations in genomic DNA plays a critical role in efforts to elucidate the genetic basis of human disease. For many types of genetic screening and analysis, knowledge of the presence of a mutated copy of a gene is essential. Such information may be used in prenatal and other genetic testing, as well as analysis of tumor cells and other somatic mutations. For many genes, there are a number of different mutations that can affect function.

Common diseases such as diabetes, heart disease and psychiatric disorders are caused in part by genetic variations in multiple genes. Genetic variations are not only involved in the genesis of diseases but they are also chief determinants of disease progression and response to treatment. Identification of the genetic variations involved in common diseases can greatly improve the diagnosis, prognosis, and treatment of such diseases.

One approach for identifying the potentially causative variations involved in common diseases is to screen patients and controls for genetic variations in a large number of candidate genes. Genetic coding sequences constitute less than 5% of the entire human genome, yet the vast majority of human diseases are caused by sequence variation in these coding sequences. Reagents for large scale screening of genes are already available, as a significant proportion of human gene sequences exists in the rapidly expanding public databases. Many DNA variation screening methods have been developed, e.g. single stranded conformational polymorphism (SSCP); and high performance liquid chromatography (HPLC). Since these methods are not designed to screen many genes simultaneously, their usefulness has been limited to testing a handful of candidate genes.

In the absence of high throughput technology capable of large scale screening of genes for the identification of variations involved in diseases, less straight forward approaches such as association and linkage mapping have been proposed. In these approaches, neutral genetic variations (polymorphic markers) are cataloged into a genetic map. These polymorphic markers are used in a genetic linkage or association analysis to approximate the chromosomal location of the disease genes.

Association studies are based on the probability that certain polymorphisms in close proximity to the ancestral disease-causing variation are still present in today's patient population. In linkage or association mapping one hopes that at least a single marker is sufficiently close to the disease-causing variation, and therefore would co-segregate with the disease in a family or in a population. The analysis assumes that a large proportion of the mutations had a single point of origin.

Linkage and association based approaches have been successful for mapping of simple Mendelian diseases. However, mapping of diseases with a complex mode of inheritance has been less successful. Identification of the variations that are involved in such diseases is widely believed to require the performance of association analysis using tens of thousands of markers. Because single nucleotide polymorphisms (SNPs) are the most prevalent polymorphisms, they are proposed to be the markers of choice for these association studies.

Multiple methods, such as chip hybridization and oligonucleotide ligation assay (OLA), have been developed for genotyping of SNPs. All these SNP genotyping methods operate on a common principle of genotyping a previously identified single base polymorphism. Polymorphic sites are first identified by sequencing multiple individuals, then compiled into a map. Finally, patients and controls are tested for the presence or absence of each polymorphism.

In view of the importance of genetic testing, methods whereby one can easily screen for genetic mismatches between two DNA molecules is of great interest. A simple method to determine whether two DNA molecules are identical or different, and that is capable of multiplex analysis would be of great benefit in these analyses.

The identification of single nucleotide polymorphisms (SNPs) covering the entire genome will lead to numerous association studies of complex traits. Most scenarios for such studies assume a universal set of relatively frequent SNPs, distributed in all or most ethnic populations. One widely considered approach is to identify susceptibility alleles through direct association studies using SNPs located in coding or regulatory sequences. The main alternative strategy is to search for linkage disequilibrium (LD) between disease susceptibility alleles and SNPs from a dense genome-wide map. Either of the above approaches requires efficient genotyping to score for the presence or absence of previously identified SNPs. Both approaches, however, may be unrealistic when variant alleles, either those directly responsible for disease susceptibility or SNPs, are infrequent or are specific to a particular population. In such cases, identifying susceptibility alleles may require comprehensive sequence comparison between patients and control. Accomplishing such sequence comparison requires a high throughput DNA variation scanning technology to identify all possible variations in the tested fragments. The Variant Detection Array (VDA) method is perhaps the only existing approach for DNA variant scanning with a high potential for parallel processing. However, VDA is expensive and may be sub-optimally specific and sensitive.

Relevant Literature

Techniques for detection of conformational changes created by DNA sequence variation as alterations in electrophoretic mobility are described in Orita et al. (1989) *P.N.A.S.* 86:2766; Orita et al. (1989) *Genomics* 5:874; Myers et al. (1985) *N.A.R.* 13:3131 (1985); Sheffield et al. *P.N.A.S.* 86:231; Myers et al. *Meth. Enzym* 155:501; Perry and Carrell (1992) *Clin. Pathol.* 45:158; White et al. (1992) *Genomics* 5:301.

Techniques that use chemicals or proteins to detect sites of sequence mismatch in heteroduplex DNA are described in Cotton et al. (1988) *P.N.A.S.* 85:4397; Myers et al. (1985)

Science 230:1242; Marshal et al. (1995) *Nature Genetics* 9:177 (1995); Youil et al. (1995) *P.N.A.S.* 92:87. Chip hybridization is described in Wang et al. *Science* 280: 1077–82.

Grompe (1993) *Nature Genetics* 5:111 reviews methods for screening large stretches of DNA. Mapping strategies may be found in Risch (1990) *Am. J. Hum. Genet.* 46:229–241; Lander and Botstein (1987) *Science* 236:1567–1570; and Bishop and Williamson (1990) *Am. J. Hum. Genet.* 46:254–265. Sandra and Ford, (1986) *Nucleic Acids Res.* 14:7265–7282 and Casna, et al. (1986) *Nucleic Acids Res.* 14:7285–7303 describe genomic analysis.

However, several approaches are presently available to isolate large DNA fragments, including long range PCR with enzymes with high fidelity described in Nielson et al. (1995) *Strategies* 8:26; recA-assisted cleavage described by Ferrin and Camerini-Otero (1991) *Science* 254:1494; and the use of a single set of oligonucleotide primers to PCR amplify multiple specific fragments simultaneously in Brookes et al. (1995) *Human Molecular Genetics* 3:2011.

The *E. coli* methyl mismatch repair system is described in Wagner and Messelson (1976) *P.N.A.S.* 73:4135; Modrich (1991) *Annu. Rev. Genet.* 25:229; Parker and Marinus (1992) *P.N.A.S.* 89:1730; and Carraway and Marinus (1993) *J. Bacteriology* 175:3972. The normal function of the *E. coli* methyl-directed mismatch repair system is to correct errors in newly synthesized DNA resulting from imperfect DNA replication. The system distinguishes unreplicated from newly replicated DNA by taking advantage of the fact that methylation of adenine in the sequence GATC occurs in unreplicated DNA but not in newly synthesized DNA. Mismatch repair is initiated by the action of three proteins, MutS, MutL and MutH, which lead to nicking of the unmethylated, newly replicated strand at a hemimethylated GATC site. The unmethylated DNA strand is then digested and resynthesized using the methylated strand as a template. The methyl-directed mismatch repair system can repair single base mismatches and mismatches or loops of up to four nucleotides in length. Loops of five nucleotides and larger are not repaired.

The use of site specific recombinases in eukaryotic cells is described by Wahl et al., U.S. Pat. No. 5,654,182; and by Sauer, U.S. Pat. No. 4,959,317.

SUMMARY OF THE INVENTION

The present invention solves these and other needs in the art by providing, in a first aspect, an in vivo method of detecting a mismatch in any of a plurality of DNA duplexes of distinct nucleic acid sequence. The method comprises detecting, for any of the plurality of duplexes, an alteration in a characteristic of a cell, where the alteration in cellular phenotype is caused by corepair of a marker that is present together with the duplex in a vector within the cell, wherein the corepair is initiated by a mismatch that is present in the duplex. Typically, the duplexes are formed in a single hybridization reaction.

In one series of embodiments, the cell is a bacterial cell, and mismatch corepair is mediated by a bacterial methyl mismatch repair system.

In such embodiments, methods and compositions are provided for an in vivo bacterial assay, termed "Mismatch Repair Detection" (MRD). The method detects mismatches in a double stranded DNA molecule, where the sequence of one strand differs from the sequence of the other strand by as little as a single nucleotide. The two strands of the DNA molecule are from different sources. One strand is unmethylated DNA, having a detectable marker gene and the sequence being tested for mismatches. The other strand is methylated DNA, having an inactivated copy of the marker gene where the defect does not activate repair mechanisms, and another copy of the sequence to be tested. Heteroduplex dsDNA formed from the hybridization of the two strands is transformed into a bacterial host with an active methyl mismatch repair system (MMR host).

The host repair system is activated by a mismatch in the sequence of interest, and will then "co-repair" the marker gene, to produce an inactive, double stranded copy. When the two strands of the sequence of interest are a perfect match, the marker gene is not altered, and the transformed bacteria will produce active marker. Where a mismatch is present, the transformants are readily identified by the lack of active marker, and may then be isolated and grown for further analysis. MRD is a rapid method for analysis of numerous fragments simultaneously. It is useful as an assay for enumerating differences between various sources of DNA, and as a means of isolating DNA with variant sequences.

The method will determine whether two DNA sequences differ by as little as a single base change, in a region of over 10,000 nucleotides. Multiple DNA fragments can be analyzed in a single reaction, and the process is easily scaled up to run large numbers of reactions in parallel. Depending on the input DNA, MRD can be used for various purposes. It is used in genetic mapping by testing a large number of polymorphic markers in order to analyze large regions of eukaryotic chromosomes for the presence of mutations. In a large pool of genomic or cDNA clones, the method will identify those DNAs where there is a mismatch between the control and test population, providing a particularly simple method of isolating variant alleles from a particular locus or region. The method can also be used to detect somatic changes in DNA, such as those found in tumor cells, or in the hypermutation of antibody genes. A key advantage of MRD is that, once provided with suitable vectors, the procedure is extremely easy to perform.

The ability to perform high throughput DNA variation detection makes Mismatch Repair Detection (MRD) ideal for performing association and direct screening studies. MRD's multiplexing potential exceeds that of currently known methods, therefore offering an improvement over other methods for large scale SNP genotyping.

MRD also can be used to screen a massive number of candidate genes in order to identify disease-causing variations. It is possible to test the coding regions of all human genes in a limited number of MRD reactions. Testing the coding regions of all the genes in a population of patients and controls will readily reveal disease-causing variations. Sensitivity of this direct approach is significantly higher than that of the association studies as it does not require assumptions as to the origin of mutation and the prevalence of the disease-carrying ancestral chromosome in the patient population. Methods detecting disease-causing variations directly are more likely than association methods to succeed in identifying these variations. This direct candidate gene screening approach is powerful and effective and can greatly accelerate the identification of variations causing clinically-significant phenotypes, greatly improving disease diagnosis, prognosis, and treatment.

Applications of the method based on direct screening of disease genes include diagnosis; sub-diagnosis where one distinguishes between mutations in two related disease associated genes, e.g. factor VIII vs. factor IX deficiency; prognosis of disease susceptibility; treatment development; and treatment optimization.

The invention further provides compositions, including vectors, and methods that facilitate highly multiplexed mismatch repair detection for rare allele detection and scoring.

In a first such aspect, the present invention provides a mismatch repair detection method in which each nucleic acid standard is physically linked in the standard vector (and thus in the resulting MRD vector) not only to a phenotypically sortable genetic element, but additionally to a genotypically detectable genetic element. The former permits in vivo phenotypic sorting according to the presence or absence of an initiating mismatch in the test duplex; the latter permits improved in vitro identification of the test duplexes so sorted.

In general, the method of this aspect of the invention comprises phenotypically sorting from the plurality of distinct duplexes those that are capable of initiating a mismatch corepair event in vivo, and then identifiably detecting the genotypically detectable genetic element that is uniquely linked to each duplex so sorted.

In a first series of embodiments of this aspect of the invention, each of the genotypically detectable genetic elements is a nucleic acid sequence tag, each of the sequence tags being unique among the plurality of sequence tags, and the sorted duplexes are identified by specific hybridization of the sequence tags, the sequence tagged duplexes, or nucleic acids derived therefrom to a microarray that has probes complementary to the plurality of sequence tags.

A number of advantages are realized by using the specific hybridization of genotypically-linked sequence tags to bar code microarrays to detect and identify the phenotypically sorted standards in the present invention.

First, standards of distinct sequence that differ by only a few nucleotides can as readily be discriminated as can standards differing substantially in sequence, permitting a plurality of allelic variants of a locus to be used concurrently to query a sample for variation at a single locus. Such concurrent query permits a rare allele to be detected as a sequence that differs concurrently from all of the common alleles. As few as two, or three, and as many as four, five, six, seven, even 10 or more allelic variants of any given locus can be detectably included as separately tagged standards in a single reaction.

Second, because the microarray is specific for the tags, rather than for the standards, generic bar code microarrays can be constructed that can be used for any pool of standards, so long as the standards are physically linked in the standard and MRD vectors to the requisite, complementary, sequence tags.

Third, the generic nature of the bar code microarray allows a single set of optimal hybridization conditions to be determined, and thereafter used without individualization or further optimization.

The method readily permits multiplex query of sequence variation present in genomic samples, such as samples drawn from yeast, plants, and mammals, including human beings. The method also readily permits concurrent use of standards having sequence identical to a plurality of allelic variants of a single genomic locus, from two, to three, four, even five or more allelic variants of any desired locus, and permits concurrent query of up to 100,000 loci.

In a second aspect directed to rare allele detection and scoring, the invention provides an improved standard vector for use in the improved mismatch repair detection methods of the first aspect of the invention, the improved vector having a genotypically detectable genetic element uniquely linked to the vector's standard sequence.

These related aspects of the invention increase the multiplexing capacity of mismatch repair detection (MRD)—that is, increase the number of standards of distinct sequence that can concurrently be used to query a sample for the presence of sequence variation. However, alleles that occur within a population with frequency less than the background of the MRD assay system remain difficult to detect reliably from pooled nucleic acid samples.

Accordingly, in a third such aspect, the invention provides standard vectors that decrease background in the MRD assay.

In this aspect, the invention provides standard vectors that decrease background, in the MRD assay by operatively linking the phenotypically sortable genetic element to a regulated strong promoter and a heterologous ribosomal binding site, thus improving expression of the phenotypically sortable genetic element before plasmid segregation. In embodiments that are presently preferred, the regulated strong promoter is a T7 promoter.

The low background vectors of this aspect of the invention can usefully further include genotypically detectable elements uniquely linked to the standard sequence, which permits the "bar-code" hybridization approach, with its increased multiplexing capacity, to be practiced using low background vectors.

In a fourth such aspect, the invention provides a method of preparing standard vectors, including the improved standard vectors above-described, that further decreases background.

The method comprises propagating a double-stranded closed circular vector in a bacterial strain under conditions permissive for dam expression—the vector comprises a plasmid origin of replication, a filamentous phage origin of replication, a standard sequence, and a phenotypically sortable genetic element. Thereafter, the propagation conditions are changed to be nonpermissive for dam expression, and then closed circular single stranded nucleic acids (standard vectors) are rescued from the propagated vector by infection of the bacterial strain with helper phage.

Reducing the period of propagation in a dam⁻ strain reduces the introduction of spontaneous mutations that can initiate repair even in the absence of an initiating mismatch in the test duplex.

In a fifth such aspect, the invention provides improved mismatch repair vectors that improve the signal in the MRD reaction, which also improves the signal:noise ratio.

In one series of embodiments, the improvement comprises positioning the mismatch in the phenotypically sortable genetic element to be no more than 200 nucleotides from the test duplex. In another series of embodiments, the improvement comprises reversing the orientation of the filamentous phage origin, thus obligating plasmid replication (and thus any repair attendant thereupon) before expression of the phenotypically sortable genetic element.

Individually and together, these improvements permit rare allelic variants more readily to be detected as sequences that differ from all common alleles, which common alleles can now readily be included as concurrent standards in a single assay.

In a sixth such aspect, the invention makes possible the ready discovery of such common alleles, thus further facilitating discovery and scoring of rare alleles.

In the method of this aspect of the invention, the sample being queried is pooled from a plurality of individuals. The sample can be drawn from as few as 2 individuals, but is typically pooled from at least 3, 4, 5, 10, 15, even at least 20, 25, 30, 35, or 40, 45, or 50 individuals or more. Although a single locus can be screened, higher throughput is achieved by multiplex analysis, in which a plurality of loci are concurrently queried.

The first step of the method comprises preparing MRD vectors for each locus desired to be screened using, as the query sample, nucleic acids pooled from a plurality of individuals. The standard will be an identified allele of a chosen locus. The resulting MRD vectors, with their respective test duplexes, are then phenotypically sorted based upon the ability of each included duplex to initiate a mismatch corepair event in vivo. The duplexes present in the phenotypically sorted population are detected and identified, with detection and identification being performed by detecting the genotypically detectable genetic element linked thereto.

BRIEF DESCRIPTION OF THE DRAWINGS

The above and other objects and advantages of the present invention will be apparent upon consideration of the following detailed description taken in conjunction with the accompanying drawings, in which:

FIGS. 6A–6C are schematics of MRD utilizing cre/lox as a detectable marker;

DETAILED DESCRIPTION OF THE INVENTION

Figure 1:
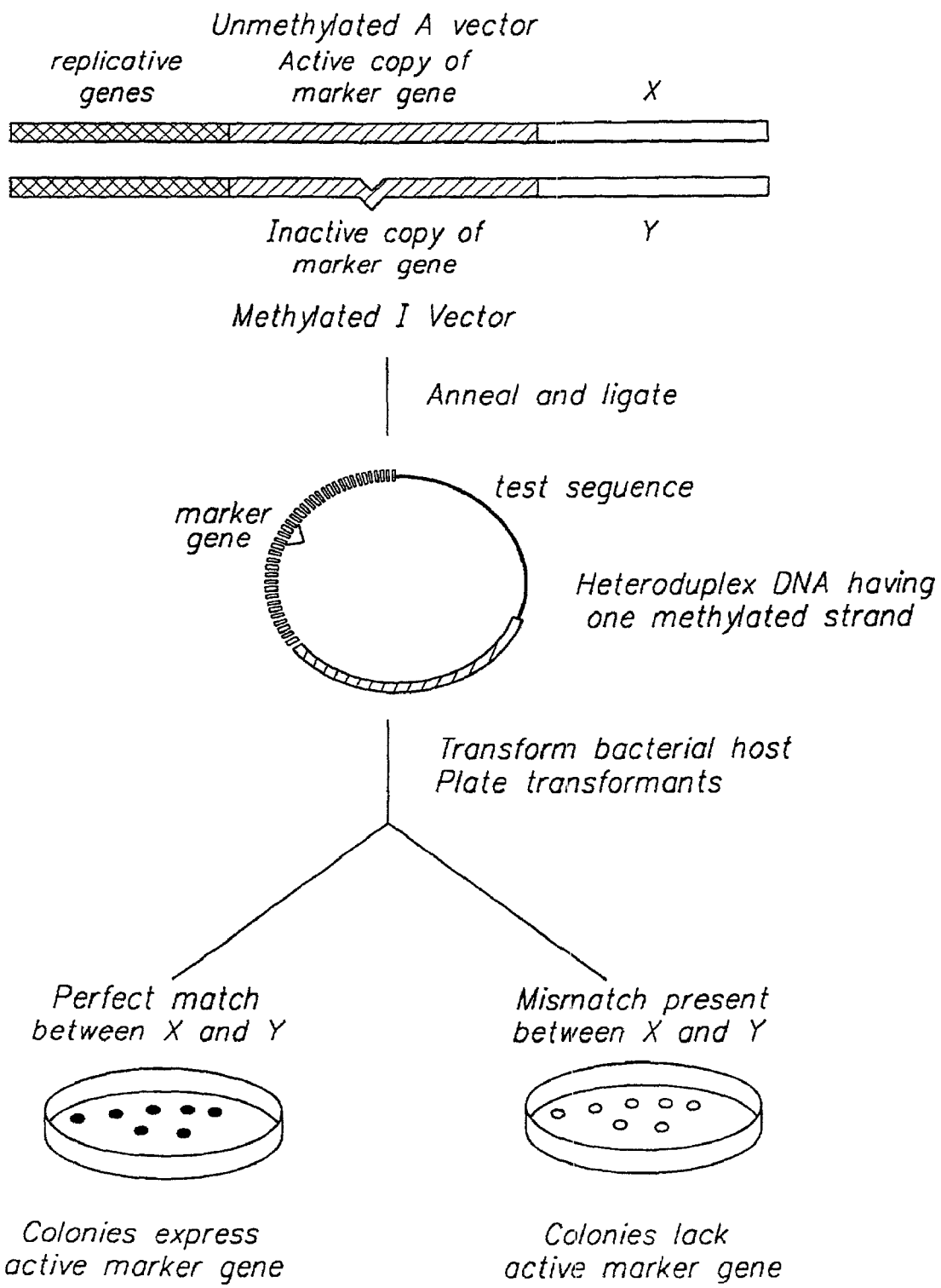
FIG. 1 depicts an embodiment of the method of the present invention for in vivo mismatch repair detection (MRD)

Mismatch Repair Detection (MRD) exploits the exquisite sensitivity and specificity of the cellular mismatch repair machinery to provide a rapid, sensitive, and readily multiplexed in vivo method for detecting mismatches in nucleic acid duplexes. Where one strand of the duplex has a known sequence, MRD can be used rapidly to identify nucleic acids that differ from such standard, even by a single nucleotide.

MRD exploits two phenomena of the cellular mismatch repair machinery that are particularly well described for the dam-directed mismatch repair system of E. coli: the first is the ability of a correctable mismatch in a heteroduplexed DNA sequence to initiate "co-repair" of a mismatch, located elsewhere in the heteroduplexed molecule, that cannot itself initiate such repair; the second is the directionality of the initiated strand correction.

MRD reports a mismatch in a DNA "test" duplex by its ability, when included within a replicable vector, to initiate in vivo corepair of a phenotypically sortable genetic element ("marker") present elsewhere in the vector as an otherwise "uncorrectable" heteroduplex. By "phenotypically sortable" is intended a genetic element that confers upon the cell a distinguishable phenotype. Because repair of the marker mismatches is directional—that is, reproducibly in favor of the sequence of one of the two strands of the marker heteroduplex—the two strands of the marker heteroduplex can be designed so that repair confers upon the host cell a phenotype distinguishable from that obtained in the absence of repair.

And because each cell transformed with a heteroduplexed vector serves as a discrete reporter, each of a large population of host cells can be used concurrently to report the presence or absence of mismatches in a plurality of test duplexes, permitting a highly multiplexed analysis.

Methyl-Directed Mismatch Repair MRD

In a first aspect, the invention exploits the methyl-directed mismatch repair machinery of bacteria, notably Escherichia coli, to report mismatches.

In vivo, the substrate for repair by the methyl-directed mismatch repair machinery is a hemimethylated, double-stranded DNA that contains mismatches. As a general matter, the methyl-directed mismatch repair system of E. coli will detect and initiate repair of from 1–4 contiguous mismatches in such a hemimethylated heteroduplex, the mismatches representing any combination of substitutions, deletions, or insertions. In the presence of such an initiating mismatch, the strand of DNA that contains within it the modified sequence motif $GA^{methyl}TC$ is recognized by the repair system as the "correct" sequence, and a large portion (at times even the entirety) of the unmethylated strand is degraded and the methylated strand used by the cell as a template for synthesis of the second, complementary, strand.

The proteins of the methyl-directed mismatch repair system of E. coli typically do not repair loops of 5 nucleotides or more in a hemimethylated duplex, however. Such loops will, therefore, typically remain uncorrected in the absence of other mismatches. However, if repair is initiated at one site on the DNA molecule, then a region extending for at least 10 kb will be co-repaired on the molecule.

Accordingly, in this aspect of the invention, a DNA "test" duplex is included in a hemimethylated replicable vector that further includes a marker heteroduplex. The marker heteroduplex contains at least one loop of five or more contiguous nucleotides that differ between the two strands; the marker heteroduplex excludes sequence differences of 1–4 contiguous nucleotides. The marker heteroduplex thus cannot itself initiate repair when the vector is introduced into a bacterial host cell having an active methyl-directed mismatch repair system. However, corepair of the marker, with attendant phenotypic change, can be initiated by any sequence differences of fewer than 5 contiguous nucleotides present within the test duplex portion of the vector.

The replicable vector ("test vector") used to report the presence or absence of mismatches is usefully described as having four discrete parts—a first vector that contributes a first marker strand, a second vector that contributes a second marker strand, a first test sequence strand, and a second test sequence strand—although the vector need not necessarily be constructed by physical assembly of four discrete components.

As noted above, the first and second marker strands differ in sequence. In the absence of mismatch repair initiated in the test duplex, each of the strands will serve as a template for semiconservative replication, thus producing two distinct vector species within the cell after a single round of vector replication. The phenotype conferred on the cell by the concurrent presence of the two marker forms will be dictated by whichever of the forms encodes a dominant marker phenotype. Where mismatch repair precedes vector replication, only one of the two marker forms will be present in the vector pool within the cell, with the phenotype dictated by the strand that acts as template for repair. Typically, the nondominant marker phenotype is chosen to be encoded on the methylated strand: in such case, repair initiated by a mismatch in the test duplex will create cells having the nondominant phenotype, which can readily be distinguished from the dominant phenotype exhibited by cells that, lacking an initiating mismatch, possess vectors respectively expressing each of the two forms of the marker.

In one embodiment particularly well suited to illustration, the "dominant" marker phenotype is an "active" marker; that is, a marker that, when expressed, is dominant in effect over an "inactive" form. For purposes of discussion, therefore, any such dominant form of the marker is herein termed the "A" form (for "a"ctive), although other types of phenotypic dominance are not intended thereby to be excluded, and the vector contributing the dominant form of the marker is referred to as the "A" vector, or the "standard". Analogously, for purposes of discussion any such nondominant ("recessive") form of the marker is herein termed the "I" form (for "i"nactive), although other types of phenotypic nondominance are not intended thereby to be excluded, and the vector contributing the nondominant form of the marker is referred to as the "I" vector.

The detectable marker gene can be any gene expressed in the host cell that provides a directly or indirectly detectable characteristic; that is, that confers a detectable phenotype upon the host cell. Exemplary phenotypes include change in color, fluorescence, antibiotic resistance and/or sensitivity, luminescence (e.g., by expression of luciferase), etc.

For example, experimental Example 1 herein below demonstrates the utility and convenience of the LacZα gene as a calorimetric marker to be used in the replicable vectors of the present invention.

In its "active" form, the LacZα gene product encodes an active betagalactosidase, readily detectable calorimetrically when the cells are induced with isopropyl-β-D-thiogalactoside (IPTG). A five basepair insertion into the LacZα gene eliminates or substantially reduces enzymatic activity. Bacteria containing the active form are blue when grown on media supplemented with both IPTG and the chromogenic enzyme substrate 5-bromo-4 chloro-3-indolyl-β-D-galactoside (X-Gal) and red when grown on IPTG-supplemented MacConkey agar; on either medium, bacteria having the inactive form of the LacZα gene are white.

It will be understood by one of skill in the art that this type of qualitative analysis is merely a convenience, and is not essential to the practice of the invention. Methods of quantitative analysis, e.g. ELISA, RIA, etc., that can distinguish between the amount of marker produced by one active gene and the amount of marker produced by two active genes (or multiples thereof) may also be used. Such quantitative methods permit cells having only active marker to be distinguished from cells having a mixture of active and inactive marker, and permit cells having only inactive marker to be distinguished from cells having a mixture of active and inactive marker.

Indeed, a wide variety of assays for betagalactosidase activity—calorimetric, fluorescent, and luminescent—are known, and can readily be used. For example, o-nitrophenyl-β-D-galactopyranoside (ONPG) and chlorophenol red β-d-galactopyranoside are conveniently used as substrates for spectrophotometric (calorimetric) detection, typically in liquid medium. Fluorescein di-β-D-galactopyranoside ("FDG", "fluorescein digalactoside", catalogue no. F-1179, Molecular Probes, Inc., Eugene, Oreg., USA) is a sensitive substrate for detecting β-galactosidase fluorescently. Fluorescence-based assays employing FDG are reported to be 100- to 1000-fold more sensitive than radioisotope-based ELISAs. A chemiluminescent substrate for betagalactosidase (Roche, Galacton™ Plus β-gal substrate) is also available commercially.

Although the marker heteroduplex is conveniently described as having an active and an inactive form encoded on opposing strands, the active form being dominant in phenotype over the inactive form, the only functional requirement is that the two forms of the marker gene product confer distinguishable phenotypes upon the host cell. Thus, the invention further comprises, in other embodiments, markers in which an inactive allele is dominant over the active allele ("dominant negative").

An example of a gene where dominant negative alleles have been described is the lac repressor, encoded by the LacI gene. See, e.g., Betz, "Cloning and characterization of several dominant-negative and tight-binding mutants of lac repressor," *Gene* 42(3):283–92 (1986); Betz et al., "Effects of dominant-negative lac repressor mutations on operator specificity and protein stability," *Gene* 67(2):147–58 (1988). Deletions that produce a dominant negative allele are likely to be in frame (e.g., 6 bp or 9 bp deletions).

A deletion in LacI that creates a dominant negative allele ID can be used as the marker gene in an MRD assay where the inactive marker is presented on the unmethylated vector strand, to be eliminated by corepair initiated by a sequence variation in the test duplex.

The LacI function can be monitored by placing one or more genes under control of the Lac operator. For example, genes conferring tetracycline resistance and streptomycin sensitivity can be placed under LacI control, using the same promoter or two different promoters. If no variation is present, both LacI$^+$ and LacI$_D$ are present, allowing the expression of the antibiotic cassette, conferring a streptomycin sensitive, tetracycline resistant phenotype. On the other hand, in the presence of a variation, the LacI$_d$ allele is removed, leaving the cell with only LacI$^+$, inhibiting expression of the antibiotic cassette and conferring a streptomycin resistant, tetracycline sensitive, phenotype.

As another example, the marker can encode a gene product that is detectable fluorescently, rather than calorimetrically.

For example, the marker can encode the substrate-independent, intrinsically fluorescent green fluorescent protein from *Aequorea victoria* ("GFP"), proteins related thereto, such as DsRed (Matz et al., *Nature Biotechnol.* 17:969–973 (1999)), or derivatives thereof (collectively, "GFP-like chromophores). These GFP-like chromophores share the property of intrinsic fluorescence; that is, the GFP-like chromophore is entirely encoded by its amino acid sequence and can fluoresce without requirement for cofactor or substrate. For review, see Chalfie et al. (eds.), *Green Fluorescent Protein: Properties, Applications and Protocols,* Wiley-Liss, New York (ISBN:0-471-17839-X), 1998; Conn (ed.),

*Green Fluorescent Protein,* Methods in Enzymology vol. 302, Academic Press, San Diego (ISBN: 0-12-182203-6), 1999.

The GFP-like chromophores comprise an 11-stranded β-barrel (β-can) with a central a-helix, the central a-helix having a conjugated π-resonance system that includes two aromatic ring systems and the bridge between them. Insertions within the central α-helix can destroy the protein's fluorescence, permitting active forms to be discriminated from inactive forms by the intrinsic fluorescence, or lack thereof, of the bacterial host cell.

Although the marker heteroduplex is conveniently described as having an active and an inactive form encoded on opposing strands, the only functional requirement is that the two forms of the marker gene product confer distinguishable phenotypes upon the host cell.

To use GFP-like chromophores as an example, the A and I forms of the marker can encode GFP-like chromophores that differ detectably in excitation and/or emission spectra.

A wide variety of such distinguishable GFP-like chromophores exist. The GFP-like chromophore can be selected from GFP-like chromophores found in naturally occurring proteins, such as *A. victoria* GFP (GenBank accession number AAA27721), *Renilla reniformis* GFP, FP583 (GenBank accession no. AF168419) (DsRed), FP593 (AF272711), FP483 (AF168420), FP484 (AF168424), FP595 (AF246709), FP486 (AF168421), FP538 (AF168423), and FP506 (AF168422).

Alternatively, the GFP-like chromophore can be selected from GFP-like chromophores modified from those found in nature. Typically, such modifications are made to improve recombinant production in heterologous expression systems (with or without change in protein sequence), to alter the excitation and/or emission spectra of the native protein, to facilitate purification, to facilitate or as a consequence of cloning, or are a fortuitous consequence of research investigation. Furthermore, the GFP-like chromophore need include only so much of the protein as is needed to retain the chromophore's intrinsic fluorescence. Methods for determining the minimal domain required for fluorescence are known in the art (Li et al., *J. Biol. Chem.* 272:28545–28549 (1997)).

For example, EGFP ("enhanced GFP"), Cormack et al., *Gene* 173:33–38 (1996); U.S. Pat. Nos. 6,090,919 and 5,804,387, is a red-shifted, human codon-optimized variant of GFP that has been engineered for brighter fluorescence, higher expression in mammalian cells, and for an excitation spectrum optimized for use in flow cytometers. A variety of EGFP vectors, both plasmid and viral, are available commercially (Clontech Labs, Palo Alto, Calif., USA), including vectors for bacterial expression, vectors for N-terminal protein fusion expression, vectors for expression of C-terminal protein fusions, and for bicistronic expression.

Toward the other end of the emission spectrum, EBFP ("enhanced blue fluorescent protein") and BFP2 contain four amino acid substitutions that shift the emission from green to blue, enhance the brightness of fluorescence and improve solubility of the protein, Heim et al., Curr. Biol. 6:178–182 (1996); Cormack et al., Gene 173:33–38 (1996). EBFP is optimized for expression in mammalian cells whereas BFP2, which retains the original jellyfish codons, can be expressed in bacteria. The GFP-like chromophores from EBFP and BFP2 can usefully be included in the vectors of the present invention, and vectors containing these blue-shifted variants are available from Clontech Labs (Palo Alto, Calif., USA).

Analogously, EYFP ("enhanced yellow fluorescent protein"), also available from Clontech Labs, contains four amino acid substitutions, different from EBFP, Ormö et al., *Science* 273:1392–1395 (1996), that shift the emission from green to yellowish-green. Citrine, an improved yellow fluorescent protein mutant, is described in Heikal et al., *Proc. Natl. Acad. Sci. USA* 97:11996–12001 (2000). ECFP ("enhanced cyan fluorescent protein") (Clontech Labs, Palo Alto, Calif., USA) contains six amino acid substitutions, one of which shifts the emission spectrum from green to cyan. Heim et al., *Curr. Biol.* 6:178–182 (1996); Miyawaki et al., *Nature* 388:882–887 (1997). The GFP-like chromophore of each of these GFP variants can usefully be used.

The GFP-like chromophore can also be drawn from other modified GFPs, including those described in U.S. Pat. Nos. 6,124,128; 6,096,865; 6,090,919; 6,066,476; 6,054,321; 6,027,881; 5,968,750; 5,874,304; 5,804,387; 5,777,079; 5,741,668; and 5,625,048, the disclosures of which are incorporated herein by reference in their entireties.

The methods for engineering such modified GFP-like chromophores and testing them for fluorescence activity, both alone and as part of protein fusions, are well-known in the art. Early results of these efforts are reviewed in Heim et al., *Curr. Biol.* 6:178–182 (1996), incorporated herein by reference in its entirety; a more recent review, with tabulation of useful mutations, is found in Palm et al., "Spectral Variants of Green Fluorescent Protein," in Conn (ed.), *Green Fluorescent Proteins,* Methods Enzymol. Vol. 302, pp. 378–394 (1999), incorporated herein by reference in its entirety.

Yet another phenotype of interest that can be conferred by the marker is antibiotic resistance or sensitivity.

Where bacteria are used as the mismatch repair detection (MRD) hosts, a wide variety of known antibiotic resistance and sensitivity genes can be used. A wide variety of vectors are commercially available that can serve as a source of the required resistance or sensitivity genes. Among such markers are those that confer resistance to penicillins (such as ampicillin), tetracyclines, kanamycin, zeocin, chloramphenicol, and sensitivity (or resistance) to streptomycin.

Where yeast are used as the mismatch repair detection (MRD) hosts, a wide variety of known antibiotic resistance genes can be used, as can well known auxotrophic markers.

The replicable test vector, and the first and second vectors that contribute marker strands to the test vector, can include markers, such as antibiotic resistance genes, additional to the phenotypically sortable genetic element; these additional markers are particularly useful to facilitate selection of transformed host cells.

The marker need not be directly detectable in order to confer a phenotype that can report mismatch repair.

For example, in another embodiment, the marker can be a recombinase, e.g. cre recombinase, FLP recombinase, pSR1 recombinase, etc., which is indirectly detected through its effect on a directly detectable marker.

For example, the presence of active cre may be detected by recombination between two or more heterologous recombination sites, where a directly detectable marker is present between these recombination sites. The active enzyme will recombine between the sites, thereby deleting the directly detectable marker; while in the presence of inactive enzyme, the directly detectable marker is maintained. Such directly detected markers need not be present on the test vector, and may instead be integrated into the bacterial chromosome or be resident on another episome.

Accordingly, Examples 4 and 5, below, demonstrate the use of cre recombinase as an indirectly detectable marker for MRD. As described therein, active cre acts to remove both a tetracycline resistance and a streptomycin sensitivity marker from an F' factor resident in the host bacteria, rendering the host cell tetracycline sensitive and streptomycin resistant.

The term "heterologous recombination site" is meant to encompass any introduced genetic sequence that facilitates site-specific recombination. In general, such sites facilitate recombination by interaction of a specific enzyme with two such sites. Exemplary heterologous recombination sites include, but are not necessarily limited to, lox sequences, recombination of which are mediated by Cre enzyme; frt sequences (Golic et al. (1989) *Cell* 59:499–509; O'Gorman et al. (1991) *Science* 251:1351–5; recombination mediated by the FLP recombinase), the recognition sequences for the pSR1 recombinase of *Zygosaccharomyces rouxii* (Matsuzaki et al. (1990) *J. Bacteriol.* 172:610–8), and the like.

Sequences encoding lox sites are of particular interest for use in the present invention. A lox site is a nucleotide sequence at which the gene product of the cre gene, catalyzes site-specific recombination. A particularly preferred lox site is a loxP site. The sequence of loxP, which is 34 bp in length, is known and can be produced synthetically or can be isolated from bacteriophage P1 by methods known in the art (see, e.g. Hoess et al. (1982) *Proc. Natl. Acad. Sci. USA* 79:3398). The loxP site is composed of two 13 bp inverted repeats separated by an 8 bp spacer region. The nucleotide sequences of the insert repeats and the spacer region of loxP are as follows:

SEQ ID NO:1 ATAACTTCGTATA ATGTATGC TATACGAAGTTAT

Other suitable lox sites include loxB, loxL, and loxR, which can be isolated from *E. coli* (Hoess et al. (1982) *Proc. Natl. Acad. Sci. USA* 22:3398). The nucleotide sequences of the insert repeats and the spacer region of loxC2 are as follows:

SEQ ID NO:2 ACAACTTCGTATA ATGTATGC TATACGAAGTTAT

The heterologous recombination sites useful in the present invention can be either a naturally-occurring sequence or a modified sequence. For example, PCT published application no. WO 93/19172 describes phage vectors in which the VH10 genes are flanked by two loxP sites, one of which is a mutant loxP site. Lox sites can also be produced by a variety of synthetic techniques which are known in the art. For example, synthetic techniques for producing lox sites are disclosed by Ogilvie et al. (1981) *Science,* 210: 270.

Other examples of indirectly detected markers include regulatory factors, e.g. a repressor in a strain constructed to carry one or more genes that are regulated by the specific repressor.

For example, the Lac repressor can be used to repress expression of transcriptional units that include the Lac operator. See, e.g., Carraway et al., *J. Bacteriol.* 175(13): 3972–3980. As another example, derivatives of the Tet repressor protein (TetR) can be used to inhibit or drive expression from promoters have tetracycline response elements derived from the Tn10 tetracycline-resistance operon tet operator sequence. See, e.g., Gossen et al., *Proc. Natl. Acad. Sci. USA* 89(12):5547–51 (1992); Gossen et al., *Science* 268(5218):1766–9 (1995); vectors are available commercially that contain the required repressor and response elements (Clontech Labs., Palo Alto, Calif. USA).

Yet another example of a gene that can have indirect effect on one or more directly detected markers is the amber suppressor supF (or ochre, or opal suppressor).

With the exception of the "uncorrectable" difference in the sequence of the marker gene, the "A" and the "I" vectors (or those portions of the "A" and "I" vectors that contribute to the final replicable test vector) are substantially the same in sequence.

By "substantially the same in sequence" is intended a degree of sequence similarity that permits heteroduplexes to be formed between strands of "A" and "I" vectors under standard in vitro conditions, such as in the presence of 6×SSC at 42° C.–65° C., and that excludes the presence of sequence differences that will initiate mismatch repair.

In addition to the marker gene, each of the "A" and "I" vectors has an origin of replication that is active in a bacterial host with an active methyl mismatch repair system (MMR host). The origin may provide for a high or low copy number of the vector. Optionally, the vectors will include, in addition to the phenotypically sortable genetic element, at least one gene encoding a selectable marker, such as antibiotic resistance or genes or operons that complement a metabolic defect of the MMR host, or resistance to phage infection, etc. Phage vectors may include packaging signals, genes encoding phage coat proteins and regulatory genes, etc. Desirably, the vector will contain a polylinker having a number of sites for restriction endonucleases to facilitate cloning.

Conveniently, the "A" and "I" vectors can be phagemid vectors: i.e., plasmids that contain phage sequences (typically an f1 origin) sufficient to permit rescue of single strands by infection with helper phage. In the experimental Examples set forth herein below, the "A" and "I" vectors are derived from pUC19. A wide variety of other phagemids are available commercially. (e.g., pBK and pBLUESCRIPT-II phagemid vectors, Stratagene, La Jolla, Calif., USA; pGEM®-3Zf series, Promega, Madison, Wis., USA).

In such vectors, the (+) strand can be obtained by rescue with helper phage, such as R408 (catalogue #2291, Promega, Madison, Wis., USA) or M13K07 (Catalogue #N0315S, New England Biolabs, Beverley, Mass., USA). The opposing strand can be obtained by reversing the direction of the phage origin; most commercial vectors are provided in two forms, differing only in the directional orientation of the f1 origin. Alternatively, the opposing (−) strand can be obtained by first obtaining double stranded DNA (RF form) from infected cells, and the (−) strand can be isolated from the double stranded form by various strand separation methods known in the art, e.g. columns, gels.

The vectors will contain at least one methylation recognition sequence, generally GATC; more usually, multiple recognition sequences will be present. Many vectors are known in the art and are commercially available that can serve as the requisite starting material for constructing "A" and "I" vectors.

The replicable vector ("test vector") used to report the presence or absence of mismatches also includes a duplex ("test duplex", "test sequence") comprising a first test sequence strand and a second test sequence strand.

The test sequence is a double stranded DNA molecule comprising the sequence of interest which is being tested for mismatches. A mismatch in the test sequence will initiate repair of the loop in the marker gene in the MRD host cell. Each strand of the test sequence is contributed by a different source, for convenience herein termed "X" and "Y" strands.

"X" and "Y" strands are substantially complementary. By "substantially complementary" is intended a degree of sequence similarity that permits "X" and "Y" to anneal to one another under standard in vitro conditions, such as in the presence of 6×SSC at 42° C.–65° C.

When the "X" and "Y" strands of the test sequence are perfectly complementary, then MRD host cells transformed with the test vector will not initiate correction of the loop in the marker gene, and will express a mixture of the active and inactive marker. If "X" and "Y" are mismatched, then repair is initiated. In the exemplary embodiment with active and inactive markers, the marker gene will be "corrected" by co-repair, so that both strands will have the inactive marker sequence. Transformed bacteria will therefore lack active marker.

Generally, the test sequence will have at least about 90% identity between the two strands. Generally, the sources of the "X" and "Y" strands will be closely related, e.g. individuals of a single species, individuals of closely related species, germline and somatic tissue from a single individual, inbred strains of a species, etc. The test sequence may be derived from any source, e.g. prokaryotic or eukaryotic, plant, mammal, insect, etc. The subject method is particularly useful for the analysis of complex genomes, such as those found in higher plants and animals. The test DNA sequence will usually be of at least about 20 nt in length, and usually not more than about 104 nt in length. The upper limit on length is determined by the ability of the MMR host to co-repair the strand.

Various methods may be used to generate the "X" and "Y" strands. Methods for isolating and amplifying DNA sequences are known in the art. "X" and "Y" may be cDNA from a reverse transcriptase reaction, a restriction fragment from a genome, plasmid, YAC, BAC, virus, etc.; an amplification product from polymerase chain reaction (PCR), etc. An important limitation to the use of PCR products is the choice of thermostable polymerase. Polymerases having a 3' to 5' exonuclease activity, e.g. proofreading function, are preferred. Useful thermostable polymerases with proofreading capability that are known in the art include those isolated from *Thermococcus litoralis, Pyrococcus furiosis,* and *Thermus thermophilus*. Commercially available *Thermus aquaticus* polymerase has been found to introduce a significant number of errors into the amplified DNA, and will generally be unsuitable for all but very short, e.g. less than about 500 nt, sequences.

Other amplification methods, additional to PCR, are known in the art, including various types of isothermal amplification approaches. See, e.g., Zhang et al., *Mol. Diagn.* 6(2):141–50 (2001); Nuovo, *Diagn. Mol. Pathol.* 9(4):195–202 (2000); Hall et al., *Proc. Natl. Acad. Sci. USA* 97(15):8272–7(2000); U.S. Pat. Nos. 5,854,033, 6,183,960, 6,221,603.

Where the test sequence is obtained from an in vitro amplification reaction, it may be desirable to methylate the amplification product, using conventional enzymes and methodologies.

A number of techniques are known in the art for isolating single strands, or for denaturing double stranded DNA.

For example, a reverse transcriptase product (first strand cDNA) may be treated with ribonuclease to leave only the cDNA strand. Strand separation gels are known in the art and may be used to separate the two strands of a DNA molecule. PCR may be performed with one primer conjugated to a molecule with a binding partner, such as biotin, haptens, etc. The PCR reaction is then denatured, and bound to a solid substrate conjugated to the binding partner, e.g. avidin, specific antibody for the hapten, etc. In such cases, PCR is often practiced asymmetrically, with the conjugated primer (such as a biotinylated primer) present in high molar excess over the opposing primer. The test DNA may be replicated as a single stranded entity, e.g. M13 phage, phagemid, etc. The "X" and/or "Y" sequence may be restriction fragments, PCR products, or other double stranded DNA molecules that are denatured according to conventional methods. International application PCT/US93/10722 describes one method for generating heteroduplex DNA suitable for mismatch testing.

There are a variety of methods for including an "A" vector, an "I" vector, an "X" test strand and a "Y" test strand in a single replicable test vector.

In one approach, the "A" vector and the "I" vector are propagated separately from the "X" and "Y" strands of the test duplex, and then combined therewith.

One of the two vectors (typically the vector conferring a dominant phenotype, the "A" vector) will be replicated under conditions that do not methylate adenine at the GATC recognition site, whereas the other (typically the "I" vector) will be modified to have methylated adenine at these sites. This is done so that during co-repair, the marker gene will be converted to the inactive (nondominant) form. For a number of markers, the active gene is dominant over the inactive. For example, a transformant containing one active antibiotic resistance gene and one inactive gene will be able to grow under selective conditions. Under these same conditions, one can easily distinguish inactive marker from mixed active/inactive.

The "I" vector, which is to be methylated on the adenine of the GATC recognition site, can be replicated in most common laboratory strains of *E. coli*. Other bacterial hosts that modify DNA at this site may also be used for preparing the "I" vector DNA. Generally, DNA replicated in non-bacterial cells will require an additional ex vivo methylation step, using purified DNA methylases. Substantially all of the GATC sites in the "I" vector will be methylated.

The other vector, typically the "A" vector, must be replicated in a host that lacks this DNA modification system. Suitable *E. coil* dam$^-$ strains include JM110, described in Janisch-Perron (1985) Gene 33:103–119, and SCS110 (Stratagene, La Jolla, Calif., USA). "A" vectors replicated in non-bacterial host cells, e.g. yeast, mammalian cell culture, etc. can also be used.

The separately propagated "A" and "I" vectors are then heteroduplexed before addition of the similarly heteroduplexed ("X"/"Y") test sequence.

In one embodiment of this approach, the "A" vector and "I" vector are independently replicated as double stranded DNA. The vectors are linearized, typically by restriction endonuclease digestion, and then denatured to form single strands, which are thereafter annealed to form heteroduplexes.

In such approach, it is desirable to remove the homoduplex "A"/"A" and "I"/"I" vectors after annealing. One convenient method of performing this step takes advantage of the differential methylation of the two vectors. Restriction enzymes are known in the art that will cleave homoduplex unmethylated DNA, e.g. MboI, and homoduplex methylated DNA, e.g. DpnI, but that will not cleave heteroduplex DNA having one methylated and one unmethylated strand. The double stranded "A" and "I" vectors are denatured, combined, and reannealed, leaving a mixture of homoduplex DNA ("A"/"A" vector, "I" vector) and heteroduplex DNA ("A"/"I" vector). The mixture is then treated with the methyl specific restriction enzymes. The homoduplex DNA is cleaved, and the heteroduplex is not. The heteroduplex DNA is then used in subsequent steps of the method.

In this embodiment, the double stranded heteroduplex "A"/"I" vector is then ligated to double stranded heteroduplex "X"/"Y" test DNA, which is hemimethylated, to form the complete tested vector.

The "X" and "Y" strands can be heteroduplexed using methods similar to those used to heteroduplex the "A" and "I" vectors.

It is convenient to have a short, complementary overhang on the termini of the "X"/"Y" and the "A"/"I" molecules, such as those formed by digestion with various restriction endonucleases or by the ligation of specific linkers to the termini, where the vector and the test sequence will anneal to each other. Preferably, a different overhang will be present on each terminus of one molecule, so as to prevent self-circularization of the vector. Blunt ends may also be used, in which case it may be desirable to phosphatase treat the vector ends to reduce self-circularization.

The annealed, heteroduplex DNA is circularized by a ligation reaction, using any suitable ligase, e.g. T4, E. coli, etc., using conventional buffers and conditions. Generally, the quantity of heteroduplex DNA formed will be sufficient to detect in a standard transformation reaction, e.g. at least about 0.1 picograms of DNA.

In an alternative approach to including an "A" vector, an "I" vector, an "X" test strand and a "Y" test strand in a single replicable test vector, one or both of the "X" and "Y" strands of the test duplex can be ligated respectively to the "A" and "I" vectors prior to the previously described heteroduplexing step, and the chimeric DNA strand(s) then used to form the heteroduplex test vector.

In such an approach, the "X" and/or "Y" sequences can be separately cloned into the "A" and "I" vectors, using conventional recombinant DNA methods (see Sambrook et al., supra.). Either strand can go into either vector. The chimeric molecules can then be replicated as previously described, to provide methylated and unmethylated strands.

In one embodiment, schematized in FIG. 1, each of "X" and "Y" test sequences is cloned into a vector. As shown, "X" is cloned into the "A" vector and propagated in a methylase-deficient host to produce an unmethylated "AX" chimera. As shown, "Y" is cloned into the "I" vector and propagated in a dam$^+$ host to produce methylated "IY" vector. Each of the vectors is linearized, the two linear vectors annealed to create a double-stranded heteroduplex "AX"/"IY", which is then ligated to create a double-stranded, hemimethylated, closed circular test vector.

In a useful method, test DNA from only one source (e.g., "X") is cloned into the "A" or "I" vector to form a chimeric molecule. While either the "I" vector or the "A" vector may be such a chimera, conveniently the "A" vector will contain a copy of the test sequence. Such "A" vector may be referred to as a "standard" vector, since mismatches reported by MRD will be those that differ from this standard.

As further described below, a single standard may be used in a reaction, or multiplex reactions may be performed in which a plurality of standards, each comprising a distinct test sequence, are hybridized in a single reaction. The multiplex reaction may combine two or more standards, usually at least about 10 standards, more usually at least about 25, 50, 100, 500, or 1,000 standards, and even as many as 2,000, 3,000, 4,000, 5,000, 6,000, 7,000, 8,000, 9,000, 10,000 or even 100,000 standards.

The "AX" chimeric standard is then usefully rendered single stranded, although double-stranded chimeric standards can also be used. The chimeric standard can be rendered single stranded, e.g., by restriction digest and denaturation. Typically, however, the "A" vector includes a phage origin, permitting phage-induced rescue and packaging of one of the two strands of the chimeric vector. As is known in the art, the strand that is packaged by phage rescue will be determined by the direction of the phage origin in the "A" vector.

Figure 2:
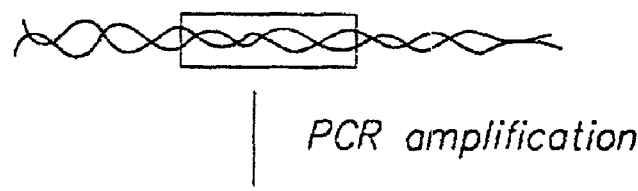
FIG. 2 depicts the method of FIG. 1 using single or double stranded vectors and an amplification product as a test sequence.
Figure 2:
Figure 2:
Figure 2:
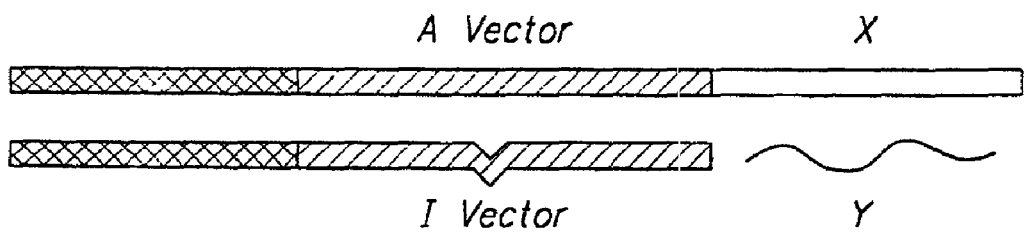

As schematized in FIG. 2, single stranded standard vector ("AX") can then be combined in a single hybridization reaction with (i) linearized, typically double-stranded, "I" vector, and (ii) linearized, typically double-stranded, "Y" test sequence ("Y" may be denatured double stranded DNA, e.g. a PCR product, fragment of genomic DNA, etc., or may be single stranded, e.g. cDNA, etc.). Any double-stranded molecules are denatured, typically by addition of base (or alternatively, or in addition, by heating well above the Tm of the duplexes), either before or after addition to the mix; conditions are then adjusted to permit duplex formation.

As an example, single-stranded standard ("AX") DNA can be obtained by transforming the "AX" vector into a dam$^-$ strain such as SCS110 (Stratagene), and then rescuing unmethylated single strand using helper phage, such as M13K07 (New England Biolabs, MA, USA). Optionally, double-stranded contamination can then be removed using MboI (or, alternatively, ScrFI). "I" vector, propagated in a dam$^+$ strain, is linearized using a restriction enzyme that cuts once in the "I" vector. The "Y" homoduplex can be provided by PCR performed using a proofreading polymerase, such as pfu polymerase; the PCR product, optionally purified, can then be phosphorylated and methylated in vitro, with methylation performed, e.g., using dam methylase (New England Biolabs) at 37° C. for 1–2 hours. After annealing, nicks in the desired heteroduplex can be sealed using a nick-specific ligase, such as Taq DNA ligase. Optionally, nicked heteroduplexes, "Y"/"Y" homoduplexes, and single-stranded "AX" vector can be removed before transformation.

An advantage of this latter approach to including an "A" vector, an "I" vector, an "X" test strand and a "Y" test strand in a single replicable test vector is that a large quantity of "I" vector can be prepared for subsequent use with any test duplex. Furthermore, this approach permits the "AX" standard to be prepared in bulk, and then used to query DNA from a wide variety of sources for the presence of mismatches at the "X" locus.

The test vector, comprising "A" vector, "I" vector, "X" test sequence strand, and "Y" test sequence strand, is transformed into a suitable host.

Most bacterial species have an active methyl mismatch repair system, and can therefore be used as an MMR host in this aspect of the invention. Suitable species include E. coli and other gram negative rods, such as Pseudomonas, Erwinia, Shigella, Salmonella, Proteus, Klebsiella, Enterobacter and Yersinia. Other species of interest include B. subtilis, Streptomyces, etc. The genetics and growth requirements of E. coli are well known, and in most cases it will be the preferred host. Transformation techniques are well known, for example see Hanahan (1985) in: DNA Cloning, Vol. 1, ed. D. Glover, IRL Press Ltd., 109.

The transformed bacteria are generally grown under selective conditions, where only those cells able to express "A" vector-encoded selective marker can proliferate. Preferably the test vector will include a selective marker, such as antibiotic resistance, for this purpose. The transformants may be grown in a suitable culture medium, e.g. LB broth, SOB broth, 2YT, etc., as a liquid culture, or alternatively can be grown on plates. In some cases, the growth medium will also include any substrates required for development of the observable phenotype.

The determination of transformants expressing active and inactive marker is then made. The method of determination will vary with the specific marker used, as discussed above.

Transformants that lack active marker had an initiating mismatch in the test sequence. An increase in the percentage of transformants that lack active marker, compared to a control, perfectly matched test sequence, is indicative of a mismatch. The transformed bacteria that lack active marker are growing the "corrected" test vector, where both strands of vector DNA will have the sequence of the originally methylated strand. The transformed bacteria that express active marker will generally have a mixture of "A" and "I" vector. Vector DNA may be prepared from the transformants, and used for further purification and characterization.

In one embodiment, plates of transformants are counted for colonies having a positive or negative color change, such as cleavage of indolyl-β-D-galactoside to produce a blue color, or expression of luciferase. In another embodiment, replica plates are made, and it is determined whether cells from individual colonies are capable of growing in a selective medium. Transformants grown in liquid culture may by stained, for example with antibodies specific for the selectable marker, and analyzed by flow cytometry to determine the number of cells expressing active marker. Where the marker (either directly or indirectly) confers antibiotic resistance or sensitivity, the host cells can be grown in two aliquots under differing selective conditions.

The use of markers that provide for a color change may be detected by growing the transformed bacteria on medium that allows for the color change, but where the active marker is not required for growth. Transformants expressing the marker are then detectable by visual inspection, spectrophotometry, flow cytometry, etc. Another example of a directly detected marker is a gene that can be expressed on the surface of the bacterium and can therefore be detected by antibodies to it. The use of antibiotic resistance as a detectable marker, e.g. expression of β-lactamase, etc. may require duplicate plates to isolate the mismatched sequence. Alternatively, an antibiotic resistance and an antibiotic sensitivity gene may both be present. For example, the vector may contain a streptomycin sensitivity and a tetracycline resistance gene. When both active genes are present, then cells may be grown in duplicate cultures, one containing streptomycin, and the other containing tetracycline. In another example, transformants are grown under non-selective conditions, and a duplicate plate grown under selective conditions. The colonies that cannot grow in the presence of the antibiotic have a mismatched test sequence.

Multiplex Analysis

Because each cell transformed with a heteroduplexed test vector serves as a discrete mismatch reporter, each of a large population of host cells can be used concurrently to report the presence or absence of mismatches in a plurality of test duplexes, permitting highly multiplexed analyses. MRD provides the ability to perform high throughput DNA variation detection. MRD's multiplexing potential exceeds that of currently known methods, therefore offering an improvement over other methods for large scale SNP genotyping.

In one approach, a single-stranded "AX" chimeric standard is created for each of a plurality of desired sequences of different sequence. For example, a single-stranded "AX" chimeric standard can be created for each exon predicted from a eukaryotic or prokaryotic genome, or for that subset of exons known or suspected to be the site of sequence variation. Because MRD does not require expression of the test duplex, single-stranded "AX" chimeric standards can equally be prepared from noncoding regions, such as upstream transcriptional regulatory regions, that are known or suspected to be the site of sequence variation.

A plurality of such standards can then be combined with an "I" vector that will anneal commonly to all of the standards, and with a plurality of nucleic acids to be tested for sequence variation at the loci included within the plurality of standards. Typically, the nucleic acids will be derived from a single source, although the nucleic acids can also be from a pooled source.

The multiplex reaction may combine two or more standards, usually at least 5 standards, 10 standards, more usually at least 25, 50, 100, 500, or 1,000 standards, and even as many as 2,000, 3,000, 4,000, 5,000, 6,000, 7,000, 8,000, 9,000, 10,000 or even 100,000 standards, with the limit dictated only by the ability to distinguish among the test vectors.

Examples 4 and 5 set forth herein below demonstrate the multiplexing capability of MRD.

As reported in Example 4, the MRD procedure was applied to the identification of DNA sequence variation in 13 DNA fragments randomly selected from a group of published polymorphic Sequence Tagged Sites (STSs). Standards were made for each STS, and heteroduplexes were made between a mixture of the standards and DNA fragments amplified from each individual tested. Heteroduplexes were transformed en masse into the MUTATION SORTER™ (MS) strain, with the transformants divided into two aliquots that were then grown in two separate cultures, one supplemented with tetracycline and the other with streptomycin. DNA from each of the two cultures was fluorescently labeled and loaded on an Applied Biosystems (ABI) sequencing machine. Fragment peaks were analyzed and the presence or absence of variations in a particular DNA fragment assessed by determining the pool where a specific fragment was more prevalent (FIG. 7).

Figure 7:
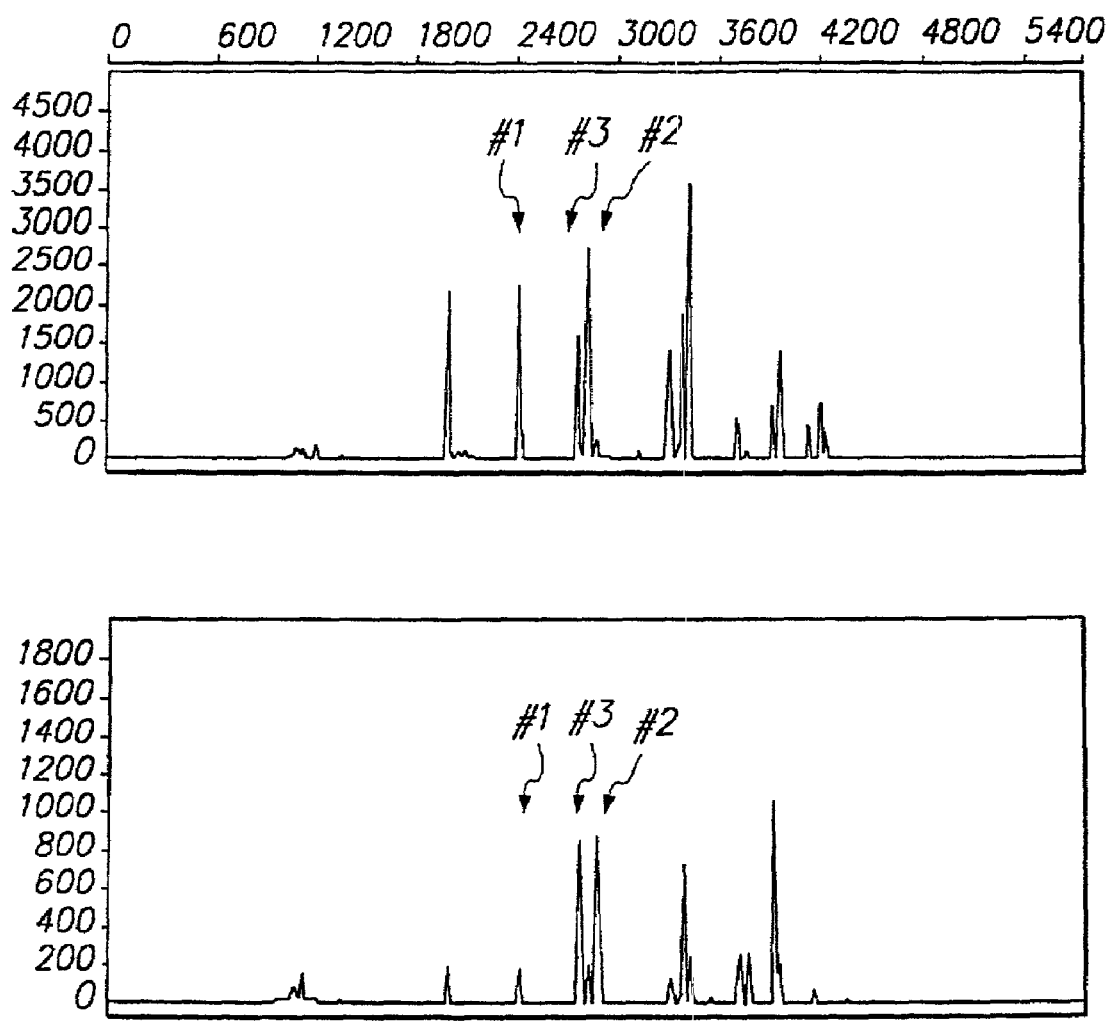
FIG. 7 is an acrylamide gel read-out of screened fragments.

Shown in FIG. 7, the two samples prepared from the cultures supplemented with streptomycin or tetracycline, respectively, have different peak traces. The traces show the different peaks corresponding to the different fragments. Each peak is quantitated automatically. Assignment of the alleles of the tested individual is determined from the relative intensity of a fragment between the two pools. The predominance of a fragment in the streptomycin pool indicates the absence of a variation. In contrast, the predominance of a fragment in the tetracycline pool indicates the presence of a variation on both alleles. Finally, the abundance of a fragment in both pools indicates the individual tested is heterozygous for the fragment. These assignments are reproducible in independent testing. The signal to noise ratio for detecting a heterozygous variation is on the order of 10:1; and the detection of homozygous variation is substantially more robust.

In Example 5, MRD's capacity for multiplexing MRD was tested by performing MRD on a pool of 32 exons of genes involved in cancer pathogenesis or progression. A panel of 32 standard plasmids were created. These plasmids were then pooled and served as a reference to compare with the test DNA. Thirty-two PCR reactions were performed in each of three independent tumor cell lines. The MRD procedure was performed with the PCR pools of each of the three tumors. After transformation, DNA was prepared from the two bacterial cultures grown in the presence of tetracycline or streptomycin. An agarose gel was run for a restriction digest that released the inserts of the DNA pools. The tetracycline pool, compared with the streptomycin pool, contained a higher proportion of variants between the standard and test DNA. We identified, in the three tumors, five such variant fragments in four distinct exons.

Figure 8:
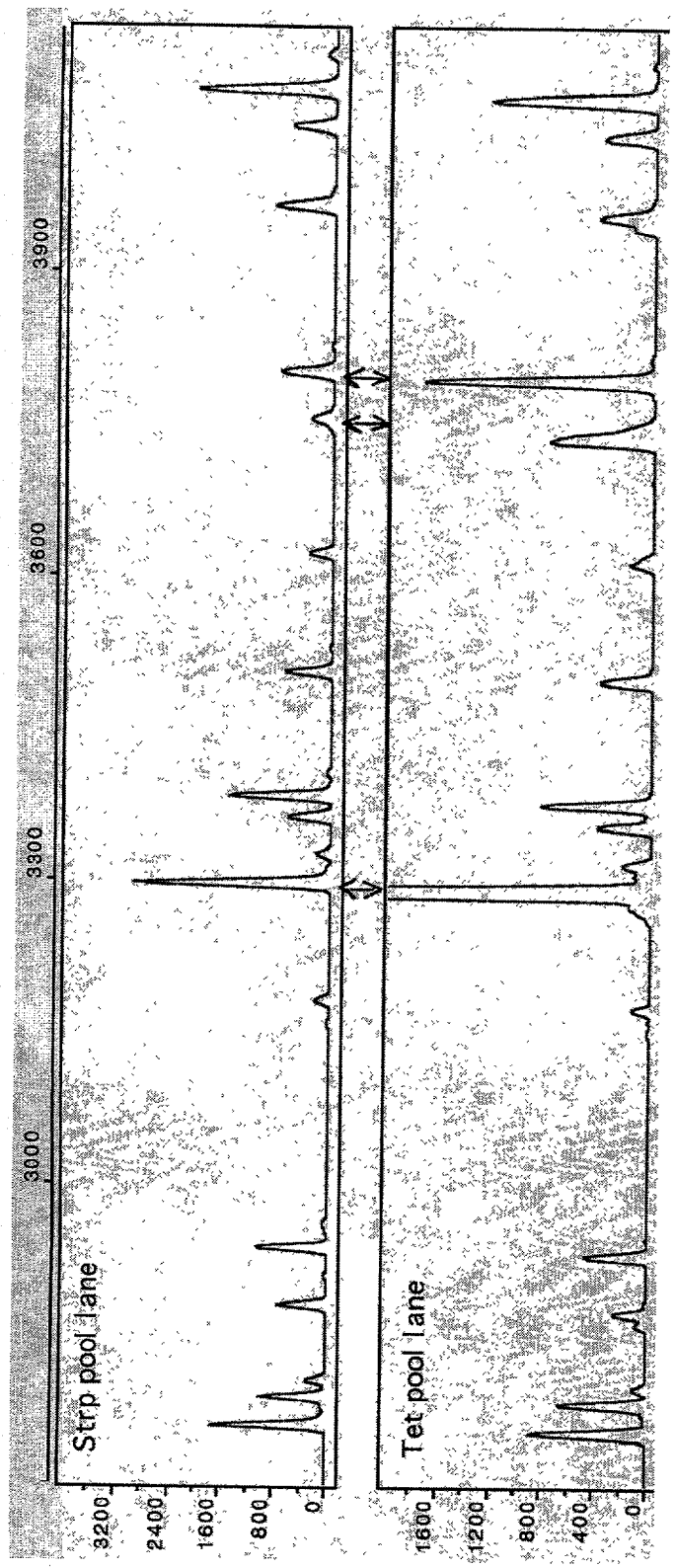
FIG. 8 is an example of a sequencing gel trace resulting from scanning 35 different fragments for variations by MRD.

FIG. 8 is an example of an ABI 377 sequencing gel trace resulting from scanning 35 different fragments for variations by MRD.

As demonstrated in Examples 4 and 5 (and shown in FIGS. 7 and 8), MRD readily permits multiplex analysis, in which the presence or absence of variation can be concurrently reported for a plurality of different standards. In effect, the host cell strain sorts fragments into two pools: those having a mismatch and those having no mismatch. The problem of DNA variation detection is then reduced to the problem of identifying the fragment content of the two pools.

In Examples 4 and 5, gel electrophoresis is used to determine the fragment content of the two pools in MRD experiments in which each of the standards has a different length. Higher levels of multiplexing require, however, methods that permit discrimination among a greater number of standards than can resolved by gel electrophoresis.

One solution, exemplified in Example 6, is to use a microarray for detection, in which each standard hybridizes to unique, addressably distinguishable, probe that is resident on the array.

Microarrays are well known in the art. As used herein, the term "microarray" and the equivalent phrase "nucleic acid microarray" refer to a substrate-bound collection of plural nucleic acids, hybridization to each of the plurality of bound nucleic acids being separately detectable. The substrate can be solid or porous, planar or non-planar, unitary or distributed. As so defined, the term "microarray" and phrase "nucleic acid microarray" include all the devices so called in Schena (ed.), DNA Microarrays: A Practical Approach (Practical Approach Series), Oxford University Press (1999) (ISBN: 0199637768); Nature Genet. 21(1)(suppl):1–60 (1999); and Schena (ed.), Microarray Biochip: Tools and Technology, Eaton Publishing Company/BioTechniques Books Division (2000) (ISBN: 1881299376), the disclosures of which are incorporated herein by reference in their entireties.

Highly Multiplexed Mismatch Repair Detection for Rare Allele Detection and Scoring MRD does not report the nature of the mismatch as between the standard and test sequences. Rather, the output is binary, reporting only whether the test sequence matches the standard, or does not. To distinguish among variants of a single standard, such as variants of a chosen exon, a plurality of standards must therefore be constructed, each having one of the alleles against which the test sequence is separately, often concurrently, to be compared.

Where only a few common alleles dominate, this approach can readily be used. Where a larger number of alleles exist, however, or where rare alleles are sought, difficulties may present.

For example, MRD's ability to use multiple standards concurrently to query a sample for sequence variation (whether such standards are multiple allelic forms of a single target locus or are instead, or in addition, drawn from a plurality of distinct loci) is limited by the requirement that such concurrently used standards be separately detectable.

Another potential impediment to efficient use of MRD to detect rare alleles is the signal:noise ratio inherent in the MRD reporter system.

For example, where mismatches are reported by a beta-galactosidase calorimetric assay, spurious cleavage of the enzymatic substrate or spontaneous reversion of the lacZ locus can contribute to a background of improperly called colonies. Even in the improved MRD reporter system in which mismatches are reported by the antibiotic resistance phenotype conferred by action of Cre recombinase on an antibiotic cassette, a finite background level is observed. If the allele to be detected occurs at a frequency less than that of the inherent background, its reliable detection will be difficult.

In another aspect, therefore, the present invention provides methods and compositions that increase the multiplexing capacity of mismatch repair detection (MRD)—that is, that increase the number of standards of distinct sequence that can concurrently be used to query a sample for the presence of sequence variation. Among other advantages, the increased multiplexing capacity permits a larger number of allelic variants to be included as standards for each locus to be queried for variation. The present invention further provides compositions and methods that increase MRD's signal:noise ratio. Individually and together, these improvements permit rare allelic variants more readily to be identified and scored.

As described above, MRD detects and reports a mismatch in a DNA "test" duplex by its ability, when included within a hemimethylated replicable vector, to initiate in vivo corepair of a "phenotypically sortable" genetic element ("marker") that is present elsewhere in the vector as an otherwise "uncorrectable" heteroduplex. Because repair of the marker mismatches is directional—that is, reproducibly in favor of the methylated strand of the marker heteroduplex—the two strands of the marker heteroduplex are engineered so that repair confers upon the host cell a phenotype distinguishable from that present in the absence of repair. Any genetic element capable of producing such a distinguishable phenotype depending upon presence or absence of repair is herein termed a "phenotypically sortable" genetic element.

And because each cell transformed with a heteroduplexed vector serves as a discrete reporter, each of a large population of host cells can be used concurrently to detect and report the presence or absence of a mismatch, permitting a multiplexed analysis. In such a multiplex analysis, the host cell strain phenotypically sorts from the collection of duplexes all those that are capable of initiating a mismatch corepair event in vivo; identification of the duplexes present within the sorted pool then serves to identify all standards as compared to which variation existed in the queried sample.

Figure 10A:
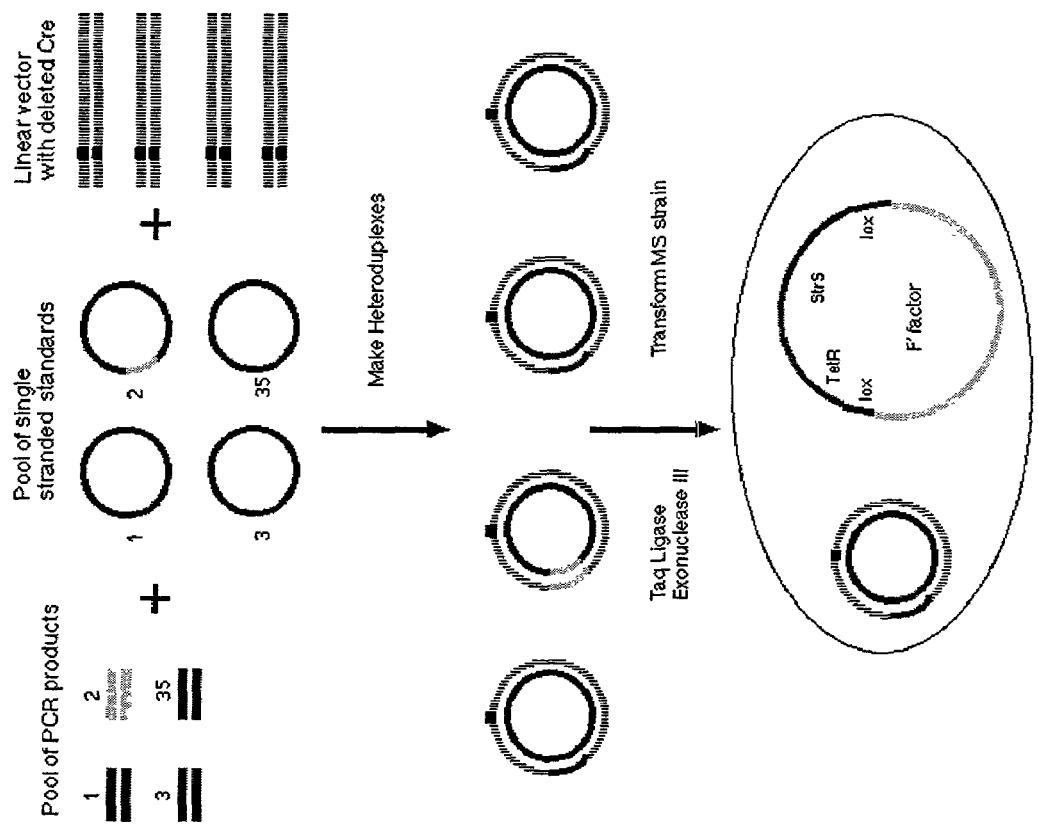
FIGS. 10A–10C schematize a preferred embodiment of mismatch repair detection (MRD) in which variation from a standard nucleic acid sequence is reported by Cre-mediated change in the antibiotic resistance and sensitivity phenotype of an E. coli host strain.
Figure 10B:
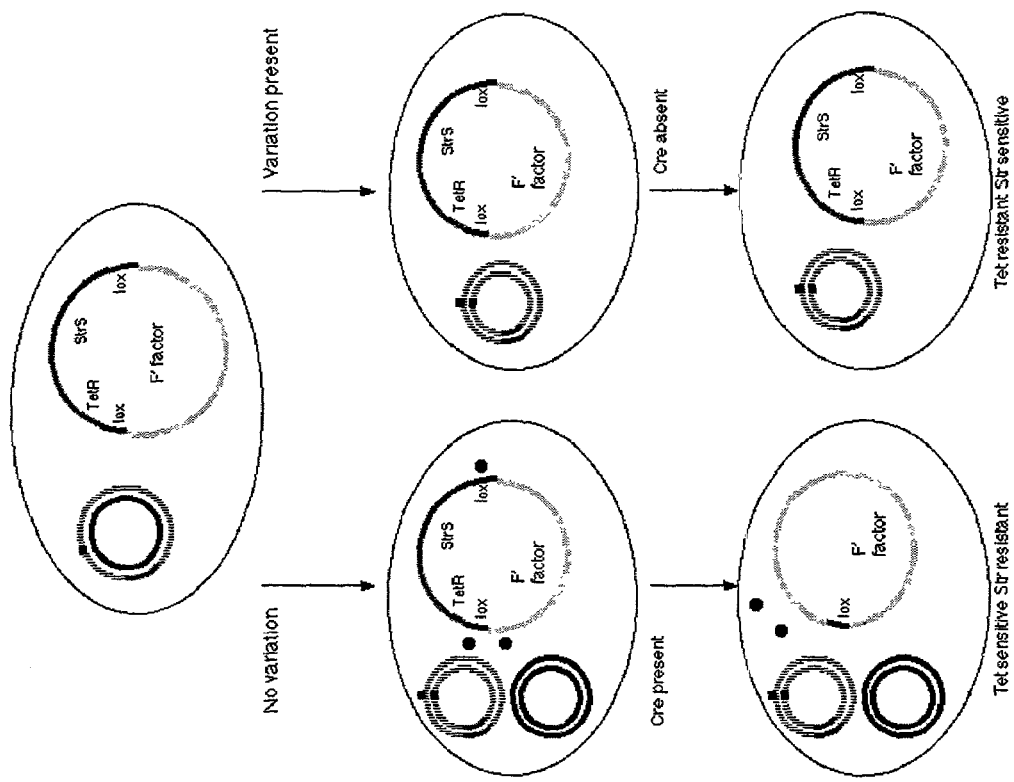
Figure 10C:
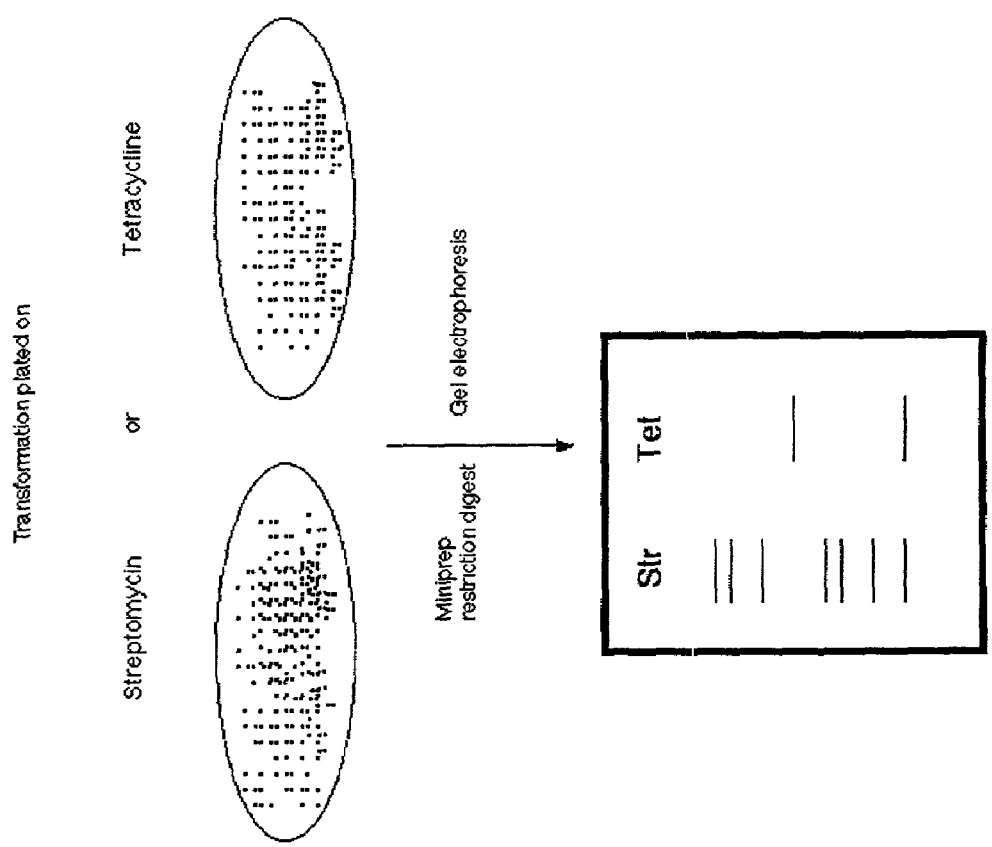

The method is further understood by reference to FIGS. 10A–10C.

At the top center of the figure is shown a pool of single-stranded, closed circular standard vectors. Each such standard vector includes a vector portion and a distinct standard sequence, which standard is to be used to query a sample for the presence of sequence variation. The standards are nonsequentially numbered in the figure to indicate that only a subset of such single stranded standards are shown.

Not shown, the vector portion of the single-stranded standard vectors further includes, inter alia, a plasmid origin of replication to permit double-stranded propagation, a filamentous phage origin to permit single-strand rescue, and the coding region for Cre recombinase, the last of which permits phenotypic sorting in the MRD process.

The single-stranded standard vectors are unmethylated, and are typically obtained by phage rescue from a double-stranded plasmid propagated in a dam strain, such as SCS110.

At the top right of the figure is shown a pool of double-stranded linearized vector, identical in sequence to the vector used to produce the single-stranded standard vectors with one exception: the linearized double stranded vectors possess a five base pair deletion in the cre recombinase coding region, a deletion that is sufficient to prevent translation of an active recombinase gene product. The linearized vector further differs from the closed circular single-stranded standard vector in its state of methylation: propagated in a dam+ strain, the linearized double-stranded vector is fully methylated at GATC methylase recognition sequences.

At the top left is indicated a pool of linearized double-stranded nucleic acids to be queried for variation in sequence at the loci included within the standards. The sample nucleic acids are methylated: where the sample pool is derived by in vitro amplification from genomic samples, as shown in FIG. 10A, the samples are methylated in vitro using dam methylase.

The sample nucleic acids, single-stranded standard vectors, and linearized double-stranded Δcre vectors are mixed, denatured, and allowed to reanneal. Among the products formed, as shown in the center of FIG. 10A, are circular heteroduplexes. The circular heteroduplexes are formed by the annealing of two separate nucleic acids to each of the single-stranded standard vectors: (i) a complementary strand of linearized, methylated, Δcre vector, which is common to all of the single-stranded standard vectors, and (ii) uniquely, a strand, drawn from the sample pool, that is complementary to the vector's distinct standard.

As shown in the middle of FIG. 10A, Taq ligase is then used to repair nicks in the circular heteroduplexes. These closed circular double-stranded replicable heteroduplex vectors are, for convenience, herein termed "MRD vectors". The MRD vectors can usefully be considered to comprise a "test duplex" (of which a first strand is contributed by the standard vector and a second strand is contributed by the sample being queried) physically linked to a "marker heteroduplex".

Linearized double-stranded DNA and single-stranded DNA products are eliminated, and the pool of MRD vectors—bearing within them a pool of test duplexes—are then transformed into a host cell strain for phenotypic sorting.

As shown in the bottom panel of FIG. 10A, the MUTATION SORTER™ host cell strain contains an F' episome that has an antibiotic cassette flanked by lox sites. The cassette includes a tetracycline resistance gene and a gene conferring sensitivity to streptomycin.

FIG. 10B depicts the two possible outcomes of the ensuing in vivo repair process.

In the absence of variation in the "test duplex", no corepair of the cre marker heteroduplex is initiated (shown on the left). After a single round of plasmid replication, two homoduplex plasmid species are thus present in the cell: one that encodes active Cre recombinase (active protein shown as dots), and one that does not. The active Cre recombinase being phenotypically dominant, recombination between lox sites on the episome is effected, the antibiotic cassette is eliminated, and the host cell is rendered tetracycline sensitive and streptomycin resistant.

Where "correctable" variation occurs within the test heteroduplex, corepair of the cre heteroduplex is initiated, with the methylated Δcre strand serving as template (shown on the right). After a single round of plasmid replication, a single homoduplex plasmid species is present within the host cell, encoding an inactive Cre recombinase. Accordingly, no recombination is effected between lox sites on the F' episome, and the result is a host cell that is tetracycline-resistant and streptomycin-sensitive.

The transformants are cultured briefly following transformation and, in the embodiment shown, the culture is split and the two aliquots respectively subjected to tetracycline or streptomycin selection, as schematized in FIG. 10C.

Selection with tetracycline sorts from the original collection of test duplexes all those that are capable of initiating a mismatch corepair event in vivo; identification of the test duplexes present in this sorted pool identifies all standards as compared to which variation existed in the queried sample.

Optionally, countervailing selection with streptomycin sorts from the original collection of test duplexes all those that are incapable of initiating a mismatch corepair event in vivo; identification of the test duplexes presented in this counter-sorted pool identifies all standards as compared to which variation was absent from the queried sample.

In FIG. 10C, identification of the standards present in each pool is based upon the prior engineering of the standards to have lengths that are distinguishable by gel electrophoresis (see FIG. 10C, bottom). Although such size discrimination is improved using automated nucleic acid sequencers, the number of standards that can simultaneously be identified is limited by the relatively low resolution of such approaches.

One solution, hybridization to a microarray that includes the standards, or specifically hybridizable portions thereof, among its immobilized probes, makes possible the simultaneous use of thousands of standards. Such approach will not, however, as readily permit the concurrent detection and discrimination of standards that are allelic variants of one another, which variants can differ by as few as one nucleotide. Nor does such microarray hybridization solve the problem of detecting allelic variants that occur in a pooled sample with frequency below the background rate.

Thus, in one aspect, the present invention solves these and other problems by providing an improved mismatch repair detection method for identifiably detecting a mismatch in any of a plurality of DNA duplexes of distinct nucleic acid sequence.

In the methods of this aspect of the invention, each nucleic acid standard is physically linked in its standard (and resulting MRD) vector to a phenotypically sortable genetic element, as has previously been described, and additionally to a genotypically detectable genetic element ("sequence tag"). The former permits in vivo phenotypic sorting according to the presence or absence of an initiating mismatch in the test duplex; the latter permits improved in vitro identification of the test duplexes so sorted.

The method comprises the steps of (1) phenotypically sorting from the plurality of distinct duplexes those capable of initiating a mismatch corepair event in vivo; and then (2) identifiably detecting duplexes present in the phenotypically sorted population, wherein detection and identification are effected by detection and identification of the at least one genotypically detectable genetic element uniquely linked to each said duplex.

The first step, phenotypically sorting duplexes according to their mismatch status, is performed according to any known MRD method, as described above. Accordingly, the first step of the instant method will not here be discussed in detail.

Although phenotypic sorting is readily practiced in E. coli and other gram negative bacteria by using hemimethylated substrates to direct the strandedness of corepair, vectors preferentially nicked on one of the two strands—such as by engineering of nonpalindromic N.BstNBI sites solely into one of the two vector strands—can also be used (see below).

After phenotypic sorting, the standards present in at least one phenotypically sorted population are identified.

To facilitate such detection, each of the plurality of standard sequences is physically linked in its respective standard (and resulting MRD) vector to at least a first genotypically detectable element (also termed "nucleic acid sequence tag", or "sequence tag"), each of the tags being unique among the plurality of sequence tags used in the MRD reaction.

The length of the sequence tag will be chosen, in part, based upon the number of standards of distinct sequence that are desired to be used concurrently in the assay and on the number of unique tags desired to be linked to each such standard, which together establish a lower limit on the number of unique tags that must be available. The tag length must further permit of sufficient combinations that this minimum can be achieved after applying desired sequence selection criteria.

The number of standards of distinct sequence that can be phenotypically sorted in a single E. coli-based MRD assay is virtually without limit, given the extraordinarily high efficiency with which bacteria can be transformed and selected; the plurality of distinct DNA duplexes to be sorted phenotypically in a single reaction can thus be as few as one, or as many as 10, 100, 1,000, 10,000, 15,000, 20,000, 25,000, 30,000, 40,000, 50,000, 75,000, or 100,000 or more.

Furthermore, detection of the sequence tags by hybridization to tag-detecting microarrays will present few limitations on the total number of standards to be included in a single reaction, since a plurality of such microarrays can be used.

The limit on the number of standards that would be desired to be included in a single MRD assay will thus typically be dictated by the availability and expected informational content of standards.

For example, WO 01/57276 describes 13,114 probes, each of which contains a single unique exon from the human genome, all of which are expressed in bone marrow. These 13,114 probes would usefully be included in a single MRD reaction intended to associate human genotypic variation with disorders of hematopoiesis. In such an effort, a tag length would be chosen to provide a minimum of 13,114 unique sequence tags after application of desired sequence selection criteria.

Analogously, WO 01/572275 describes 12,821 unique single exon probes expressed in human brain, which could usefully be used as concurrent standards in an MRD assay intended to associate genotypic variation with neurologic and psychiatric (e.g., DSM axis I) disorders; WO 01/572274 describes 9,980 unique single exon probes expressed in human heart, which could usefully be used as concurrent standards in an MRD assay intended to associate genotypic variation with heart disorders; WO 01/572273 describes 13,109 single exon probes expressed in human liver, which could usefully be used as concurrent standards in an MRD assay intended to associate genotypic variation with, inter alia, drug metabolism phenotypes. In these cases, a tag length would be chosen to provide a minimum of 12,821, 9,980, and 13,109 unique sequence tags, respectively, after application of desired sequence selection criteria.

Typically, therefore, at least about 1,000, 2,000, 3,000, 4,000, or 5,000, more typically at least about 10,000, and even 15,000, 20,000, 25,000, and even 50,000 unique sequence tags will be desired; the tag length will be chosen to provide such numbers after application of desired sequence selection criteria.

At times, however, each unique standard will be linked to a plurality of sequence tags, which will multiply the number of unique tags desired, in turn increasing the length required of the sequence tag.

Each tag additional to the first tag can add to the specificity of detection, where variation is scored only when all tags associated with a standard are identified in the phenotypically sorted pool. Alternatively, each additional tag can contribute to the sensitivity of detection, where variation is scored when any of the plurality of tags associated with a standard is identified in the phenotypically sorted pool.

The length of tag sequence will also be dictated by the stringency with which sequence selection criteria are applied, and tags thus eliminated from the pool of potential combinations.

Sequence selection criteria can usefully be designed (i) to maximize sequence differences, (ii) to retain similar hybridization properties, principally similarity in Tm, in order to facilitate simultaneous analysis on high density oligonucleotide arrays, (iii) to eliminate secondary structure, (iv) to eliminate runs of single nucleotides, and (v) to balance base composition. Any one or more of these criteria can be applied with various degrees of stringency.

For example, starting from the total number of potential 20-mers ($4^{20}=1.1\times10^{12}$) and applying all of these criteria with various stringencies, Shoemaker et al. describe sets of 51082, 9105, 2643, 853, 170 and 42 20-mers for use as sequence tags. *Nature Genetics* 14:450–456 (1996), the disclosure of which is incorporated herein by reference in its entirety.

Accordingly, the sequence tag used in the present invention is at least 15 nt in length, usually at least 16 nt, 17 nt, 18 nt, 19 nt, and 20 nt in length or more, and can be at least 21 nt, 22 nt, 23 nt, 24 nt, 25 nt, even 30 nt or more in length. Typically, the sequence tag is less than 75 nt in length, often less than 50 nt in length, frequently less than 40 nt in length.

The tag sequence can be directly adjacent to the standard sequence in the standard and MRD vectors.

Where the standard is obtained by amplification directly from native nucleic acids—genomic DNA, cDNA, mRNA—the tag sequence will often be so positioned, a result of having included the tag sequence directly 5' of the sequence-specific priming portion in the amplification primer.

Where the standard is instead obtained by amplification from prior-cloned or prior-amplified nucleic acids, the tag can flank the standard sequence at some distance. For example, where the standard is obtained from the single exon probes described in any of WO 01/57270, WO 01/57271, WO 01/57272, WO 01157273, WO 01/57274, WO 01/57275, WO 01/57276, WO 01/57277, WO 01/57278, or WO 01/86003, the standard sequence will typically be separated from the tag sequence by at least a first priming site, which priming site is present in the single exon probe to permit its propagation by in vitro amplification.

Where a plurality of tags are physically linked to each standard, the tags can be contiguous to one another or can be present discontinuously. Where separated from one another, they can collectively be positioned on a single side of the standard sequence (that is, either 5' or 3' to the standard sequence in the standard and MRD vectors), or can be positioned respectively on both sides of the standard.

The standard sequence can further and usefully be physically linked in the standard and MRD vectors to at least a first priming sequence.

The priming sequence facilitates sequencing and/or amplification of the sequence-tagged standard.

In contrast to the sequence tags, the priming sequence need not be unique to each standard. Where the priming sequence is common to all standards, a single oligonucleotide can be used commonly to prime sequencing and/or amplification of all of the tagged standards.

A single priming sequence readily permits linear amplification of the standard, such as by transcription driven by phage polymerases, such as T7, T3, or SP6.

In other embodiments, the singly- or multiply-tagged standard is linked to a first priming sequence and a second priming sequence, the first and second priming sequences permitting geometric amplification of the tagged standard therebetween.

Usefully, the first and second priming sequences in these embodiments differ from one another, but are the same as the first and second priming sequences, respectively, of all other standards desired to be used in a single MRD reaction. This permits a single pair of 5' and 3' primers to be used commonly to amplify all standards that are in the phenotypically sorted plasmid pool.

The priming sites can also usefully include one or more restriction sites, typically restriction sites not found elsewhere in the MRD vector. Usefully, the priming site can include a polylinker that contains a high density of such restriction sites. Such restriction sites are useful, inter alia, for facilitating cloning of the tagged standard into the standard vector, for recovering phenotypically sorted standards by restriction digest of phenotypically sorted plasmids, and for cloning of the phenotypically tagged standards into other vectors (whether or not the tagged standards are first recovered by restriction or amplification followed by restriction digest).

The sorted duplexes are then identified by detection of the sequence tag linked thereto.

In a first series of embodiments, the sorted duplexes are detected by specific hybridization of the sequence tags, tagged duplexes, or nucleic acids derived therefrom to a microarray having probes complementary to the sequence tags.

As used herein, the term "microarray" and equivalent phrase "nucleic acid microarray" refer to a substrate-bound collection of plural nucleic acids, hybridization to each of the plurality of bound nucleic acids being separately detectable. The substrate can be solid or porous, planar or nonplanar, unitary or distributed.

As so defined, the term "microarray" and phrase "nucleic acid microarray" include all the devices so called in Schena (ed.), *DNA Microarrays: A Practical Approach* (Practical Approach Series), Oxford University Press (1999) (ISBN: 0199637768); *Nature Genet.* 21(1)(suppl):1–60 (1999); and Schena (ed.), *Microarray Biochip: Tools and Technology*, Eaton Publishing Company/BioTechniques Books Division (2000) (ISBN: 1881299376), the disclosures of which are incorporated herein by reference in their entireties.

As so defined, the term "microarray" and phrase "nucleic acid microarray" also include substrate-bound collections of plural nucleic acids in which the plurality of nucleic acids are distributably disposed on a plurality of substrates, such as beads, rather than on a unitary planar substrate, as is described, inter alia, in Brenner et al., *Proc. Natl. Acad. Sci. USA* 97(4):1665–1670 (2000), the disclosure of which is incorporated herein by reference in its entirety; in such case, the term "microarray" and phrase "nucleic acid microarray" refer to the plurality of substrates (e.g., beads) in aggregate.

To prepare labeled nucleic acids for hybridization, the sequence tags or tagged duplexes present in the phenotypically sorted population can be retrieved and labeled by known techniques.

For example, the phenotypically sorted MRD vectors can be linearized, and labeled probes prepared directly therefrom by RNA transcription driven from a phage promoter positioned in an adjacent priming site; label can be incorporated directly through use of appropriately labeled nucleotides in the transcription reaction.

Alternatively, the sequence tags or tagged duplexes can first be retrieved from the phenotypically sorted plasmids by restriction digest or amplification, typically by PCR, with RNA transcription thereafter performed on the tags or tagged duplexes so retrieved.

In yet another alternative, the sequence tags, or tagged duplexes, are retrieved from the plasmids present in the phenotypically sorted plasmid population by amplification, with or without prior liberation of the tag or tagged duplex by restriction digest. Amplification, such as by PCR, is mediated by a primer pair that flanks the tag or tagged duplex. If one or both amplification primers is labeled, for example by biotin or a directly conjugated fluorophore, the PCR products can be used directly as hybridization probes. Often in such case the amplification is performed asymmetrically to produce an excess of the strand that is complementary to the probes immobilized on the microarray.

Alternatively, a first amplification can be performed without a labeled primer, and a secondary linear amplification then be performed using a labeled primer.

The methods for microarray hybridization and detection are now well known, and need not here be discussed in detail. See, e.g., Schena (ed.), *DNA Microarrays: A Practical Approach* (Practical Approach Series), Oxford University Press (1999) (ISBN: 0199637768); *Nature Genet* 21(1)(suppl):1–60 (1999); Schena (ed.), *Microarray Biochip: Tools and Technology*, Eaton Publishing Company/BioTechniques Books Division (2000) (ISBN: 1881299376); Shoemaker et al., *Nature Genetics* 14:450–456 (1996); and Winzeler et al., *Science* 285:901–906 (1999), the disclosures of which are incorporated herein by reference in their entireties.

A number of advantages are realized by using the specific hybridization of genotypically-linked sequence tags to bar code microarrays to detect and identify the phenotypically sorted standards in the present invention.

First, standards of distinct sequence that differ by only a few nucleotides can as readily be discriminated as can standards differing substantially in sequence, permitting a plurality of allelic variants of a locus to be used concurrently to query a sample for variation at a single locus. Such concurrent query permits a rare allele to be detected as a sequence that differs concurrently from all of the common alleles. As few as two, or three, and as many as four, five, six, seven, even 10 or more allelic variants of any given locus can be detectably included as separately tagged standards in a single reaction.

Second, because the microarray is specific for the tags, rather than for the standards, generic bar code microarrays can be constructed that can be used for any pool of standards, so long as the standards are physically linked in the standard and MRD vectors to the requisite, complementary, sequence tags.

Third, the generic nature of the bar code microarray allows a single set of optimal hybridization conditions to be determined, and thereafter used without individualization or further optimization.

Although hybridization to a bar code microarray presents certain advantages and is at present preferred for detecting the sequence tags linked to the phenotypically sorted duplexes, the genotypically-detectable element linked to each duplex in the MRD vector can be detected by other means.

For example, the genotypically-detectable element can be amplified from the phenotypically sorted MRD vectors using at least one primer that is specific to the genotypically detectable element. The primer is cleavably linked a unique mass tag. Following amplification, the mass tag is cleaved from the primer and detected and discriminated from other such mass tags using mass spectrometry. Mass tags are reviewed, inter alia, in Kokoris et al., *Molecular Diagnosis* 5:329–340 (2000), the disclosure of which is incorporated herein by reference in its entirety.

As has been described above, sequence variation will typically (but will not invariably) be sought in genomic samples. Typically, therefore, at least one among the plurality of distinct DNA duplexes to be sorted (often all such duplexes in a reaction) will have as the standard strand of the "test duplex" a sequence that is identical to a naturally-occurring genomic sequence, and the samples being queried will be derived from genomic DNA. The genomic sequence can be prokaryotic or eukaryotic in origin.

Among eukaryotic species from which genomic samples usefully can be drawn are humans, related primates, such as chimpanzee, monkeys (including rhesus macaque), baboon, orangutan, and gorilla, and rodents typically used as laboratory models, such as rats, mice, hamsters and guinea pigs. Sample nucleic acids can also usefully be derived from lagomorphs, such as rabbits; and from larger mammals, such as livestock, including horses, cattle, sheep, pigs, goats, and bison. Also useful are samples drawn from fowl such as chickens, geese, ducks, turkeys, pheasant, ostrich and pigeon; fish such as zebra fish, salmon, tilapia, catfish, trout and bass; and domestic pet species, such as dogs and cats.

Plants from which sample nucleic acids can usefully be derived include, for example, experimental model plants, such as *Chlamydomonas reinhardtii*, *Physcomitrella patens*, and *Arabidopsis thaliana*; crop plants such as cauliflower (*Brassica oleracea*), artichoke (*Cynara scolymus*); fruits such as apples (*Malus*, e.g. *Malus domesticus*), mangoes (*Mangifera*, e.g. *Mangifera indica*), banana (Musa, e.g. *Musa acuminata*), berries (such as currant, *Ribes*, e.g. *rubrum*), kiwifruit (*Actinidia*, e.g. *chinensis*), grapes (*Vitis*, e.g. *vinifera*), bell peppers (*Capsicum*, e.g. *Capsicum annuum*), cherries (such as the sweet cherry, *Prunus*, e.g. *avium*), cucumber (*Cucumis*, e.g. *sativus*), melons (*Cucumis*, e.g. *melo*), nuts (such as walnut, *Juglans*, e.g. *regia*; peanut, *Arachis hypogeae*), orange (*Citrus*, e.g. *maxima*), peach (*Prunus*, e.g. *Prunus persica*), pear (*Pyra*, e.g. *communis*), plum (*Prunus*, e.g. *domestica*), strawberry (*Fragaria*, e.g. *moschata* or *vesca*), tomato (*Lycopersicon*, e.g. *esculentum*); leaves and forage, such as alfalfa (*Medicago*, e.g. *sativa* or *truncatula*), cabbage (e.g. *Brassica oleracea*), endive (*Cichoreum*, e.g. *endivia*), leek (*Allium*, e.g. *porrum*), lettuce (*Lactuca*, e.g. *sativa*), spinach (*Spinacia*, e.g. *oleraceae*), tobacco (*Nicotiana*, e.g. *tabacum*); roots, such as arrowroot (*Maranta*, e.g. *arundinacea*), beet (*Beta*, e.g. *vulgaris*), carrot (*Daucus*, e.g. *carota*), cassava (*Manihot*, e.g. *esculenta*), turnip (*Brassica*, e.g. *rapa*), radish (*Raphanus*, e.g. *sativus*), yam (*Dioscorea*, e.g. *esculenta*), sweet potato (*Ipomoea batatas*); seeds, including oilseeds, such as beans (*Phaseolus*, e.g. *vulgaris*), pea (*Pisum*, e.g. *sativum*), soybean (*Glycine*, e.g. *max*), cowpea (*Vigna unguiculata*), mothbean (*Vigna aconitifolia*), wheat (*Triticum*, e.g. *aestivum*), sorghum (*Sorghum* e.g. *bicolor*), barley (*Hordeum*, e.g. *vulgare*), corn (*Zea*, e.g. *mays*), rice (*Oryza*, e.g. *sativa*), rapeseed (*Brassica napus*), millet (*Panicum* sp.), sunflower (*Helianthus annuus*), oats (*Avena sativa*), chickpea (*Cicer*, e.g. *arietinum*); tubers, such as kohlrabi (*Brassica*, e.g. *oleraceae*), potato (*Solanum*, e.g. *tuberosum*) and the like; fiber and wood plants, such as flax (*Linum*, e.g. *Linum usitatissimum*), cotton (*Gossypium* e.g. *hirsutum*), pine (*Pinus* spp.), oak (*Quercus* sp.), eucalyptus (*Eucalyptus* sp.), and the like; and ornamental plants such as turfgrass (*Lolium*, e.g. *rigidum*), petunia (*Petunia*, e.g. x *hybrida*), hyacinth (*Hyacinthus orientalis*), carnation (*Dianthus* e.g. *caryophyllus*), delphinium (*Delphinium*, e.g. *ajacis*), Job's tears (*Coix lacryma-jobi*), snapdragon (*Antirrhinum majus*), poppy (*Papaver*, e.g. *nudicaule*), lilac (*Syringa*, e.g. *vulgaris*), hydrangea (*Hydrangea* e.g. *macrophylla*), roses (including *Gallicas*, *Albas*, *Damasks*, *Damask Perpetuals*, *Centifolias*, *Chinas*, *Teas* and *Hybrid Teas*), orchids, and ornamental goldenrods (e.g. *Solidago* spp.).

Sample nucleic acids can also usefully be derived from lower eukaryotes, such as yeasts, particularly *Saccharomyces cerevisiae*, *Schizosaccharomyces pombe*, *Pichia* species, such as *methanolica*, *Ustillago maydis*, and *Candida* species, or from multicellular eukaryotes such as *C. elegans*, zebra fish, and *Drosophila melanogaster*.

Identification of Common Alleles

As noted above, the methods of the present invention permit rare alleles to be detected as sequences that differ from all common alleles, which common alleles can now readily be included as standards in a single assay.

In another aspect, the invention makes possible the ready discovery of such common alleles, thus further facilitating discovery and scoring of rare alleles.

In the method of this aspect of the invention, the sample being queried is pooled from a plurality of individuals. The sample can be drawn from as few as 2 individuals, but is typically pooled from at least 3, 4, 5, 10, 15, even at least 20, 25, 30, 35, or 40, 45, or 50 individuals or more. A single locus can be screened, but higher throughput is achieved by multiplex analysis, in which a plurality of loci are concurrently queried.

MRD vectors are prepared, with each test duplex therein containing a standard strand and a strand drawn from the pooled nucleic acid sample. The standard will be an identified allele of a chosen locus. Although the identified allele is statistically more likely to represent a common allele, this original standard sequence need not occur commonly in the queried population. As above, each standard is linked both to a phenotypically sortable genetic element and to at least a first genotypically detectable genetic element, which genetic element will preferably be unique among such elements used in any one MRD reaction.

The resulting MRD vectors (with their respective test duplexes) are then phenotypically sorted based upon the ability of each duplex to initiate a mismatch corepair event in vivo. The duplexes present in the phenotypically sorted population are detected and identified, with detection and identification effected by detecting the sequence tags linked to the test duplex.

When the directionality of strand repair has been engineered to use the variant sequence as template, as in MRD embodiments described above, the phenotypically sorted duplexes will bear the variant sequences—that is, will have sequences that were present in the population from which the sample nucleic acids were pooled, and that vary from the original standard.

The variant alleles can then be used to create additional standards, which additional standards can then be used in one or more subsequent rounds of MRD, followed by isolation and construction of standards. Each such additional round can identify further alleles, with the alleles that occur most commonly in the population being more frequently and readily identified.

The additional allelic standards can then be used concurrently with the original standard in the methods of the present invention to identify rare allelic variants.

In one approach to such rare allele detection, nucleic acids are pooled from a plurality of individuals and queried in an MRD reaction that includes standards that correspond to common alleles of one or more desired loci. The resulting phenotypically sorted pool is enriched in variants that differ from the common alleles. With the background levels exhibited in the MRD system as previously described, an allele with a frequency of 5% in the initial sample pool would be enriched to about 50% in the variant pool, and would thus readily detectable by direct sequencing or other well known approaches, such as denaturing high pressure liquid chromatography (DHPLC).

Further enrichment can be obtained by repeating the MRD reaction, using the phenotypically sorted pool of duplexes as the sample to be queried by the same standards in a second round of MRD. For example, an allele with a frequency of 1% in the initial sample pool would be estimated, given levels of background exhibited by the MRD system as previously described, to be enriched to about 50% after two rounds, and would thus at that point be readily detectable by direct sequencing or other means.

Where, however, the rare alleles occur in a queried population at a frequency below that of the background in the MRD reaction, detection is confounded. Background is defined herein as the rate at which nonvariant test duplexes are phenotypically sorted as if they had had mismatches capable of initiating mismatch corepair.

In another aspect, therefore, the present invention provides compositions and methods that decrease background in the MRD reaction, thus improving the ability of MRD to detect rare alleles.

In the embodiments shown in FIGS. 10A–10C and discussed above, the presence of a correctable mismatch in the test duplex co-"repairs" Cre recombinase to an inactive, and thus nondominant, form.

The present inventor has now discovered that a major source of background in such embodiments is, surprisingly, the slow, and/or inadequate, expression of Cre recombinase, which permits plasmid segregation to occur before the antibiotic cassette can be eliminated from the F' episome by Cre-mediated recombination. The result is that certain of the daughter cells of the original transformant erroneously bear only the phenotypically nondominant (i.e., inactive) form of Cre recombinase and an unrecombined F' episome, and thus exhibit the antibiotic phenotype expected of cells that had corepaired the recombinase to an inactive form.

In the MRD vector schematized in FIGS. 10A–10C, Cre expression is driven by the lactose promoter. Without intending to be bound by theory, the present inventor believes that catabolite repression of this promoter in the presence of a carbon source, such as glucose, is responsible for some of the background observed using the MRD vector of FIGS. 10A–10C. That is, only after the depletion of glucose in the rich media (Luria Broth) used in the MRD procedure does the lactose promoter become active.

In addition, and without intending to be bound by theory, the present inventor believes that some of the background can be attributed to a poor ribosome binding site (RBS) of the cre construct used in the above-described MRD vector.

Furthermore, there appears to be a short translated leader sequence that terminates upstream of the cre ATG start site in the prior-described MRD vector, with Cre translation apparently facilitated by translational reinitiation, where the ribosomal S30 subunit remains bound to the mRNA after termination and reinitiates translation at a nearby start site.

Thus, in another aspect, the invention provides an improved vector for use in mismatch repair detection (MRD).

In the improved vectors, the phenotypically sortable genetic element is transcribed from a tightly regulated strong promoter and translation is initiated using a heterologous, typically strong consensus, ribosomal binding site (RBS).

In typical embodiments, the phenotypically sortable genetic element comprises the coding region of a recombinase, typically cre recombinase.

The tightly-regulated strong promoter can be a T7 promoter, which is regulated by the presence and amount of T7 RNA polymerase, as further shown in Example 7, below. The strong selectivity of the bacteriophage T7 RNA polymerase for its cognate promoter sequences, the high level of activity of the polymerase, and the high efficiency of translation mediated by the T7 gene 10 translation initiation signals provide significant advantages.

Other tightly regulated strong promoters can be used as well. For example, the promoter can be drawn from the araBAD operon, which controls the arabinose metabolic pathway in *E. coli*; pBAD vectors (Invitrogen, Carlsbad, Calif.) allow precisely modulated heterologous expression. As another example, the tetracycline-regulated promoter, PLtet0–1, can be used, permitting tightly controlled expression by the highly specific Tet repressor and induction by anhydro-tetracycline (aTc).

The heterologous ribosome binding site (RBS) can be a strong natural or synthetic consensus RBS, optimally positioned upstream of the recombinase ATG start site. Such sequences are known in the art. See, e.g., Shultzaberger et al., "Anatomy of *Escherichia coli* Ribosome Binding Sites," *J. Mol. Biol.* 313(1):215–28 (2001), the disclosure of which is incorporated herein by reference in its entirety.

The vectors will often, during use, further include a standard sequence, which sequence is used to query samples for sequence variation, and at least a first genotypically detectable element, or sequence tag.

Accordingly, the vectors of this aspect of the invention can be used in the methods described above, and it is another aspect of the present invention to provide such methods.

Figure 11:
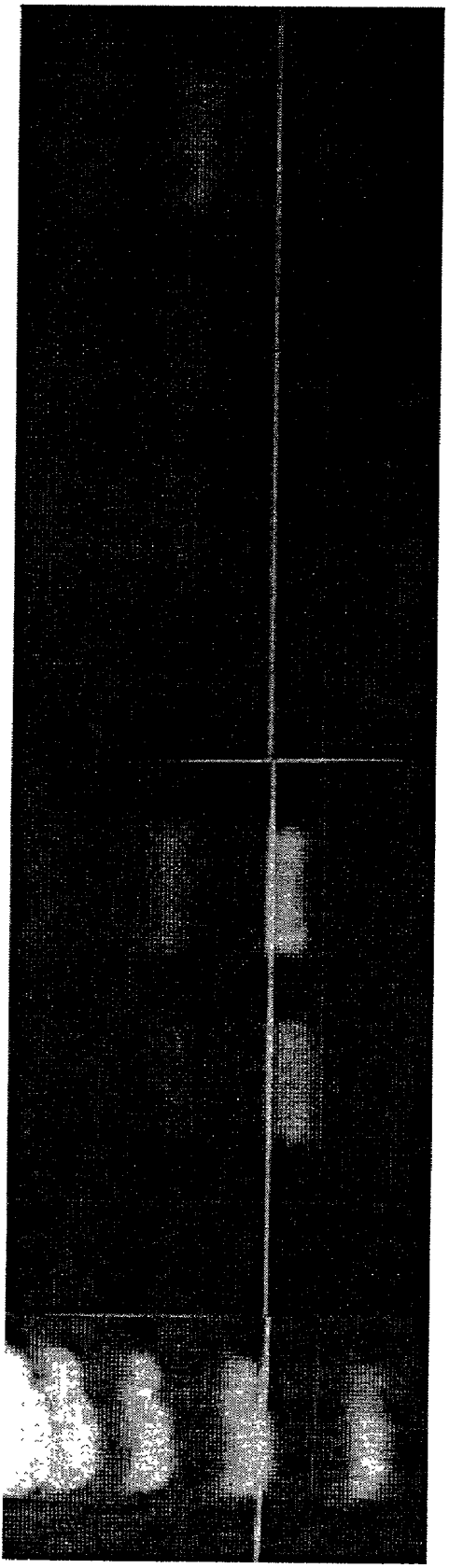
FIG. 11 is a photograph of an agarose electrophoresis gel after staining, showing improved phenotypic sorting by an improved MRD vector/strain combination.

As demonstrated in Example 7 and illustrated in FIG. 11, the improved vectors, by expediting high level expression of Cre recombinase before host cell division, substantially reduce background.

Further reductions in background can be achieved alternatively or in addition by the converse approach: delaying initial cell division.

For example, initial cell division can be delayed by the use of antibiotics to inhibit bacterial septation. Antibiotics such as piperacillin and furaziocillin specifically inhibit the murein laid down during the septum formation, but not during cell elongation. These antibiotics act in under five minutes, and their effects are reversible upon withdrawal.

Thus, following transformation of the pool of MRD vectors into the appropriate host cell strain, piperacillin is added for an hour, and the cells then spun and resuspended in media with the selective antibiotics (ampicillin and either tetracycline or streptomycin), but not piperacillin.

Piperacillin is susceptible, however, to β-lactamase expressed by the amp$^R$ MRD plasmids. To forestall undue inactivation of piperacillin, an additional amount of piperacillin can be added after transformation; furthermore, an alternative selectable marker, such as kanamycin resistance, can be used as the constitutive selectable marker on the standard (and thus MRD) vectors.

An alternative to use of septation-inhibiting antibiotics is to use a strain for phenotypic sorting that has a temperature sensitive mutation that affects septum formation. Mutations in any of several genes can produce the phenotype of filamentous growth under the restrictive temperature. For example, strains carrying mutations ftsA, ftsI, and ftsZ are freely available from the E. coli genetic stock center; such mutations can thus readily be engineered into the strain to be used for phenotypic sorting, such as the MUTATION SORTER™ strain (see Example 5).

After transformation, the cells can be held at the restrictive temperature to inhibit septation, during which time the phenotypically sortable genetic element is repaired and expressed. After a suitable period at the restrictive temperature, such as an hour, the cells can be incubated at the permissive temperature with the appropriate selection antibiotics.

Another cause of background in the MRD assay as practiced using hemimethylated MRD vectors is the accumulation of spurious mutations in the standard vectors occasioned by their propagation in a dam methylase deficient strain (dam$^-$).

Dam$^-$ strains are about 50 fold more mutagenic than are wild type strains.

Assuming a wild type mutation rate of $10^{-9}$ per base per generation, a plasmid size of $4*10^3$ base pairs, and 50 generations of growth (to form the initial colony, possible purification, culture for storage, and single stranded preparation), the mutated fraction would be $10^{-9}*50*4*10^3*50=0.01$. Assuming 100 generations of growth, the fraction becomes 0.02, about half the background observed in MRD prior to the present invention.

Accordingly, in another aspect, the invention provides standard vectors that have been propagated in a strain having an inducible dam gene, and methods for their preparation. The dam gene is expressed throughout the growth of the standard-generating bacteria, except for the terminal generations, typically final 5–10 generations. By "terminal generations" is intended those generations that immediately precede plasmid recovery or, where the standard vectors are to be single-stranded, phage-assisted ssDNA rescue. By reducing the number of generations of growth in the absence of dam activity, the fraction of mutated plasmids is reduced accordingly.

In an alternative embodiment, the standard vectors are prepared in a dam$^+$ host, and transformed into and thereafter propagated in a dam host only to prepare vectors for the MRD reaction. This latter approach will occasion longer growth in the dam host (and therefore higher fraction of mutated plasmids) than does use of inducible dam gene described above. Accordingly, the two approaches can be combined, preparing standard vectors in a dam$^+$ host, and then transforming the standards into a host having inducible dam methylase, which methylase is expressed until the final several generations prior to recovery of standard vector.

In yet another embodiment, no dam$^-$ host is utilized, and the strandedness of corepair is directed instead by other methods, such as "strand polarized" nicks or gaps, as further described herein.

The signal:noise ratio can also be improved by decreasing signal loss.

Loss of signal is defined as the rate at which heteroduplexes having mismatches are phenotypically sorted as if they had been homoduplexes lacking variation. In embodiments in which the phenotypically sortable genetic element encodes Cre recombinase, as in FIGS. 10A–10C, such missorted heteroduplexes will contribute to the pool of colonies that grow in the presence of streptomycin.

As practiced using the vectors and host strain illustrated, e.g., in Example 5, signal loss is generally less than 20%, but for some sequence variations is much higher.

The present inventor has now discovered that a large fraction of the lost signal is attributable to inefficient propagation of repair from the initiating mismatch in the test duplex of the MRD vector to the otherwise "uncorrectable" mismatches in the phenotypically sortable genetic element.

In the vectors used in Example 5, below, the "uncorrectable" loop in the phenotypically sortable genetic element is more than 200 base pairs downstream of the ATG start site of the cre coding region, itself about 100 base pairs from the test duplex.

Accordingly, further improved vectors place the loop as close to the test duplex as possible, thus reducing the distance required for effective corepair initiated within the test duplex.

In addition, a certain fraction of the loss of signal is secondary to Cre activity present before repair. That is, the transformed heteroduplex expresses enough of the cre message before the repair event as to produce recombination of the antibiotics cassette on the F' episome notwithstanding subsequent "repair" to the phenotypically nondominant, inactive, form.

The present inventor has now discovered that this premature expression of Cre recombinase results from positioning the active Cre recombinase allele on the strand of the MRD vector that is capable of immediate expression upon transformation into the host cell strain.

To solve the problem, the invention further provides standard (and thus resulting MRD) vectors in which the phage origin of replication is opposite in orientation from that in the above-described MRD vectors. The result is that the opposite strand is rescued during preparation of ss standard vectors. No change is effected in the strandedness of methylation, and thus no change is effected in the dynamics of phenotypic sorting. However, the change in the orientation of the phage origin prevents Cre expression before plasmid replication, and thus before potential mismatch-initiated corepair.

In an alternative embodiment, vectors with the prior existing orientation of the phage origin are used, but with a delay in addition of IPTG following transformation.

Alternatives to Loops Bigger than 5 Nucleotides

Although the embodiments described above use mismatch loops of five or more contiguous nucleotides to render the marker heteroduplex uncorrectable in the absence of an initiating mismatch in the test duplex, other embodiments are also within the scope of the invention. Indeed, any mismatch not repaired on its own, but that can be corepaired, can be used.

It is known, for example, that nucleotide loops of 4 nucleotides are only marginally repaired; some 4-nucleotide loops are likely not to be repaired at all and could thus serve to render the heteroduplexed marker uncorrectable. Even some single base variations can serve as a marker variation repair only in the presence of initiating mismatches elsewhere on the vector; some single nucleotide variations that are not repaired have been reported.

MRD can itself be used as an assay to screen for such "uncorrectable" changes, simply by incorporating changes to be assayed for "correctability" into the "XY" test heteroduplex itself. If such changes cannot be corrected, no corepair of the marker will occur. Conversely, if the changes can be corrected, corepair will occur.

Alternatives to Hemimethylation

In another alternative, nicks or gaps, rather than hemimethylation, are used to direct the strand to be repaired. One advantage is that the use of nicks (or gaps) circumvents the need to propagate any of the nucleic acids in dam strain, which can itself introduce spurious sequence alterations, either in the marker or in a test duplex strand.

To utilize nicks to direct the strandedness cf repair, the replicable test vector can be constructed, as above-described, by annealing of a closed circular vector chimera (a chimera that includes both marker and test sequence) with a second linearized marker vector and a second test strand. In contrast to the approach above-described, a ligation step prior to transformation is omitted, and the nicked strand is preferentially repaired.

A disadvantage, however, is that the repaired strand will be that carrying the allele of the test duplex that is being queried, rather than the allele that serves as the standard. This approach is, therefore, less readily applied to experiments in which variant alleles are to be enriched, and/or those in which multiple rounds of MRD are desired.

One solution is to engineer the "A" and "I" vectors so that only one strand contains restriction sites recognized by the nicking endonuclease N.BstNBI (catalogue nos. R0607S and R0607L, New England Biolabs, Beverley, Mass., USA), which generates a single-strand nick four bases downstream from its nonpalindromic recognition sequence (GAGTCNNNN). Proper orientation of an f1 origin in the "A" and "I" vectors permits rescue of single-stranded vector chimera (for example, "AX" chimera) having both the standard test strand and at least one occurrence of the N.BstNBI recognition sequence, which sequence is absent from the complementary strand. After denaturation, annealing and ligation, the heteroduplex test vector is then nicked exclusively on the "standard" strand using N.BstNBI. After transformation, corepair initiated at a mismatch in the test duplex is directed to the "standard" strand, using the variant, nonstandard, allele as template, which allows subsequent isolation of the variant should isolation be desired.

To utilize gaps to direct the strandedness of repair, the linearized vector used in the annealing step is smaller than the vector sequence in the closed circular molecule, leaving a gap after annealing. Usefully, the gap is small in size (<20 nt), since long single-stranded stretches in the heteroduplex might be subject to degradation by techniques used to eliminate single stranded and homoduplexed species prior to transformation. Corepair is preferentially directed to the gapped strand.

A disadvantage, however, is that the repaired strand will be that carrying the allele of the test duplex that is being queried, rather than the allele that serves as the standard. This approach is, therefore, less readily applied to experiments in which variant alleles are to be enriched, and/or those in which multiple rounds of MRD are desired.

Figure 9A:
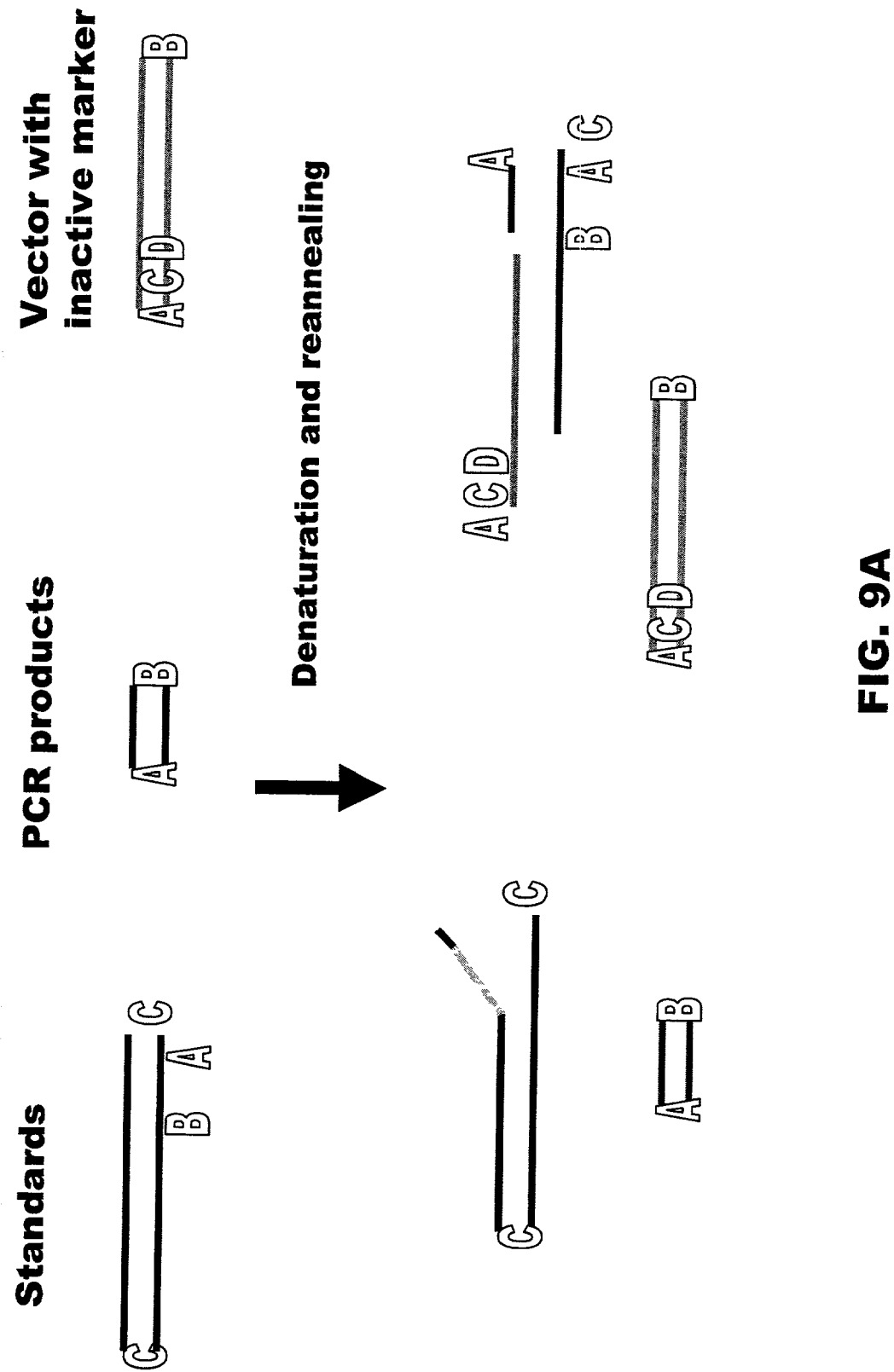
FIGS. 9A and 9B schematize an approach for constructing gapped vectors.
Figure 9B:
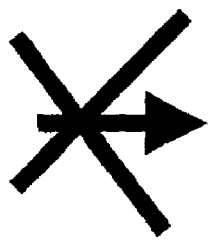
Figure 9B:
Figure 9B:
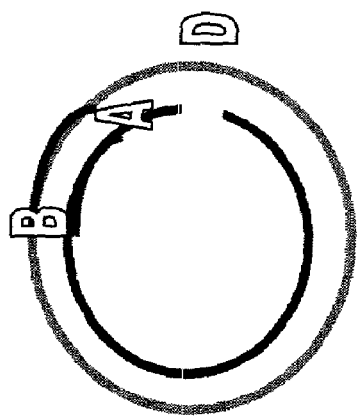

One solution is shown in FIGS. 9A and 9B.

In this embodiment, fragments are cloned into "A" vector having the active (dominant) marker ("A" vector) by double digest cloning with restriction enzymes A and B (not shown); thereafter, these standards are digested with a restriction enzyme C which can cut as few as several bases away from A to yield a collection of linearized double-stranded vectors (shown in FIG. 9A, top left). The vector carrying the inactive (i.e., nondominant) marker ("I" vector, FIG. 9A, top right) is digested with A and B. D signifies a small segment of DNA that is present in the inactive vector but not the active vector.

Test PCR products, digested with A and B (FIG. 9A, top center), are combined in a single denaturation-reannealing reaction with linearized standards and linearized "I" vector to yield four classes of hybridization products, depicted in the middle of FIG. 9A. Hybridization products include: self hybridization of the PCR products, self hybridization of "I" vector, hybridization of two standard strands carrying two different fragments, as well as the desired heteroduplex.

Since many different fragments are being tested, it becomes unlikely that two standard strands carrying the same test fragment will self-hybridize. Standards that heteroduplex with other standards can be eliminated by removal of partially single stranded species.

By performing ligation under dilute conditions, the desired heteroduplex, shown on the right in the middle of FIG. 9A, circularizes, producing a gapped heteroduplex test vector in which the gap is located in the standard strand (FIG. 9B).

These circular molecules are then transformed into bacteria and the rest of the MRD reaction is done per the usual protocol.

Alternatives to Bacteria

Although the embodiments of MRD described above utilize bacterial mismatch repair systems, eukaryotic cells also have an active mismatch repair systems that can be used to report mismatches.

It has been shown, for example, that yeast do not repair certain types of heteroduplexes. In particular, palindromes that form stable stem-loop structures are not repaired, except when co-repaired with a single point mismatch. See Nag et al., "Palindromic sequences in heteroduplex DNA inhibit mismatch repair in yeast," *Nature* 340: 318–320 (1989); Nag et al., "Seven-base-pair inverted repeats in DNA form stable hairpins in vivo in *Saccharomyces cerevisiae*," Genetics 129, 669–673 (1991); Weng et al., "Evidence for independent mismatch repair processing on opposite sides of a double-strand break in *Saccharomyces cerevisiae*", Genetics 148:59–70 (1998). In addition, it has been shown that gaps are able to direct the repair to a particular strand in yeast (Yang et al., "strand interruptions confer strand preference during intracellular correction of a plasmid-borne mismatch in *Saccharomyces cerevisiae*," Current Genetics 35:499–505 (1999)).

Thus, to perform MRD in yeast, such as *Saccharomyces cerevisiae*, a marker is "inactivated" (rendered nondominant or otherwise phenotypically distinguishable 30 from the "active" form) by introducing a palindromic sequence that can only be repaired in the presence of another, initiating, mismatch. In these yeast embodiments of MRD, the heteroduplex test vector is formed with the strand carrying the active marker having a gap that directs strand correction, in the presence of an initiating mismatch in the test duplex, to the active marker strand, using the inactive marker strand as template.

As described above, the marker can confer phenotypes that are distinguished calorimetrically, fluorescently, luminescently, or by differential growth of the host cells.

As for bacterial MRD, a dominant negative version of the marker can be used in yeast MRD. Indeed, markers can be designed that permit selection for and against the wild type form. For example, the marker can be ura3: only cells having the active gene product grow in media lacking uracil, and only cells having the inactive form grow in a medium supplemented with 5 FOA. Centromere (CEN) vectors can be used to reduce the probability of random segregation.

Alternatives to palindromes that form stable stem-loop structures can also be used as "uncorrectable" marker variations in yeast. As above-described for bacterial MRD, alternatives can be tested by MRD itself, by introducing known variations into a test duplex and observing whether such variations trigger corepair of marker heteroduplexes having differences known not to be correctable de novo. For example, the strands of the marker heteroduplex can differ by interpolation of a palindromic stem-loop structure known not to be correctable absent corepair, and nonpalindromic insertions in one of the two test duplex strands then tested for their ability to initiate corepair of the marker. If no corepair is observed, the alteration made in the test duplex is suitable for use in marker heteroduplexes in the practice of MRD.

Indeed, some non-palindromic loops and single base mismatches have been reported not to be repaired well in yeast and thus could be used to inactivate a marker.

Alternatives to Marker Variations

The embodiments of MRD described above utilize corepair of a marker to report the presence of an initiating mismatch in a test duplex located elsewhere in the vector. An alternative obviates the requirement for a heteroduplexed marker.

Others have shown that a bacterial triple mutant lacking RecJ, ExoVII and ExoI, and a quadruple mutant lacking RecJ, ExoVII, Exo I, and ExoX, have low tolerance for mutagenic agents. It was suggested that mismatch repair events on chromosomes of these mutants are aborted, leading to death. If similar interruption of mismatch repair occurs for mismatches carried on a plasmid, these strains can be utilized to detect mismatches without the requirement for a marker variation on the test vector.

Heteroduplexes prepared by any of the methods described above can be transformed into these mutants. The mismatch repair system is activated in the presence of a mismatch in the test duplex; in these mutant strains, however, such repair is never completed, and the plasmid is unable to replicate. Where the plasmid has a selectable marker, such as an antibiotic resistance gene, inability of the plasmid to replicate leads to cell death under selective conditions. By comparing test fragments recovered by transformation of these mutants versus those recovered by transformation of a wild type strain, fragments carrying variations can be identified.

Applications of the Method

MRD provides a rapid, sensitive, and readily multiplexed method for identifying the presence of sequence variations.

Because MRD does not require prior knowledge of the presence or nature of sequence variations—and indeed, requires only the ability to include a test duplex from the desired locus in the replicable test vector—MRD is uniquely well suited for the high throughput screening for the occurrence of such variations.

For example, MRD can be used for high throughput screening of eukaryotic genomes for exons that have naturally-occurring allelic variants. Exon selection for such an effort can usefully be predicated on data Generated by large scale efforts to predict, and then confirm expression of, exons in eukaryotic genomes, such as the human genome. See, e.g., Penn et al., "Mining the human genome using microarrays of open reading frames," *Nature Genet.* 26(3): 315–8 (2000); Shoemaker et al., "Experimental annotation of the human genome using microarray technology," *Nature* 409(6822):922–7(2001); WO 01/57270, WO 01/57271, WO 01/57272, WO 01/57273, WO 01/57274, WO 01/57275, WO 01/57276, WO 01/57277, and WO 01/57278.

Standards can be constructed for every exon in the genome or, for larger genomes, for a subset of exons, the plurality of standards then used in a single, multiplexed, MRD experiment, or a series of MRD experiments conducted in series or in parallel. Useful subsets include, e.g., subsets having at least one representative exon from each known or suspected gene. And as noted above, because MRD does not require expression of the test duplex, it can be used to screen noncoding regions as well. Particularly useful noncoding regions include those that control gene expression, such as promoters and enhancers.

MRD can thus be used rapidly to produce a high density map of naturally occurring sequence variations, including single nucleotide polymorphisms (SNPs).

Because standards need be constructed only once for each locus to be queried, MRD can be used repeatedly to query a single locus (or indeed, a multiplicity of loci) to identify those sequence variations that have high informational content; in particular, MRD can readily be used to identify those sequence variations that are associated with phenotypes of interest.

For example, a set of standards, comprising as many as 100,000 different loci or more, can be used to categorize sequence variations in a plurality of populations, each population defined by a phenotype common to its members. Variations unique to one of the populations, or that predominate in one of the populations, are those that are more likely to be associated with the phenotype that defines the population.

Putative associations, whether identified by MRD or by other techniques, can readily, and exhaustively, be tested, by using MRD to query a large number of individual samples using a standard having the suspect locus.

Thus, MRD can be used to screen a massive number of candidate genes in order to identify disease-causing variations. Indeed, it is possible to test the coding regions of all human genes in a limited number of MRD reactions. Testing the coding regions of all the genes in a population of patients and controls will readily reveal disease-causing variations. Sensitivity of this direct approach is significantly higher than that of standard association studies, as it does not require assumptions as to the origin of mutation and the prevalence of the disease-carrying ancestral chromosome in the patient population. Methods that detect disease-causing variations directly are more likely than association methods to succeed in identifying these variations. This direct candidate gene screening approach is powerful and effective and can greatly accelerate the identification of variations causing clinically-significant phenotypes, greatly improving disease diagnosis, prognosis, and treatment.

Even without an associated phenotype, patterns of phenotypic variation reported by MRD across a plurality of loci have tremendous utility, serving as a genetic fingerprint.

Genetic fingerprinting is now well known in the art. Genetic fingerprinting by MRD can be used in all existing fingerprinting applications, and permits query of a far greater number of loci, creating a more detailed, higher resolution, fingerprint than is afforded by standard techniques, such as amplified-fragment length polymorphism (AFLP) analysis (Savelkoul et al., *J. Clin. Microbiol.* 37(10):3083–91 (1999)).

Genetic fingerprinting by MRD can be used, for example, to type prokaryotes of clinical interest—such as potentially pathogenic E. coil or Salmonella strains, or known pathogens such as Mycobacterium tuberculosis, chlamydia trachomatis, neisseria spp., including neisseria gonorrhea—either to confirm their pathogenicity or to trace the transmission of pathogenic strains. Genetic fingerprinting by MRD can analogously be used to type viruses of clinical interest, such as HIV, HBV, HCV, HPV, ebola virus. Genetic fingerprinting by MRD can be used to type plant varieties, and in forensic applications to type human genomes.

When loci are known to be associated with a phenotype, a collection of such loci can be used to provide diagnostic or prognostic information.

For example, many tumor cells contain a mutation in one or more oncogenes and/or tumor suppressor genes. Example 5 herein below demonstrates that MRD can identify sequence variations in genes known to be associated with cancer pathogenesis or progression in samples derived from clinically affected individuals.

MRD can be used prognostically, for example for prenatal screening. By allowing simultaneous query of a large number of loci, including all loci known to contribute to diseases, MRD permits standard, sequence-based, tests—which are more expensive and labor intensive—to be reserved for follow-up investigation of only those loci identified to vary from the wild type sequence. For examples, a single screen can include a plurality, or indeed all, of the loci known to contribute to inborn errors of metabolism, from sickle cell anemia to cystic fibrosis. For example, in prenatal diagnosis one might wish to determine whether a mutation in a particular gene, e.g. hemoglobin, dystrophin, ADA, CFTR, p53, RB, CDKN2A, etc., is found in a fetal DNA sample.

MRD can be used to identify variations not only among populations or individuals, but also to identify variations within individuals, such as somatic mutation in tumor cells. Indeed, MRD can provide a comprehensive genetic grading system for tumors, with longitudinal query of biopsy samples from a single individual permitting tumor progression to be monitored.

Determining whether a particular gene is altered in a tumor cell sample is therefore of interest. Among such potentially altered genes are those that are causally involved in the neoplastic process—tumor suppressors and oncogenes—and genes that could mediate resistance to therapeutic agents.

The latter include, e.g., members of the cytochrome P450 family known to affect drug metabolism, such as CYP1A2, CYP2C17, CYP2D6, CYP2E ("CYP2E1"), CYP3A4, and CYP4A11, which appear to be responsible for metabolism of the vast majority of prescribed and over-the-counter drugs. For recent reviews, see Anzenbacher et al., "Cytochromes P450 and metabolism of xenobiotics," Cell. Mol. Life Sci. 58(5–6):737–47 (2001), and Drug. Ther. Bull. 38(12):93–5 (2000).

Other cytochrome P450 enzymes can also usefully be tested, such as CYP1B1 (synonyms: CP1B, GLC3A), CYP1A1 (cytochrome P450, subfamily I (aromatic compound-inducible), polypeptide1), CYP2A6, CYP2A13 (also known as CPAD), CYP2B6 (alternatively denominated CPB6, IIB$_1$ P450, and CYPIIB6), CYP2C8 (same as CPC8, P450 MP-12/MP-20) encoding cytochrome P450, subfamily IIC (mephenytoin 4-hydroxylase), polypeptide 8, which is known to metabolize many xenobiotics, including the anti-convulsive drug mephenytoin, benzo(a)pyrene, 7-ethyoxy-coumarin, and the anti-cancer drug paclitaxel (Taxol®). CYP2C8 also metabolizes cerivastatin, which is a high potency, third generation synthetic statin with proven lipid-lowering efficacy.

Other P450 genes that can usefully provide standards for MRD assessment in a cancer setting are CYP2C9 (cytochrome P450, subfamily IIC (mephenytoin 4-hydroxylase), polypeptide 9), whose expression is induced by rifampin, and which is known to metabolize many xenobiotics, including phenytoin, tolbutamide, ibuprofen, aspirin and S-warfarin, Bigler et al., "CYP2C9 and UGT1A6 genotypes modulate the protective effect of aspirin on colon adenoma risk," Cancer Res. 61 (9):3566–9 (2001), CYP11A (same as P450SCC, cytochrome P450C11A1), CYP2C19 (same as CPCJ, CYP2C, P450C2C, P45011C19, microsomal monooxygenase, xenobiotic monooxygenase, mephenytoin 4'-hydroxylase, flavoprotein-linked monooxygenase), CYP2F1, CYP2J2, CYP3A5, CYP3A7 (catalyzes the prenatal 4-hydroxylation of retinoic acid, playing an important role in protecting the human fetus against retinoic acid-induced embryotoxicity, Chen et al., "Catalysis of the 4-hydroxylation of retinoic acids by cyp3a7 in human fetal hepatic tissues," Drug. Metab. Dispos. 28(9):1051–7 (2000)), CYP4B1, CYP4F2, CYP4F3, CYP6D1, CYP6F1 (related to CYP6D1 and involved in pyrethroid detoxification in insects), CYP7A1, CYP8, CYP1 A, CYP11B1, CYP11B2, CYP17, CYP19, CYP21A2, CYP24, CYP27A1, and CYP51.

Other loci that affect drug resistance are also usefully queried by MRD in the cancer setting.

Among such non-P450 loci are the genes encoding ATP-binding cassette (ABC) proteins, which transport various molecules across extra- and intra-cellular membranes. ABC genes are divided into seven distinct subfamilies (ABC1, MDR/TAP, MRP, ALD, OABP, GCN20, White); some members are well known to confer a multi-drug (multiple drug) resistance phenotype on tumor cells.

Best known among the ABC proteins is ABCB1 (ATP-binding cassette, sub-family B (MDR/TAP), member 1), known alternatively as MDR1 (multi drug resistance 1), P-GP (P-glycoprotein), PGY1, ABC20, and GPI 70, the human homologue of which maps to 7q21.1. Allelic variants of ABCB1 (MDR1) are known to affect its selectivity and/or activity. Hoffmeyer et al., "Functional polymorphisms of the human multidrug-resistance gene: multiple sequence variations and correlation of one allele with P-glycoprotein expression and activity in vivo," Proc. Natl. Acad. Sci USA 97(7):3473–8 (2000); Choi et al., "An altered pattern of cross-resistance in multidrug-resistant human cells results from spontaneous mutations in the mdr1 (P-glycoprotein) gene," Cell 53(4):519–29 (1988).

ABCB4 (ATP-binding cassette, sub-family B (MDR/TAP), member 4)(also known as MDR3, PGY3, ABC21, MDR2/3, PFIC-3) (human homologue maps to 7q21.1), is another useful locus, as are ABCC1, ABCC2 (same as DJS, MRP2, cMRP, ABC30, CMOAT, Canalicular multispecific organic anion transporter), ABCC3 (also known as MLP2, MRP3, ABC31, CMOAT2, MOAT-D, EST90757), ATP-binding cassette, sub-family C (CFTR/MRP), member 4, ABCC4, also known as MRP4, MOATB, MOAT-B, EST170205. Other ABC transporter proteins that can usefully be queried for sequence variation include ABCC4 (MRP4), ABCC5 (MRP5) (provides resistance to thiopurine anticancer drugs, such as 6-mercaptopurine and thioguanine, and the anti-HIV drug 9-(2-phosphonylmethoxyethyl)ad-enine; this protein may be involved in resistance to thiopurines in acute lymphoblastic leukemia and antiretroviral nucleoside analogs in HIV-infected patients); ABCC6

(MRP6), MRP7 (CFTR), ABCC8 (MRP8), ABCC9, ABCC10, ABCC11 (same as HI, SUR, MRP8, PHHI, SUR1, ABC36, HRINS), and ABCC12 (same as MRP9).

Other useful loci that can provide standards and as to which loci sequence variation can be queried include EPHX1 (epoxide hydrolase 1, microsomal xenobiotic), EPHX2 (epoxide hydrolase 2), LTA4H (leukotriene A4 hydrolase), TRAG3 (Taxol® resistance associated gene 3, which is overexpressed in most melanoma cells and confers resistance to paclitaxel, Taxol®), GUSB (beta-glucuronidase), TMPT (thiopurine methyltransferase), BCRP, (breast cancer resistance protein, an ATP transporter), dihydropyrihidine dehydrogenase, HERG (involved in drug transport through potassium ion channels), hKCNE2 (involved in drug transport through potassium ion channels), UDP glucuronosyl transferase (UGT) (a hepatic metabolizing enzyme, a detoxifying enzyme for most carcinogens after different cytochrome P450 (CYP) isoforms), sulfotransferase, sulfatase, and glutathione S-transferase (GST) -alpha, -mu, -pi (which detoxify therapeutic drugs, not least several anti-cancer drugs), ACE (peptidyl-dipeptidase A), and KCHN2 (potassium voltage-gated channel, subfamily H (eag-related), member 2), location 7q35–q36).

Determining the occurrence and frequency of sequence polymorphisms in a population is important in understanding the dynamics of genetic variation and linkage disequilibrium.

To perform this type of analysis, a control (X) copy of the sequence of interest is cloned into the A or "I" vector, usually "A" vector Where a gene is known to be polymorphic, several different vectors, each having a different allelic form, may be used. The "Y" sequence is obtained from a suitable source of DNA, depending on the type of analysis being performed. The "Y" sequence may also be cloned into "A" vector. In a particularly useful embodiment, however, a heteroduplex is formed of "AX" and "I" strands combined with single stranded "Y" DNA, where "Y" may be a denatured PCR product, cDNA etc. The nucleic acids are annealed, and a ligation is performed to produce the test vector.

For genetic testing, one may set up a panel of "A" or "I" vectors having defined regions of a chromosome, for example the BRCA1 gene, or CFTR gene, where a copy of the gene sequence is cloned into the vector. Similarly, for identification of variation involved in clinical phenotypes, one may set up a panel of "A" or "I" vectors carrying many fragments to test for SNPs, or gene variations. Due to allelic variation, it may be necessary to compare several sets of control vectors. The length of some genes may necessitate a series of vectors, in order to cover the entire region. The "Y" sequence DNA is obtained from the individual being tested, using any convenient source of DNA. The "Y" sequence may be added to the "AX"/"I" hybridization reaction, or may be cloned into the "I" vector in a separate reaction. Hybridization of the panel of "X" sequence vectors with the corresponding "Y" sequences may be performed in parallel, or in a multiplex reaction. The presence of specific sequences is then correlated with the presence or absence of active marker gene. One can then determine, for large regions of DNA, or a large number of genes where an individual sequence varies from a standard, control sequence.

The resulting colonies from the above procedure will be a mixture of active marker expressing, having a DNA sequence identical to the control sequence, and lacking active marker, where there was an initiating mismatch in the test sequence. In order to analyze the results, it may be desirable to determine the frequency of these two populations. This may be accomplished by separating the active and inactive colonies into two different pools. Separation may be accomplished by picking colonies, flow cytometry, column separation based on binding of the marker, immunomagnetic bead separation, etc. Vector DNA isolated from these pools is digested with an appropriate restriction endonuclease to release the insert. Gel electrophoresis may then be used to quantitate the amount of insert DNA in each pool, using the vector band as an internal standard, from which the proportion of variant and identical clones can be determined. Acrylamide gels (or other separation methods) can be employed. Alternatively, the insert DNA from each of the pools used as a hybridization probe on a hybridization filter or microarray of fragments corresponding to the fragments being tested. The ratio of signal intensity from hybridization with the active and inactive pool of inserts can be used to determine the proportion of variant and identical sequences. This allows the simultaneous analysis of sequence variation for many different fragments.

The nature of the "X"/"Y" sequences varies. In one embodiment the test sequences will include all the coding regions and their regulatory elements for a particular organism, e.g. human, yeast, etc. In another embodiment they are polymorphic markers that can be used for genetic mapping. In yet another embodiment they are one or several genes that are tested in a clinical setting to for the purposes of improving the diagnosis, prognosis, or treatment for a patient.

This multiplexing can be augmented by assessing the genotype of multiple individuals at the same time, for a particular fragment or genetic sequence of interest. Alternatively, multiple samples may be taken from an individual to determine the extent of somatic mutation in a cell population, e.g. tumor cells, etc. The sample nucleic acid may be an amplification product, cloned fragment, etc. By assessing the genetic variation in a population one can estimate the frequency of variation in a particular population in a variety of genes in one experiment. One can identify genes related to clinically relevant phenotypes by identifying those genes that have a higher frequency of variation in the population of interest as compared with the normal population. In addition this approach can be used to identify fragments carrying variations and therefore can be useful as for SNP testing.

In addition to the use of MRD for identification of human genetic variation involved in clinical phenotypes, e.g., phenotypes affecting the development, progression, or treatment of disease, MRD can clearly be used to test variation in nonhuman species. Identification of variations leading to phenotypes in mice, drosophila, yeast and other species is of concern to researchers. In addition, identifying variations in human pathogen like HIV virus of *Mycobacterium tuberculosis* can have important clinical consequences. Finally other uses of MRD can be in identifying variation relevant to farming phenotypes, e.g. variations leading to increased milk production in cows or prolonged freshness in tomatoes.

MRD can be used not only to identify, but also to isolate, sequence variants, such as variant alleles from a particular locus or region.

There are a variety of reasons that one may wish to isolate variants of sequences, particularly genomic sequences. In some cases, the control sequence will be only partially characterized. For example, many genetic diseases or conditions are known only by their phenotype and general map position, e.g. a high predisposition to breast cancer, obesity, etc. Localization of the gene to a particular map region, or a BAC or YAC clone, still leaves hundreds of thousands of bases of DNA containing the potential gene candidate. MRD provides a means of identifying and isolating the variant sequence.

DNA is isolated from two sources. The DNA may be from a YAC or BAC insert, a restriction fragment from a human chromosome, etc. One source of DNA will have the putative variant sequence, and the other will have the control sequence, e.g. wild-type. Preferably the two sources will be related, e.g. inbred mouse strain, tissue samples from an individual, human parent or sibling, etc.

MRD is performed. The transformant pool that is enriched for variants—that is, the pool distinguished by corepair—is then a ready source of the variant nucleic acids.

The ability of MRD to provide DNA having a variant sequence can be used in "multiplexing" procedures, where multiple DNA fragments are analyzed in a single reaction. Multiplex reactions may be set up for specific fragments of DNA or regions of a chromosome, etc. In multiplex reactions, generally two cycles of MRD will be performed. The first round of MDR provides a number of bacterial colonies (where MRD is practiced in bacteria) having variant or identical allele(s) from a pool of DNA fragments. The second round of MDR further enriches for the variant sequences.

Regions of DNA may be compared in multiplex reactions. One or many different fragments may be isolated in a single reaction. Generally DNA from one source will be fragmented by a suitable method, e.g. restriction endonuclease digestion, etc., cloned into the appropriate vector, hybridized with the other vector as well as DNA from the other source, and a first round of MRD analysis performed in a single reaction. Colonies having inactive marker after the first round are enriched for variant sequences. DNA isolated from these colonies may be compared to the control sequence, using additional round(s) of MRD to further enrich for variants. The majority of inactive colonies from the second round will carry DNA sequences that differ from the control. Where error prone polymerase was used to generate DNA, the method of "cleaning" described below may be used to enrich for true variants.

Isolation of variant fragments can be done for many fragments from many people in the same experiment. For example PCR from a pool of individuals can be performed for many fragments. These PCR products can be annealed and ligated into a heteroduplex "A"/"I" vector. Alternatively they can be annealed to an "A" vector with an "X" sequence already ligated to it. Two MRD procedures might be performed as described above to enrich for the variant fragments. This approach can be useful in identifying in a population the fragments carrying variations and therefore that can be used as genetic markers. In addition this approach may identify variations in coding regions that may be involved in specific clinical phenotypes. This approach can be performed with different populations (one experiment per population) in order to isolate those variations that are specific to a specific population. In other words MRD can be used to identify rare alleles in a population for a large number of genes. An analogous application is the identification of rare alleles produced by somatic mutations or sperms in one individual. Examples of this include identification of rare alleles in a fraction of tumor cells, precancerous changes in a pool of normal cells, mutations caused by environmental mutagens, or somatic mutations that may be relevant in processes such as immune diseases or aging.

MRD may be used in conjunction with Taq polymerase to enrich for molecules that are free of PCR-induced errors. Following this "cleaning" protocol, the cloned PCR products is isolated for further analysis. The products of a Taq PCR reaction are cloned into the control and test vectors, and are then hybridized and transformed. The majority of transformants containing Taq PCR-induced errors will present as heteroduplex molecules containing a mismatch and will not produce active marker. In contrast, those PCR products with no PCR-induced errors will contain no mismatches and will produce active marker. These colonies can be isolated, and if desired, undergo a second round of cleansing. A similar protocol may be used to isolate non-variant sequences from a population.

MRD can also be used for template-driven cloning.

As described above, one particularly useful (but nonlimiting) approach to constructing the replicable test vector uses a single-stranded closed circular standard as a template to align complementary vector and test strands to produce the desired heteroduplex. The subsequent ligation step catalyzes intramolecular nick closure. In effect, one strand of the PCR product has been cloned by hybridization to the standard sequence; that is, construction of a standard plasmid by conventional cloning methods allows further cloning to be directed by hybridization to that standard sequence.

Template-driven cloning can be used for applications, other than MRD, in which specific fragments from many different sources need to be cloned. The goal in such cases would not be to detect variations in specific fragments, but rather to clone these fragments.

As has been described above, the initial product of such template-driven cloning is a heteroduplex between the standard and the captured strand. In order to obtain only the captured strand, template-driven cloning can be followed by mismatch repair, where repair is directed to the standard strand. In contrast to MRD, in which the marker must possess a heteroduplex variation correctable only in the presence of another initiating mismatch, for template-driven cloning applications the marker heteroduplex can, and often will, include mismatches capable of initiating repair, ensuring that the standard strand is necessarily copied from the captured strand.

As with all aspects of the present invention, this approach does not rely upon PCR, or other amplification schemes, to provide the test fragment, but can equally employ restriction fragments and other, nonamplified, fragments.

Kits

It is contemplated that a kit will be provided for the practice of the subject invention. At a minimum, the kit will contain "A" and "I" vectors. The vectors may be single or double stranded. Single stranded vectors may be pre-annealed in an "A"/"I" heteroduplex. Competent host bacteria for growing unmethylated and methylated vector may also be included, as well as an MMR host strain. For analysis of specific DNA sequences, e.g. oncogenes, tumor suppressor genes, human β-globin, human α-globin cDNA and genomic copies of BRCA1 and BRCA2, a panel covering the human dystrophin gene, etc., a kit may be provided where a chimeric "A" vector is provided, containing the "X" (control) sequences. The "A" and "I" vector in this case may also be pre-annealed, to form an "AX"/"I" heteroduplex. Such a kit may also include specific primers for amplifying the "Y" sequence DNA, and optionally, thermostable polymerase.

It is to be understood that this invention is riot limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the cell" includes reference to one or more cells and equivalents thereof known to those skilled in the art, and so forth. All technical and scientific terms used herein have the same meaning as commonly understood to one of ordinary skill in the art to which this invention belongs unless clearly indicated otherwise.

It must be noted that as used herein and in the appended claims, the singular forms "a", "and", and "the" include plural referents unless the context clearly dictates otherwise. Thus, for example, reference to "a complex" includes a plurality of such complexes and reference to "the formulation" includes reference to one or more formulations and equivalents thereof known to those skilled in the art, and so forth.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing, for example, the methods and methodologies that are described in the publications which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, and pressure is at or near atmospheric.

Experimental

EXAMPLE 1

Figure 3:
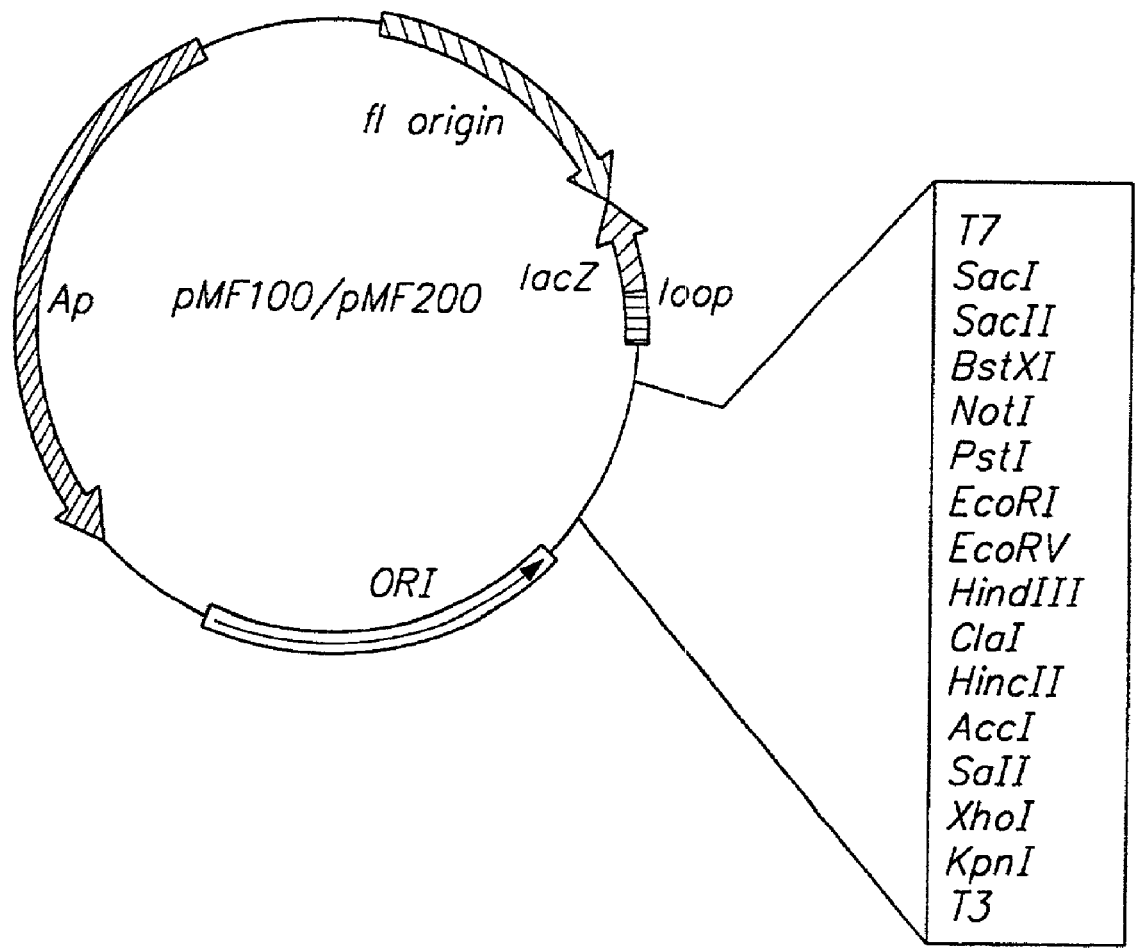
FIG. 3 shows a plasmid map of pMF200 and pMF100.
Figure 4:
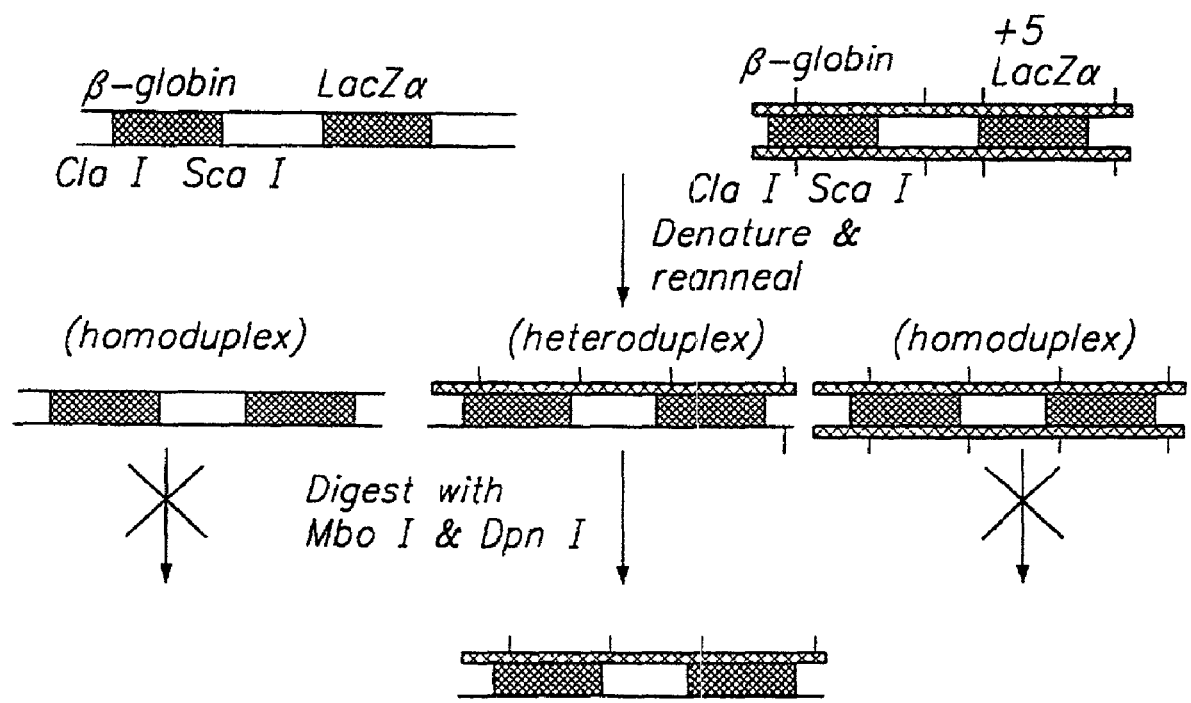
FIG. 4 depicts formation of heteroduplex DNA.
Figure 5:
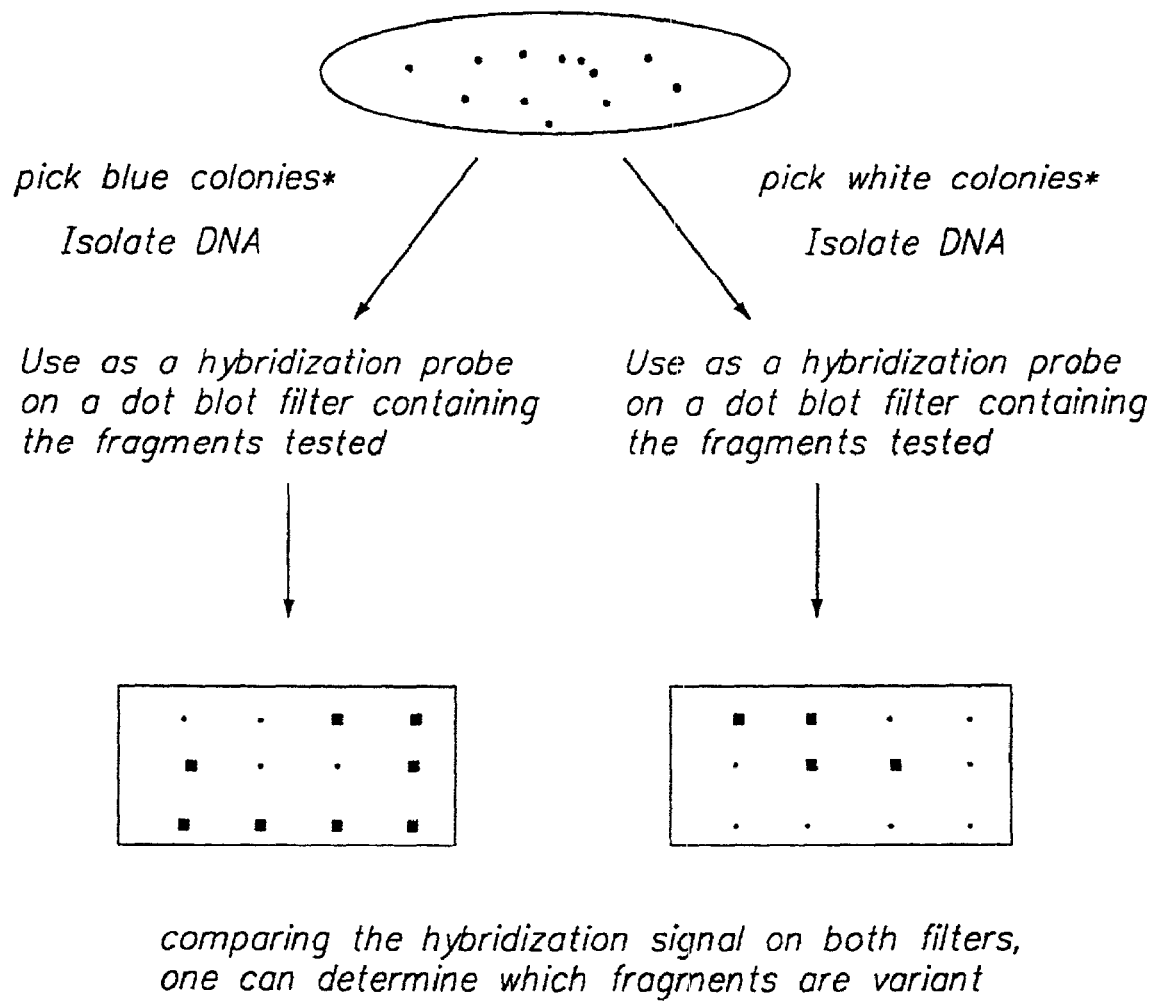
FIG. 5 depicts analysis of MRD results by hybridization.

Two pUC-derived plasmids, the A plasmid (pMF200) and the I plasmid (pMF100), are employed in the MRD procedure. A map of the plasmids is shown in FIG. 3. These plasmids are identical except for a five bp insertion into the LacZα gene of pMF100. This insertion results in white colonies when bacteria transformed with the I plasmid are grown on LB plates supplemented with indolyl-β-D-galactoside (XgaI) and isopropyl-β-D-thiogalactoside (IPTG). In contrast, bacteria transformed with the A plasmid result in blue colonies when grown under these conditions.

The initial step of the MRD procedure consists of cloning one of two DNA fragments to be screened for differences into the A plasmid and cloning of the second DNA fragment into the I plasmid. The A plasmid construct is then transformed into a dam$^-$ bacterial strain, resulting in a completely unmethylated plasmid while the I plasmid construct is transformed into a dam$^+$ bacterial strain, resulting in a fully methylated plasmid. The two plasmids are then linearized, denatured, and reannealed, resulting in two heteroduplex and two homoduplex plasmids. Following digestion with MboI and DpnI, which digest only homoduplexes, the remaining hemimethylated heteroduplexes are circularized, transformed into E. coli, and plated onto agar supplemented with Xgal and IPTG.

In the absence of a mismatch between the two test DNA fragments, the five nucleotide loop in the LacZα gene, resulting from heteroduplex formation between the I and the A plasmids, is not repaired by the mismatch repair system. Subsequent plasmid replication produces both I and A plasmids in a single colony, leading to a blue color. In contrast, if a mismatch is present in the heteroduplex DNA, a co-repair event takes place that involves both the mismatch in the DNA as well as the five nucleotide loop in the LacZα gene. In this case, the unmethylated LacZα gene on the A plasmid is degraded, and replaced by the LacZα gene from the methylated strand of the I plasmid, resulting in a white colony. The data show that co-repair of a mismatch and the LacZα gene in the MRD system occurs even when the distance between them is greater than 5 kb.

Methods

The MRD vectors. PMF100 and pMF200 are derived from pUC19, with the multiple cloning site displaced from the Lac Zα region. In addition, the MRD vectors contain the BgII fragment (2166-472) and most of the multiple cloning site of pBluescript (Stratagene, La Jolla, Calif.). The cloning sites of the MRD vector do not have sites for the restriction endonucleases XbaI, SpeI, BamHI, SmaI and ApaI. The EcoRI site is not unique. PUC19 multiple cloning sites, nucleotides 400–454, were replaced using 70 nucleotide long oligonucleotides with a sequence containing four GATC sites. In addition, the site replacing the pUC19 multiple cloning sites in pMF200 has a 5 bp insertion as compared to pMF100, creating a non-functional LacZα in pMF200. The label "loop" in FIG. 3 indicates this difference.

Formation of heteroduplex DNA. DNA from the unmethylated and methylated plasmids are linearized, denatured, and reannealed. The resulting molecules are fully unmethylated "A" plasmid homoduplexes, fully methylated "I" plasmid homoduplexes, and hemimethylated heteroduplexes. The mixture is digested with MboI, which digests fully unmethylated DNA, and DpnI, which digests fully methylated DNA. Only the heteroduplex, hemimethylated DNA is left.

EXAMPLE 2

As an initial test of the sensitivity and specificity of the MRD system, a single nucleotide mismatch was detected in a 550 base pair DNA fragment derived from the promoter of the mouse beta globin gene (Myers et al. (1985) Science 229:242). MRD was used to compare this DNA fragment, which contains a T at position −49 (relative to the functional transcription start site of the gene) with a second DNA fragment identical in sequence except for at C position −49. The mismatch was located about 700 base pairs from the five nucleotide Lac Zα loop in the vector. Comparison of the two DNA molecules by using MRD resulted in 90% white colonies. In contrast, comparison of the same two DNA molecules with no mismatch (−49T/−49T), resulted in only 7% white colonies. The data is shown in Table 1.

TABLE 1

Detection of Known Point Mutations using MRD

| Sequence Variation* | Fragment Size^ | Distance from Loop^ | % White (Inactive) Colonies@ |
|---|---|---|---|
| None[1] | 0.55 | N/A | 7 |
| G_C[1] | 0.55 | 0.7 | 89 |
| A_T[1] | 0.55 | 0.7 | 84 |
| G_T[1] | 0.55 | 0.7 | 82 |
| A_C[1] | 0.55 | 0.7 | 82 |
| C_T[1] | 0.55 | 0.7 | 90 |
| None[2] | 2.0 | N/A | 8 |
| A_C[2] | 2.0 | 0.4 | 35 |
| None[3] | 2.2 | N/A | 10 |
| C_T[3] | 2.2 | 2.3 | 83 |
| G_A[3] | 2.2 | 2.1 | 86 |
| C_T[3] | 2.2 | 1.6 | 81 |
| T_C[3] | 2.2 | 1.8 | 80 |

*A_T variation means that at the only position of variation between the two fragments compared, the dam⁻ grown variant has an A and the dam⁺ grown variant has a T at the same position on the same strand. Therefore, mismatches produced in such an experiment are A/A and T/T.
^in kilobases.
@At least 250 colonies were counted to determine the percentage.
[1]Experiment using a fragment of the mouse beta globin gene.
[2]Experiment using a fragment of the human agouti gene.
[3]Experiment using fragment of human cystathionine beta synthase gene, at positions 341, 502, 992, and 833, respectively.

Comparison of all possible single nucleotides mismatches at position −49 using MRD revealed proportions of white colonies ranging from 80% to 90%. These results demonstrate that MRD can detect all of the different DNA variations possible at this position with high efficiency.

The MRD system was used to detect a total of five additional single nucleotide mismatches in two different DNA fragments, shown in Table 1. Four of these mismatches are at different nucleotide positions in the human cystathionine beta synthase gene (Kruger and Cox (1995) *Human Molecular Genetics* 4:1155). The remaining one mismatch represent single nucleotide changes in the human agouti gene (Wilson et al. (1995) *Human Molecular Genetics* 4:223). In each case, a single nucleotide mismatch was detected.

A mismatch was detected even when it was as far as 2.3 kb from the Lac Z☐ loop. Since the proportion of white colonies was greater than 50%, co-repair of the mismatch and the loop on the unmethylated strand occurred irrespective of which side of the mismatch was relative to the loop.

To determine whether the efficiency of mismatch detection would remain high if the distance between a mismatch and the vector loop was even larger, the following experiment was performed. A 9 kb test DNA fragment derived from lambda bacteriophage was cloned into the MRD plasmid system and compared with the same test DNA containing a two base pair insertion located 5 kb from one end of the fragment. Addition of the two base pair mismatch resulted in 70% white colonies, as compared to 10% white colonies in the absence of the mismatch. These results indicate that MRD can detect a mismatch in 10 kb of DNA.

EXAMPLE 3

MRD was used to detect unknown mutations in genomic DNA fragments generated by the polymerase chain reaction (PCR). PCR is a practical method for obtaining a particular genomic DNA fragment of interest from many different individuals. Recent advances in PCR technology makes it possible to isolate DNA products greater than 10 kb in length (Barnes (1994) *P.N.A.S.* 91:2216; Cheng et al. (1994) *P.N.A.S.* 91:5695). However, the introduction of errors during the PCR reaction severely limits the use of individual cloned PCR products. In an effort to overcome this limitation, an MRD protocol was developed to enrich for molecules that are free of PCR-induced errors. Following this "cleaning" protocol, the cloned PCR products can be compared for DNA sequence differences by using the MRD procedure described above.

The basic principle underlying the MRD cleaning protocol is the fact that any single PCR-induced mutation will make up a very small fraction of all the molecules generated by PCR. As a result, when the products of a PCR reaction are cloned into the A "blue" and the I "white" MRD vectors and assayed as described above, the majority of products containing PCR-induced errors will present as heteroduplex molecules containing a mismatch and will produce white colonies. In contrast, those PCR products with no PCR-induced errors will contain no mismatches and will result in blue colonies. Given that not all mismatches are repaired with 100% efficiency, some blue colonies can be expected to contain PCR-induced errors following the first round of enrichment. However, if blue colonies are isolated and used in a second round of MRD cleaning, those molecules containing PCR-induced errors can be reduced even further. Since each blue colony contains both a blue MRD plasmid and a white MRD plasmid, the second round of MRD cleaning is carried out as follows. Plasmid DNA isolated from blue colonies following the firs round of cleaning is used to transform both dam⁻ and a dam⁺ bacterial strains. Although both blue and white colonies resulted from each transformation, only the blue colonies are isolated from the dam⁻ transformation, and only the white colonies are isolated from the dam⁺ transformation. Plasmid DNA is prepared from such colonies and heteroduplexes are isolated as described above. Blue colonies arising from transformation with these heteroduplexes are further enriched for the products free of PCR-induced error. In an experiment in which 75% of molecules contain one or more PCR-induced errors following PCR, assuming 95% efficiency of mismatch repair and 10% frequency of white colonies in the absence of a mismatch, the expectation would be 10% blue colonies following one round of MRD enrichment, with 66% of the molecules in such colonies free of PCR-induced errors. If the plasmid DNA from the blue colonies were used for a second round of MRD enrichment, the expectation would be 41% blue colonies, with 96% of the molecule in such colonies free of PCR-induced errors.

As a test of the practicality as well as the efficiency of the MRD cleaning protocol, a 2 kb human chromosome 21-specific PCR product was isolated from each of the two chromosome 21 homologues of a single individual. The two chromosome 21 homologues were separated from each other in independent hamster-human somatic cell hybrid clones. Genomic DNA isolated from these somatic cell hybrid clones was the source of PCR products. When the PCR products derived from each homologue were compared using MRD as described above, approximately 10% blue colonies were observed in each case.

Following two rounds of MRD cleaning, the proportion of blue colonies as 60–80%, data shown in Table 2. In contrast, when these "cleaned" PCR products derived from the two homologues were compared with each other by using MRD, approximately 90% of the resulting colonies were white, indicating the presence of at least one single base difference in the 2 kb PCR products derived from the two different chromosome 21 homologues. The DNA sequence variation in the PCR products was independently verified by restriction enzyme digestion. These results demonstrate that MRD can be used to enrich for PCR products that are largely free of PCR-induced errors, and that such products can be used in conjunction with MRD to detect human DNA sequence variation.

TABLE 2

Percentage of Inactive Colonies in Different Comparison with Plasmids containing 2 kb PCR Products from two Somatic Cell Hybrids

| Variants Compared* | Percentage of Inactive Colonies# |
|---|---|
| 1/2 | >90 |
| 2/2 | >90 |
| A1/A1 | 70 |
| A2/A2 | 64 |
| AA1/AA1 | 38 |
| AA2/AA2 | 21 |
| AA1/AA2 | >90 |
| AA2/AA1 | >90 |

*1 and 2 represent products from the two hybrids. 1/1 represents comparison of "A" vector grown in a dam⁻strain and containing the PCR product from hybrid 1 to "I" vector grown in a dam⁺strain and containing the PCR product from hybrid 1. A1/A1 represents the comparison of "A" vector grown in dam⁻host, obtained from the active colonies of comparison 1/1, to I dam⁺grown vectors obtained from the same source. AA1/AA1 represents the comparison of A dam⁻grown vectors obtained from the active colonies of the comparison A1/A1 to I dam⁺grown vectors from the same source. Finally, AA1/AA2 represents the comparison of A dam⁻ grown plasmids obtained from active colonies of the comparison A1/A1 to I dam⁺grown vectors obtained from the active colonies of the comparison A2/A2.

It is evident from the above results that the subject invention provides for an efficient, simple method of detecting mismatches between two DNA sequences. The method provides a means of simply detecting the presence of a mismatch, or can be used to isolate copies of both matched and mismatched DNA. MRD is useful to determining somatic changes in gene sequence, identifying germline mutations for prenatal or other genetic screening, for human gene mapping, and for cloning mutations. A major advantage of MRD is the potential of this system to analyze many fragments simultaneously in a single experiment, allowing the detection of mutations in a region representing hundreds of kilobases of DNA, or for genotyping many loci simultaneously. MRD provides a powerful technique for the detection of unknown mutations, the detection of DNA variation in large genomic regions, and high-throughput genotyping.

EXAMPLE 4

Use of Cre-Lox as a Detectable Marker

Construction of the standards: MRD utilizes two vectors that are identical except for a five base pair deletion in the gene coding for Cre recombinase on one of the vectors. DNA fragments are cloned in the vector containing the wild type Cre. These clones, referred to as standards, are made only once and serve as sequence comparison templates for sequences from each person that is to be tested. Standards are grown in an E. coli host that is deficient in methylation, and subsequently unmethylated single stranded DNA is obtained.

Figure 6A:
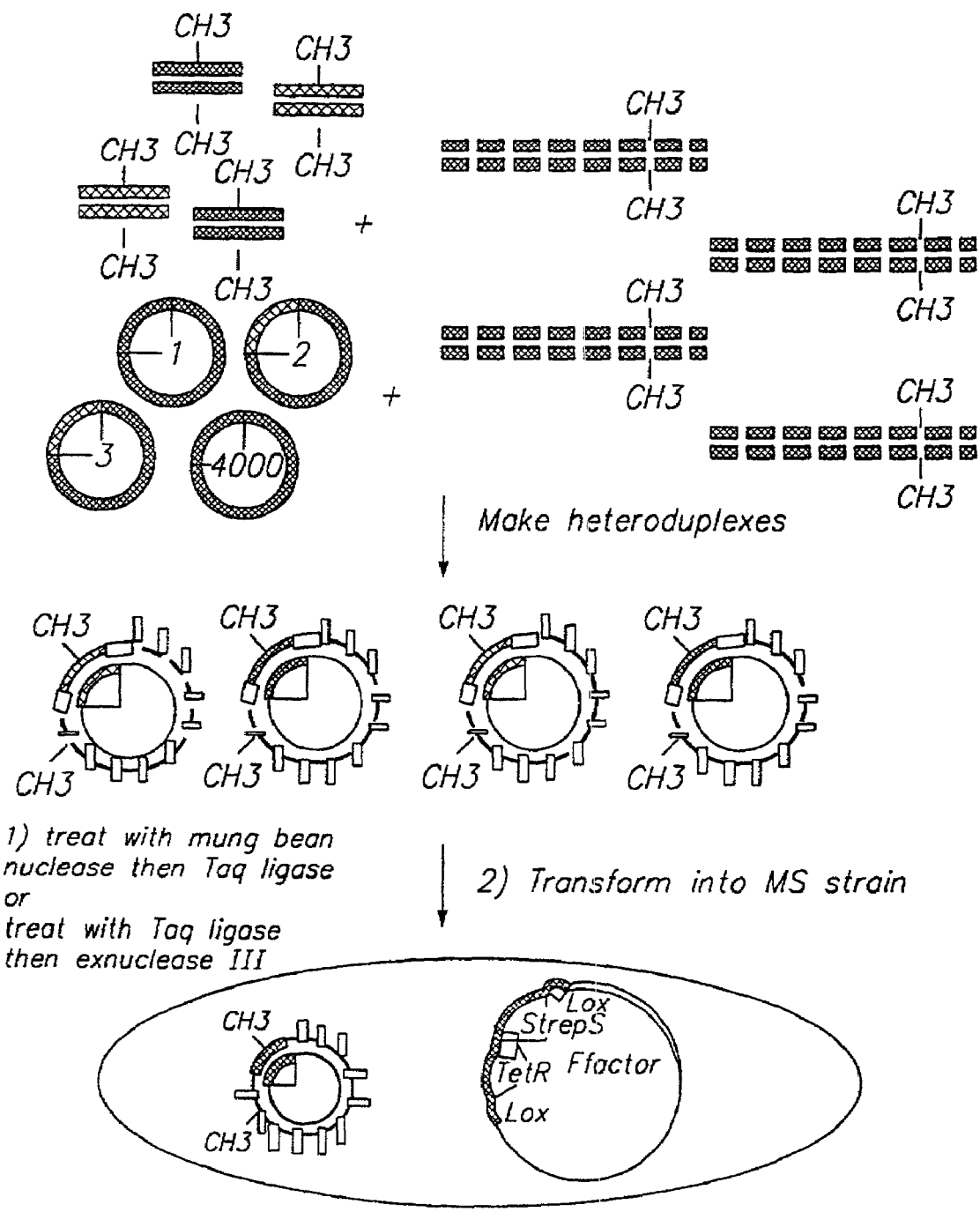
Figure 6B:
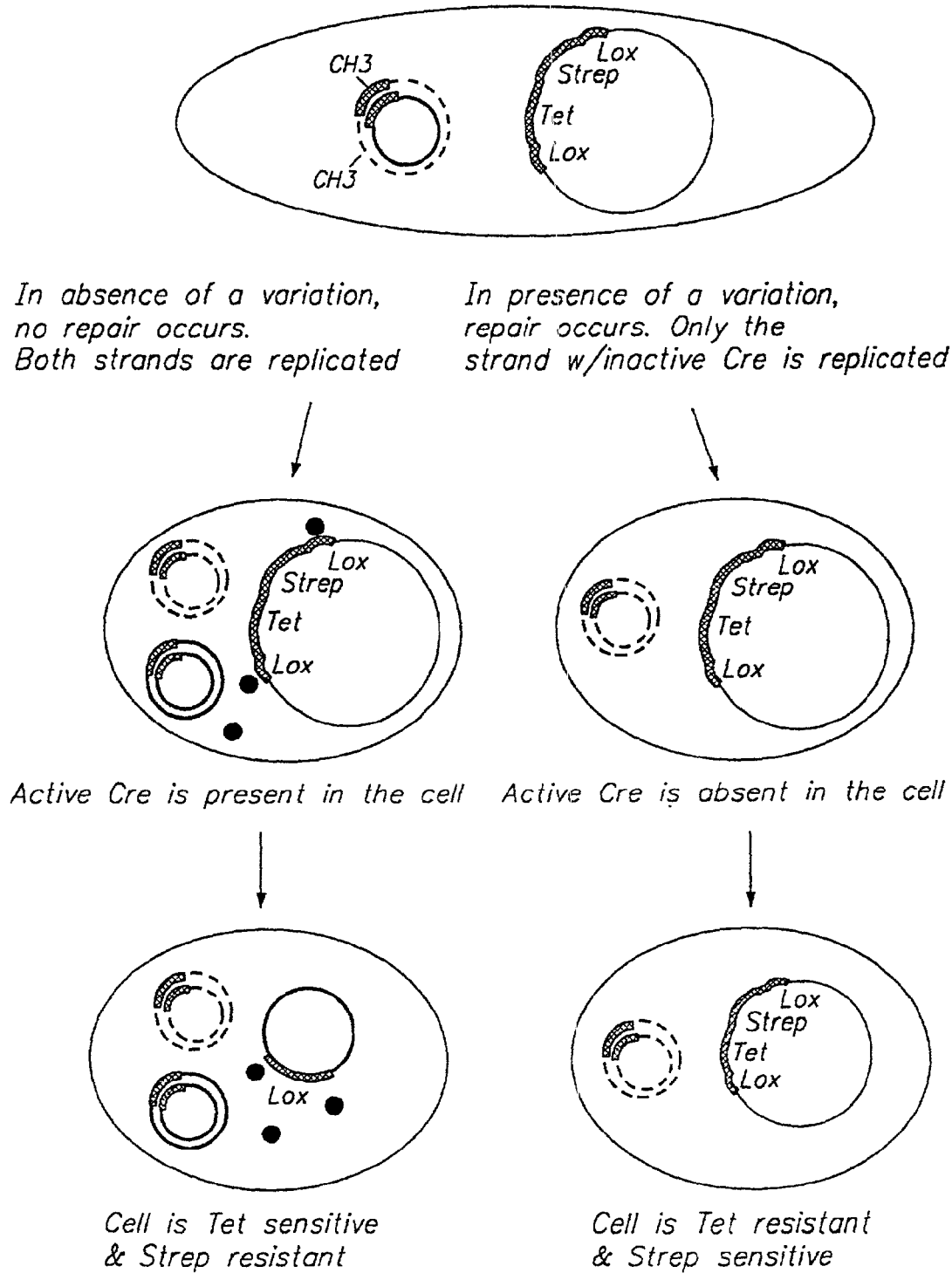

Heteroduplex preparation for DNA variation screening: In order to perform the screening for DNA variations, DNA fragments that are to be tested are amplified from each individual. After in vitro methylation of the PCR products, single stranded DNA from all of the standards are pooled and added to the tube containing the PCR products. Linearized vector containing the 5 base pair deletion in the Cre gene is also added to the same tube. The three components (the PCR products, the single stranded standards, and the linearized Cre deficient vector) are denatured by NaOH and reannealed by neutralization. This process creates heteroduplexes between the unmethylated single stranded standard, its complementary PCR product and the linearized Cre deficient vector, shown in FIG. 6.

Mung Bean nuclease is added to degrade remaining single stranded components. Taq ligase is then added to create closed-circle hemimethylated heteroduplexes. At this point a single tube contains all of the heteroduplexes corresponding to the standards and the gene fragments that are being tested. In a single reaction mixture the heteroduplex DNA is transformed into an electrocompetent E. coli strain (MUTATION SORTER™, MS) engineered to carry on an F episome a cassette of a tetracycline resistant (tetR) and streptomycin sensitive (strepS) genes flanked by two lox sites.

Separation of variant and non-variant DNA fragments: Those heteroduplex molecules carrying no mismatch (i.e., no variation between the standard and the DNA fragment that is being tested) replicate normally, and plasmids carrying both the active and inactive Cre will be present. The active Cre recombines the cassette between the two lox sites leading to the loss of the tetR and the strepS genes. This renders the cell tetracycline sensitive and streptomycin resistant, and hence it will grow in the presence of streptomycin but not tetracycline.

The presence of a mismatch (i.e., if there is a variation between a standard and the DNA fragment that is tested) in the heteroduplex molecules leads to the repair of such mismatches. In the process of repairing the mismatch the unmethylated strand carrying the active Cre gene is degraded and the strand carrying the inactive Cre is used as a template to be copied. As the result, the cell transformed with a mismatch heteroduplex is devoid of any Cre activity, permitting the cell to retain its $tet^R$ and $strep^S$ cassette and therefore grow in presence of tetracycline and not streptomycin.

By growing the transformation mixture in two tubes containing either tetracycline or streptomycin, fragments containing a variation and those that do not contain a variation are isolated, respectively. The evaluation of DNA variation detection is reduced to identifying which fragments are present in which pools. This task may be done in multiple ways including gel electrophoresis and hybridization.

Identification of Variant and Non-Variant DNA Fragments:

Using ABI sequencing gels: DNA from each pool is digested with restriction enzymes to release the fragments being tested. Samples of the two restriction digests are fluorescently labeled and run on an ABI sequencing gel. The presence or absence of variation in a fragment is assessed by determining the pool where the specific fragment is present. This can be achieved because the different fragments are separated from each other according to their size.

Using DNA Microarray Technology:

In this procedure all of the fragments that are represented in the standards are dotted onto slides. Subsequently the DNA obtained from the tetracycline containing culture and streptomycin containing culture are fluorescently labeled and used as hybridization probes. The probe from the tetracycline culture hybridizes to the spots corresponding to the DNA fragments that contain variation; the probe from the streptomycin culture hybridizes to the spots corresponding to DNA fragments that contain no variations. Other methods for the analysis of the fragment content of each pool can be utilized, including mass spectroscopy.

In order to achieve the goals of identifying variations involved in clinically relevant phenotypes, many genes need to be tested. This tremendous task is greatly facilitated by MRD's ability to multiplex. Many researchers have used whole cDNA content of the cell as the probe onto a microarray containing more than 10,000 targets. It is therefore be a relatively simple task to use a pool of 4,000 fragments as a probe on a microarray containing 4,000 targets. This will allow for the testing of 4,000 fragments simultaneously, although more samples could be multiplexed. In order to test the entire coding regions of the genes of one human individual, one could test 400,000 fragments with an average size of 300 bp each. It will then take 100 MRD reactions to achieve that task.

Disease-causing variations, by definition, have increased frequency in the patient population than in controls. Since construction of haplotypes and knowledge of every individual's genotype are not necessary to identify the disease-causing variations, patients or controls can be pooled and tested to estimate the frequency of different DNA variations in each population. MRD has the potential to simultaneously estimate the frequency of many variations in a population. First, genomic DNA from many individuals is physically pooled and used as template for subsequent MRD steps. The frequency of every variant fragment is estimated by determining its prevalence in the two pools obtained at the end of the procedure. Obtaining frequencies of different variant gene fragments in different populations, e.g., patients and controls, can quickly identify the fragments carrying disease-causing variations.

Multiplex MRD:

In order to demonstrate MRD's potential to multiplex, we have applied the MRD procedure to the identification of DNA sequence variation in 13 DNA fragments randomly selected from a group of published polymorphic Sequence Tagged Sites (STSs). In brief, standards were made for each STS, and heteroduplexes were made between a mixture of the standards and DNA fragments amplified from each individual tested. Heteroduplexes were transformed en masse into the MUTATION SORTER™ (MS) strain and grown in two separate cultures, one supplemented with tetracycline and the other with streptomycin. DNA from each of the two cultures was fluorescently labeled and loaded on the ABI sequencing machine. Fragment peaks were analyzed and the presence or absence of variations in a particular DNA fragment was assessed by determining the pool where a specific fragment was more prevalent (FIG. 7).

Shown in FIG. 7, the two samples prepared from the cultures supplemented with streptomycin or tetracycline, respectively, have different peak traces. The traces show the different peaks corresponding to the different fragments. Each peak is quantitated automatically. Assignment of the alleles of the tested individual is determined from the relative intensity of a fragment between the two pools. The predominance of a fragment in the streptomycin pool indicates the absence of a variation. In contrast, the predominance of a fragment in the tetracycline pool indicates the presence of a variation on both alleles. Finally, the abundance of a fragment in both pools indicates the individual tested is heterozygous for the fragment. These assignments are reproducible in independent testing. The signal to noise ratio for detecting a heterozygous variation is 10:1; and the detection of homozygous variation is substantially more robust.

The above experiment was performed on a nuclear family of 3 individuals. Each individual was tested three independent times. Variations were detected in all three individuals. Robust signal to noise ratio was obtained; heterozygous alleles were effectively identified with the average signal to noise ratio of 10:1. These results were perfectly reproducible as exactly the same variant fragments were detected in an individual in each of the three independent experiments. Different fragments were variant in the different individuals; the pattern of variation among the three people followed a Mendelian mode of inheritance. In these experiments the sensitivity, specificity and reproducibility of detecting DNA variations by MRD, as well as its potential for high throughput variation screening have been demonstrated.

MRD technology makes the large scale screening of candidate genes for identifying variations that cause common diseases a real possibility. At the heart of this approach lies the ability to identify genomic sequence variations that are more frequent in a particular patient group than the normal population. Identifying these variations can influence many aspects of modern medicine: determining diagnoses, assessing prognoses and devising treatments for human diseases. The knowledge of genetic factors causing common disease will impact medical care in a similar way it has already influenced care for rare simple Mendelian diseases.

EXAMPLE 5

Multiplex MRD

Materials and Methods
Construction of MRD Vectors and Strains
All the restriction and modifying enzymes used were from (New England Biolabs) (NEB). All the reactions were performed according to the enzyme manufacturer's recommendations except for the blunt end ligation that was performed using (Gibco BRL) ligation buffer. The bacterial strain used for all the transformations and growth was DH5α, unless otherwise specified.

Construction of Vectors
The Cre gene was PCR amplified using a construct carrying Cre as a template. The PCR left 13 bp 5' of the start ATG of the protein. The PCR product was cloned in Pst/BamHI digested pBSK (Stratagene). The Cre gene was then used to replace the LacZα gene in pMF200. To this end the Cre fragment was released by an Eco RI/Xba I double digestion and the ends were filled using the Klenow fragment. PMF200 was partially digested with BgI I and treated with T4 DNA polymerase to chew the 3' overhang followed by Bam HI digest (the Bam HI site is present in the leader sequence of LacZα of pMF100) and end filling by Klenow fragment. A blunt end ligation produced pMRD100, which replaced the LacZα gene on the BgI I-Bam HI fragment of pMF100 by the Cre gene. In this construct the plac promoter drives the expression of Cre.

PCR was performed using pMR100 as a template and the M13 reverse primer with a primer creating a 5 bp deletion in Cre. The deletion was for the sequence CTACA, 207 bp downstream from the ATG start site. The PCR product was digested with Nru I and Sph I. PMRD100 was also digested with Nru I and Sph I and the small fragment was substituted with the digest from the PCR product. The recombinant plasmid was pMRD200 carrying a 5 bp deletion in Cre but otherwise identical to pMRD100. Sequence analysis confirmed that no other change in Cre occurred except for the 5 bp deletion.

Construction of MUTATION SORTER™ Strain

The starting vector was pML11, a pBKS (Stratagene) derivative cloned in its multiple cloning sites the tetracycline gene flanked by two lox sites. In order to clone the wild type streptomycin sensitive gene (StrS), we performed PCR using a bacterial strain carrying the wild type gene as a template and the following primers:

StrI: GAG GGT AAC CGC TAC CTT GAA AGT C [SEQ ID NO:3]

StrII: GCT GAA TTC GTT TGG CCT TAC TTA ACG GAG AAG [SEQ ID NO:4]

The size of the StrS PCR product was about 700 bp. T4 Polymerase treatment was done to trim the ends, followed by an Eco RI digest to produce a substrate for directional cloning. This fragment was cloned in Eco RI/Sma I digested pML11 replacing the tetracycline gene and producing pMLstrp. In order to put the streptomycin and tetracycline genes in tandem, the large fragment of pML11 digested with Kpn I/Sma I was ligated with the small fragment of pMLstrp, that was EcoRI digested, Klenow filled with subsequent Kpn I digestion. The recombinant produced was pMLST. PMLST was then digested with Xho I/Sac I releasing the tetracycline/streptomycin/lox cassette. The fragment was cloned in pLitmus 29 (NEB) digested with Xho I/Sac I. The resultant plasmid, pMLSTB, was digested with Kpn I and BgI II linker was inserted.

In order to put the construct on the bacterial F' episome, we utilized the vector pNK2859 (41) carrying the transposase gene. This plasmid produces a stable transposition event, as the transposase gene carried on the plasmid does not get transferred itself. We ligated a BgI II fragment of pMLSTB carrying the cassette of interest with a Bam HI digest of pNK2859. The obtained plasmid pNKMLST carried the fragment of interest flanked by a transposition signal. The plasmid also carried the transposase gene that catalyzes the transposition event but does not get transposed itself.

We transformed pNKMLST into a DH5α strain carrying an F' episome. This strain was grown and in some cells transposition events to the episome presumably happened. In order to isolate those cells, the culture was mated to HB101 containing a plasmid with a temperature sensitive replication and chloramphenicol (Cm) resistance gene. The transfer of an F' episome carrying the transposition product to HB101 should transmit the tetracycline resistance phenotype. The mating was performed as described previously (42). Selection for tetracycline and chloramphenicol resistance was done. Selected colonies were screened for carbenicillin (Carb) and streptomycin sensitivity (HB101 is streptomycin resistant). The desired conjugants had the following phenotype: TetR, CmR, CarbS, and StrpS. Growth at 42° C. was performed to get rid of the plasmid carrying the Cm resistant gene. Different isolates were obtained that presumably carry the tet/str/lox cassette at different places on the F' episome. Through transformation with pMRD100, pMRD200 as well as the heteroduplex, the strain, named conj5, with the least background was selected.

Although conj5 was used for some MRD experiments, we preferred to use the DH5a background. Selection for a streptomycin resistant mutant was done in DH5a by plating a culture on a plate containing (10 mg/mil) streptomycin. The new strain was called DH5αS. The F' episome of conj5 was transferred to the DH5αS strain by mating with a huge excess of DH5αS. The conjugation was performed by mixing the two strains at 1:1000 ratio and leaving them at 37° C. overnight before selection on tetracycline XgaI/IPTG plates. The DH5αS that have acquired the F' episome were distinguished from conj5 by the colony color because the former appears white whereas the latter is blue on IPTG/XgaI plates. The DH5αS with the F' episome carrying the tet/str/lox cassette is called the MUTATION SORTER™ (MS) strain.

Construction of Standards pMRD100 was grown in the dam⁻ host, SCS110 (Stratagene), and unmethylated DNA was prepared. The vector DNA was digested with Hinc II and the linear molecule was purified by agarose gel electrophoresis (gel purification not necessary). PCR reactions from an individual were performed using pfu polymerase (Stratagene). In some cases, a few of the products were pooled. The PCR products were cleaned using DNA binding columns (Qiagen) according to the manufacturer protocol. Ligation reaction was set up between the linearized vector and 1–10 PCR products with the latter being used in excess. After ligation overnight at room temperature, a (Qiagen) column purification was performed to get rid of the ligase and salts. Sal I digestion reaction was then performed to linearize DNA vectors that do not contain inserts. Another (Qiagen) column purification was performed before electroporation into SCS110 cells using (Biorad) electroporation equipment as described previously (43). In order to identify the colonies containing a recombinant molecule, PCR was performed from individual colonies using T3 and T7 as primers. PCR products that contain inserts were then subjected to sequencing using the dideoxy chemistry and T3 as a sequencing primer, Proper clones, as determined by sequencing, are the standards that are used as a reference for comparison with the test DNA. Alternatively the ligation products were transformed into DH5α instead of SCS110. The proper clones were later transformed into SCS110. Single stranded unmethylated DNA of the standards were prepared by using the helper phage M13K07 (NEB) according to the manufacturer recommendations. In later experiments we deployed a more efficient process for the standard construction. One hundred PCR fragments are pooled together and cloned to create a library for these clones. Sequencing of the clones identifies those that can serve as standards. Another round of cloning is done for those clones not obtained in the first round.

MRD Protocol

For each MRD reaction, approximately 1 mg total of the pool of the unmethylated single stranded standard DNA were digested with 5 units of MboI for 30–60 minutes at 37° C. to destroy any double stranded contamination (in later experiments we have used ScrF I instead of Mbo I). The enzyme and the buffer were removed using a (Qiagen) column. About 2 mg of vector carrying the inactive Cre gene was digested with Hinc II and purified by gel electrophoresis (gel purification is not necessary). The above two preparatory steps were generally done in big batches and aliquots were used in the subsequent MRD reaction.

PCR reactions from the tested individual were done using pfu polymerase. The template tumor cell line DNA used in the initial experiment to test many fragments simultaneously, was obtained from (ATCC). The template DNA for the experiments testing the specificity and sensitivity of MRD were for individuals from the NIH DNA Polymorphism Discovery Resource (44). The PCR products from one individual were pooled and a purification using a (Qiagen) column was performed. The PCR pool was then phosphorylated (if primers did not have a 5' phosphate from the synthesis) with 10 units of Polynucleotide Kinase (NEB) for 1–2 hrs at 37° C. The enzyme and the buffer were then removed by treatment with the SOPE resin/column from (Edge Biosystems) (EB). Dam methylation was then performed using dam methylase (NEB) at 37° C. for 1–2 hrs according to the manufacturer recommended buffer. (Qiagen) column purification was then performed to remove the enzyme and the buffer. The methylated PCR was mixed with 1 mg of the above-described unmethylated standards and 2 mg of the purified linear vector carrying the inactive Cre. 5 ml of 0.5M EDTA and 1.5 ml of 3M NaCl were added and the volume was adjusted to 100 ml with TE. 12.5 ml of freshly diluted 1 M NaOH was added and incubation for 15' at room temperature followed. 12.5 ml of 2M Tris PH=7.2 and 125 ml formamide were then added and reannealing was allowed to occur at 30° C. overnight. The heteroduplex was cleaned using (Qiagen) column and resuspended in 30 ml $H_2O$. 3.5 ml Taq Ligase buffer, 1 ml of Ethidium Bromide (300 mg/ml) and 1 ml Taq Ligase (NEB) were added. The addition of the Ethidium Bromide was not essential but it may improve the signal to noise ratio. Nick closure reaction was performed at 65° C. for 15'. SOPE resin/(EB) column were used to remove the enzyme and the buffer. Fifty units of Exonuclease III (NEB) was then used with the appropriate buffer to convert the nicked DNA to single stranded molecules. Another SOPE Resin/(EB) column step was utilized to remove the enzyme, buffer, and the single stranded DNA. To ensure the removal of all the single stranded DNA, 0.7 mg Benzoylated Naphthoylated DEAE Cellulose (BNDC) was added and NaCl added to final concentration of 1 M, and incubation proceeded for 15', shaking at room temperature. BNDC binds preferentially to single stranded DNA. The mixture was run over an (EB) column to remove the salt and the BNDC with its bound single stranded DNA. Although the results described in this work utilize the BNDC step, the deletion of this step did not affect results. After removing the single stranded DNA, the closed circular heteroduplex molecule was concentrated by speed vacuum. The preparation of the closed circular heteroduplex molecules for the initial experiment testing 32 exons was performed employing an alternative protocol. We purified the closed circular molecules using agarose gels elecltrophoresis. To eliminate this step, the exonuclease ill step was employed in later experiments as described above.

Transformation of the MS strain was done by electroporation. The electrocompetent MS cells preparation as well as the electroporation procedure was done as recommended (43). During the 1 hour recovery phase 1 ml of 1 M IPTG was added to the SOC medium. The culture was split into two parts that were plated onto two plates supplemented with Carbenicillin (75 mg/ml), Streptomycin (10 mg/ml) and IPTG (64 mg/ml) or Carbenicillin (75 mg/ml), Tetracycline (3.25 mg/ml) and IPTG (64 25 mg/ml). Typically, a total of about 1 million transformants is obtained. One ml of LB is put on each of the two plates and all the colonies from a plate are then collected into a tube. All of the experiments described used plates except the initial experiment with the 32 different fragments where the transformation mixture was grown in two cultures with the appropriate selective media. In both cases (plates or cultures) DNA from the cells obtained after the overnight growth with the selective media were miniprepped using the Qiagen columns as recommended by the manufacturer. Fifteen to thirty percent of the DNA obtained in the miniprep was digested with Cla I and Xho I (NEB) at 37° C. for 1–2 hrs. When agarose gels were employed, the DNA was run on a 4% New Sieve gel. When ABI 377 gels were used, the digested DNA was passed over a filter column (EB) to get rid of the salt. The restriction fragments were labeled utilizing a fluorescent dUTP. This was achieved by adding 0.5 units of ampliTaq polymerase (Perkins Elmer), Taq buffer and $MgCl_2$ at the recommended concentration as well as R6G dUTP (Perkins Elmer) at a final concentration of 0.8 mM. The nucleotide extension reaction was performed at 72° C. for 10'. (EB) column was then used to remove the excess fluorescence. The sample was concentrated by speed vacuum and then run on an ABI 377 sequencing gel. The data were analyzed by Gene Scan software (Perkin Elmer). Fragments were determined to carry a variation if the ratio in the tetracycline to the streptomycin pool is significantly higher than that of non-variant fragments.

Results

To test MRD's capacity for multiplexing, we performed MRD on a pool of 32 exons of genes involved in cancer pathogenesis or progression. We initially constructed a panel of 32 standard plasmids by cloning PCR products of the specific exons from one individual in the pMRD100 containing the active Cre gene. These plasmids were then pooled and served as a reference to compare with the test DNA. Thirty-two PCR reactions were performed in each of three independent tumor cell lines. The MRD procedure was performed with the PCR pools of each of the three tumors. After transformation, DNA was prepared from the two bacterial cultures grown in the presence of tetracycline or streptomycin. An agarose gel was run for a restriction digest that released the inserts of the DNA pools. The tetracycline pool, compared with the streptomycin pool, contained a higher proportion of variants between the standard and test DNA. We identified, in the three tumors, five such variant fragments in four distinct exons.

The exons predicted by MRD to carry variations were Patch exon 17, Cadherin exon 14, Ataxia Telangiectasia Mutated (ATM) exon 31, and P53 exon 7. The Patch 17 exon was variant in two of the tumors. We sequenced Patch exon 17, Cadherin exon 14, and P53 exon 7 in all 3 tumors, and sequenced ATM exon 31 only in the tumor expected to carry the variation. The sequencing analyses confirmed all of the variants identified by MRD.

PCR products of the above experiment were run on an agarose gel before they were pooled. Some of these PCR products were quite impure with the proper product representing minor specie. This impurity did not interfere in the MRD results, showing that MRD can tolerate a high degree of PCR impurity.

Testing the Specificity of MRD

We tested the specificity of MRD in a more complex background than in the above experiments by using an automated sequencing apparatus (ABI 377) to simultaneously scan 45 fragments derived from exons of genes involved in cancer pathogenesis and progression. Although we were able to identify multiple variations (data not shown), some fragments had the same size and therefore could not be analyzed.

We eliminated fragments that could not be resolved on the sequencing gels and tested only 35 fragments in subsequent experiments. We used MRD to scan for variations in 14 individuals these 35 fragments that encompass over 10 kb of DNA.

FIG. 8 represents the result of one such scan demonstrating a typical trace of the streptomycin and tetracycline pools of an MRD experiment run on an automated sequencing apparatus. One fragment was missing in both pools in all individuals and another was present in only a few individuals presumably because of PCR failure. In these 14 individuals, we identified seven variations (Table 3).

TABLE 3

Variations identified by MRD by scanning 35 exons for variations in 14 individuals

| Exon | Size of fragment tested (bp) | Number of individuals with a variant fragment | Nature of variation |
|---|---|---|---|
| ATM exon 6[a] | 257 | 2/14 | A --> transversion |
| ATM exon 30 | 294 | 1/11 | Transition |
| ATM exon 25[a] | 297 | 9/14 | 1 bp del/ins |
| Patch exon 17[a] | 303 | 9/14 | Transition |
| MKK exon 7 | 412 | 1/14 | Transition |
| BRCA1 exon 11[b] | 423 | 4/13 | Transition |
| BRCA1 exon 16 | 441 | 3/14 | Transition |

[a]Fragment was sequenced in all 14 individuals.
[b]The fragment tested does not encompass the whole exon.

All seven variations were confirmed by subsequent sequencing, and consisted of five transitions, a transversion, and a one base pair (bp) deletion/insertion variant. We evaluated the consistency of MRD in detecting the same variation in different samples, by sequencing all 14 individuals for three of these fragments. Only the individuals predicted by MRD to carry variations showed variants by sequencing. In the above two experiments we MRD-screened more than 400 fragments and obtained no false positives. Since not all the fragments were sequenced, this experiment did not address sensitivity.

Testing the Sensitivity of MRD

To test the sensitivity of MRD, we evaluated its ability to detect previously identified variations. We chose Sequence Tagged Sites (STSs) known to carry SNPs, testing a total of five unrelated individuals using sequencing and MRD. These STSs included eight SNPs from published reports confirmed by us through direct sequencing, and two SNPs identified by us using sequencing. We made a standard for each of the STSs. All 10 of these SNPs were detected by MRD (Table 4).

| STS name | Nature of variation | SNP identified |
|---|---|---|
| WIAF-620 | C --> G transversion | |
| WIAF-621 | Transition | |
| WIAF-1591 | Transition | |
| WIAF-1402 | Transition | |
| WIAF-333 | Transition | |
| WIAF-468 | G --> T transversion | |
| WI-945 | Transition | This work |
| WI-6819 | 1 base del/ins | This work |
| WIAF-1187 | G --> T transversion | |
| WIAF-1323 | C --> A transversion | |

Discussion

Our results show that MRD can scan for variations in multiple genomic fragments simultaneously with high specificity and sensitivity, is highly tolerant of PCR impurities, and that a single condition can be used for all the fragments tested without any need for optimization. All of these features are important for high throughput applications.

The use of standards in this implementation of MRD provides several benefits for high throughput variant detection. First, one is always comparing the test DNA with the same reference sequence. Second, by using standards one increases efficiency by avoiding any intermolecular ligation step. Finally, by analyzing the test DNA with two standards for two alternative common alleles, it is possible to distinguish the common variants from other alleles.

The number of fragments tested in the experiments described above is limited due to the relatively low resolution of sequencing gels. Methods with better power to distinguish between fragments are necessary to achieve the full potential of MRD. For example, microarray hybridization is now widely utilized for various quantitative assays using thousands of DNA fragments simultaneously. By adapting microarray hybridization technology as the last detection step in the MRD procedure, we anticipate that thousands of fragments can be scanned for variations simultaneously.

The different MRD steps likely can accommodate up to 5,000 fragments simultaneously, including the hybridization step leading to heteroduplex formation and the transformation step. This hybridization is less complex than solution hybridizations that have previously been carried out successfully (28). We typically obtain at the end of the MRD procedure a million transformants; this number should be sufficient for analyzing up to about 5,000 fragments. The microarray hybridization step will be simpler than typical microarray expression applications that use more than 10,000 genes as a target and the whole cell RNA as a probe. The signal to noise ratio for MRD is likely to remain favorable as it scales up to applications involving many thousand fragments, as each fragment is detected independently. Our experience so far, showed that this ratio remained constant in the scale-up from two to 45 fragments.

Because of its potential for multiplexing, MRD is most suitable to those applications where many fragments in many individuals are scanned for variations. Currently the only scanning technology that can accommodate a significant degree of multiplexing is VDA, which has been used to scan for variations in as much as 30 Kb of human DNA, about 3 fold more DNA than covered in the work presented here. However this application of VDA encountered problems with both sensitivity and specificity. In addition, the large number of probes needed limits the throughput and increases the cost of VDA. For example, at least 3,000 oligos on the array are required using VDA to scan a 300 bp fragment for variations. In contrast using MRD with array hybridization as the readout, as proposed above, a 300 bp fragment can be scanned for variations with one probe on the array. The difference in the number of probes needed to interrogate each fragment is reflected in a potentially much higher throughput and lower cost for MRD.

Given the absence of a high throughput scanning technology and the relative wealth of SNP genotyping methodologies, proposals for identifying susceptibility alleles for common diseases have focused on genotyping a universal set of common SNPs. These approaches assume that disease susceptibility alleles are common. Only a few genes contributing to common disease have already been identified. The alleles involved in these diseases in some instances were common, but in several other instances relatively rare alleles are associated with or causative of disease. Recent studies have scanned for variants in numerous genes considered possible candidates for involvement with common diseases; these studies have shown that, in general, non-synonymous coding sequence variants are relatively infrequent, and are often specific to a particular ethnic population. It is likely that common disease is caused by a combination of common and rare alleles. A comprehensive sequence comparison of genes among patients and controls permits high-throughput detection of the rare or ethnically specific alleles and therefore provides a more comprehensive model than currently proposed for the elucidation of the genetic basis of common disease. Such comparisons can be carried out by direct sequencing, however this is currently a prohibitively expensive undertaking.

We propose that MRD analysis of all the coding and regulatory regions of all genes can provide comprehensive sequence comparison of selected patients and controls to identify disease-associated variants. By testing in a single MRD reaction, 5,000 fragments that are on average 300 bp in length, one could perform such sequence comparison on 1.5 megabase (Mb) of genomic DNA. Therefore, in 100 MRD reactions, one could scan up to 150 Mb of DNA, an amount larger than the estimated total of the coding regions in an individual. Multiple developments need to occur before MRD can be applied on this scale, including the identification of the finished sequence for all genes and their regulatory regions, the construction of several hundred thousand standards, and either advancement in PCR multiplexing or alternative ways to capture many DNA fragments. Over the short run, we propose using MRD to identify SNPs that can be scored by MRD or other genotyping methods and using MRD to scan for variations in panels of candidate genes in patients and controls.

EXAMPLE 6

Microarray Detection

To demonstrate utility of microarray detection in MRD multiplexing, 2 yeast strains, S288C and S31, that differ by one base in the Lys5 gene, are used.

Standard clones are constructed from PCR products of S288C. The PCR products are for different open reading frames (ORF) at various sites in the genome and their sizes range from 80–1000 bp with an average of 700 bp. To construct standards, the PCR products are pooled, ligated into an MRD vector carrying an active cre gene, and transformed into a dam⁻ strain. Individual transformants of the dam⁻ strain are sequenced to determine the cloned fragments: 576 different clones are identified and are later used as standards. Single stranded DNA from the pool of standards is prepared.

The single stranded DNA from the pool of standards is hybridized to linear vector carrying the inactive cre and a pool of PCR products from S288C and the Lys5 PCR product from S31. Heteroduplex formation and transformation into MUTATION SORTER™ strain are done as described above. DNA from the two pools of colonies—those grown in the presence of tetracycline and those grown in the presence of streptomycin—is later prepared and linearized.

T3 RNA transcription reaction with fluorophore-labeled dUTP (fluorescein for the streptomycin pool and biotin for the tetracycline pool) is performed separately for each of the two DNA samples. The resulting RNA is then hybridized in two separate reactions to a yeast genome microarray chip (one such microarray chip available commercially contains, for each ORF, 16 pairs of oligonucleotides with one of the oligonucleotides of each pair representing a perfect match to the hybridized RNA, and the other a control having a mismatch).

The hybridization signals obtained using the tetracycline-grown pool and the streptomycin-grown pools are separately determined and compared. Results identify 9 genes with a much increased signal in the tetracycline pool than the streptomycin pool, indicative of a variation. One of the 9 is a variation in Lys5, as expected. Four of the nine represent gene families, the members of which have differences of a few bases among family members, which were commonly amplified and spuriously heteroduplexed. Two of the nine have PCR error in the standard.

EXAMPLE 7

Reduced Background from an Improved MRD Vector/Host Strain System

To test whether poor transcription and/or translation of Cre recombinase by the mismatch repair detection (MRD) vectors first described contributes to background in the MRD assay, plasmids containing cre driven by the strong T7 promoter, and having the RBS of φ10, were constructed. The two vectors (pT7MRD100 and pT7MRD200) differ only by the presence of a 5 bp inactivating deletion in cre in pT7MRD200.

A new *E. coli* host strain, 5HT71, was constructed by lysogenizing HB101 with lambdaDE3 (which has the genotype: imm21, Δnin5, sam7, int::lacUV5-T7RNA polymerase), and then introducing the F' episome from the MUTATION SORTER™ strain described in Example 5, above, by conjugation, thus creating a strain with the following genotype: F'(lox TetR RpsI Lox)/Δ(gpt-proA)62, leuB6, SupE44, Ara-14, galK2, LacY1, Δ(mcrR-mrr), rpsl20, xyl-5, mlt-1, recA13, λDE3 (imm21, Δnin5, sam7, int::lacUV5-T7 RNA polymerase). We term this 511T71 strain the MUTATION SORTER PRO™ strain.

The two vectors were transformed into separate aliquots by electroporation, supplementing the media used for the recovery after transformation with IPTG; the IPTG induces expression of T7 polymerase from the lambda lysogen. Transformants were plated after an hours recovery on selection plates lacking IPTG.

Transformants of the plasmid carrying the active cre, pT7MRD100, grew as expected on the plate supplemented with ampicillin and streptomycin, but not on plates supplemented with ampicillin and tetracycline. Transformants of the plasmid carrying the inactive cre, pT7MRD200, grew as expected on the plate supplemented with ampicillin and tetracycline, but not on plates supplemented with ampicillin and streptomycin.

To test whether the new vectors effected any change in the signal: noise ratio in an MRD assay, we analyzed two control fragments known to contain certain variations. We cloned the two fragments into the plasmid carrying the active cre, pT7MRD100. Single stranded DNA from these clones was used to hybridize with linearized pT7MRD200 and PCR products of the test fragments.

In one experiment, one of the test fragments had a variation in a heterozygous state, and the other fragment had no variation. After annealing, Taq ligase and exonuclease III treatments, as well as single stranded elimination by SOPE resin, were performed.

H5T71 was transformed by electroporation and the cells allowed to recover in the presence of IPTG for one or two hours before plating on plates containing combinations of either ampicillin and tetracycline, or ampicillin and streptomycin. The colonies from each of the two selection conditions were separately pooled, miniprepped, and the duplex fragments released by restriction endonuclease digestion. The restriction digest was subjected to agarose gel electrophoresis for resolution and quantitation of the fragments.

FIG. 11 is a photograph of the stained agarose gel. The first lane is a size marker. In all the other lanes, the top band is the variant fragment, and the bottom band is the nonvariant fragment, distinguishable on the basis of size. The second lane (from the left) is from the streptomycin (nonsorted) pool with one hour recovery in the presence of IPTG. The third lane is from the streptomycin (nonsorted) pool with two hours' recovery in the presence of IPTG. The fourth and fifth lanes are loadings of two different amounts of the same sample: the tetracycline pool (sorted pool) with one hour recovery. The sixth and seventh lanes are loadings of two different amounts of the tetracycline pool with two hour recovery.

As shown in FIG. 11, the intensity ratio of the heterozygous fragment in the sorted (tet+) pool vs. nonsorted (strp+) pool (conveniently termed the "sort ratio") is much greater than that of the non-variant fragment, indicating that the mismatched duplex properly initiated cre corepair, leading to correct phenotypic sorting.

The signal to noise ratio can be calculated as the relative sort ratio as between known heteroduplex and known homoduplex.

With these new vectors transformed into the MUTATION SORTERPOR™ strain, the relative sort ratio is about 20, about 4-fold better than is seen with the vectors and strain described in Example 5. We have performed a similar experiment using a variation in a homozygous state. A similar improvement in the signal to noise ratio was also demonstrated (not shown).

As also shown in FIG. 11, there was no detectable difference between 1 hour recovery with IPTG or 2 hour recovery with IPTG, suggesting that by one hour, enough cre had been expressed to catalyze the recombination event.

Not shown, when pT7MRD100 or pT7MRD200 was transformed into the MUTATION SORTERPOR™ strain and the plates were supplemented with IPTG, no colonies grew. On the other hand, when transformed with the control plasmid puc19, H5T71 readily produced colonies on IPTG ampicillin plates. This suggests that the continuous induction of cre (whether in active or inactive form) by the strong promoter T7 is lethal. This also suggests that the new vectors have higher cre expression than the original vectors as the latter, with Cre driven directly from the lac promoter, could routinely be plated on media supplemented with IPTG.

What is claimed is:

1. A method of identifiably detecting a mismatch in any of a plurality of DNA duplexes of distinct nucleic acid sequence, comprising:
   phenotypically sorting from said plurality of distinct duplexes those that initiate a mismatch corepair event in a bacterial cell, to form a phenotypically sorted population, wherein such mismatch repair event takes place only when there are together in a polynucleotide within the bacterial cell (i) a distinct duplex having a mismatch of from 1 to 4 contiguous nucleotides in length, and (ii) an inactive marker having a mismatch of at least 5 nucleotides in length that does not activate the methyl-directed mismatch repair system of the bacterial cell, and wherein such marker is repaired to generate a distinguishable cellular phenotype; and then
   identifying the duplexes present in said phenotypically sorted population,
   wherein identification is effected by identifying at least one genotypically detectable genetic element uniquely linked to each said phenotypically sorted duplex.

2. The method of claim 1, wherein each of said at least one genotypically detectable genetic elements is a nucleic acid sequence tag, each of said sequence tags being unique among said plurality of sequence tags, and wherein said sorted duplexes are identified by specific hybridization of said sequence tags, tagged duplexes, or nucleic acids derived therefrom, to a microarray having probes complementary to said plurality of sequence tags.

3. The method of claim 2, wherein each of said plurality of distinct sequence-tagged duplexes is itself further linked to at least one priming sequence, said at least one priming sequence being sufficient to allow enzymatic amplification of the tagged duplex linked thereto.

4. The method of claim 2 or claim 3, wherein each of said sequence tags is at least 17 nucleotides in length.

5. The method of claim 4, wherein each of said sequence tags is at least 20 nucleotides in length.

6. The method of claim 5, wherein each of said sequence tags is at least 25 nucleotides in length.

7. The method of claim 1, wherein at least one among said plurality of distinct DNA duplexes has at least one strand identical in sequence to a naturally-occurring genomic sequence.

8. The method of claim 7, wherein each of said at least one duplexes having sequence identical to naturally-occurring genomic sequence is obtained by amplification from a genomic template.

9. The method of claim 7 or claim 8, wherein said genomic sequence is a eukaryotic genomic sequence.

10. The method of claim 9, wherein said eukaryotic genomic sequence is selected from the group consisting of: yeast genomic sequence, plant genomic sequence, and mammalian genomic sequence.

11. The method of claim 10, wherein said eukaryotic genomic sequence is mammalian genomic sequence.

12. The method of claim 11, wherein said mammalian genomic sequence is selected from the group consisting of: murine genomic sequence, rattus genomic sequence, and human genomic sequence.

13. The method of claim 12, wherein said mammalian genomic sequence is human genomic sequence.

14. The method of claim 7, wherein said plurality of distinct DNA duplexes includes at least two duplexes having the sequence of different allelic variants of a single genomic locus.

15. The method of claim 14, wherein said plurality of distinct DNA duplexes includes at least three duplexes having the sequence of different allelic variants of a single genomic locus.

16. The method of any one of claims 1, 7 or 14, wherein said plurality of distinct DNA duplexes includes at least 10 distinct DNA duplexes.

17. The method of claim 6, wherein said plurality of distinct DNA duplexes includes at least 100 distinct DNA duplexes.

18. The method of claim 17, wherein said plurality of distinct DNA duplexes includes at least 1000 distinct DNA duplexes.

19. The method of claim 18, wherein said plurality of distinct DNA duplexes includes at least 5000 distinct DNA duplexes.

20. The method of claim 19, wherein said plurality of distinct DNA duplexes includes at least 10,000 distinct DNA duplexes.

21. The method of claim 1, further comprising:
   phenotypically sorting from said plurality of distinct duplexes those that are incapable of initiating a mismatch corepair event in vivo; and then
   identifying duplexes present in said further phenotypically sorted population,
   wherein said identifying is identification of at least one genotypically detectable genetic element uniquely linked to each said duplex.

* * * * *

SEQUENCE LISTING

<160> NUMBER OF SEQ ID NOS: 2

<210> SEQ ID NO 1
<211> LENGTH: 34
<212> TYPE: DNA
<213> ORGANISM: lambda phage

<400> SEQUENCE: 1
ataacttcgt ataatgtatg ctatacgaag ttat            34

<210> SEQ ID NO 2
<211> LENGTH: 34
<212> TYPE: DNA
<213> ORGANISM: lambda phage

<400> SEQUENCE: 2
acaacttcgt ataatgtatg ctatacgaag ttat            34